US008956802B2

(12) United States Patent
Iwato

(10) Patent No.: US 8,956,802 B2
(45) Date of Patent: Feb. 17, 2015

(54) PATTERN FORMING METHOD, CHEMICAL AMPLIFICATION RESIST COMPOSITION AND RESIST FILM

(71) Applicant: Fujifilm Corporation, Tokyo (JP)

(72) Inventor: Kaoru Iwato, Shizuoka (JP)

(73) Assignee: FUJIFILM Corporation, Tokyo (JP)

( * ) Notice: Subject to any disclaimer, the term of this patent is extended or adjusted under 35 U.S.C. 154(b) by 11 days.

(21) Appl. No.: 13/837,515

(22) Filed: Mar. 15, 2013

(65) Prior Publication Data

US 2013/0202999 A1 Aug. 8, 2013

Related U.S. Application Data

(63) Continuation of application No. PCT/JP2011/070623, filed on Sep. 9, 2011.

(30) Foreign Application Priority Data

Sep. 16, 2010 (JP) ................................. 2010-208625

(51) Int. Cl.
| | | |
|---|---|---|
| G03F 7/004 | (2006.01) | |
| G03F 7/20 | (2006.01) | |
| H01L 21/027 | (2006.01) | |
| C07D 209/70 | (2006.01) | |
| G03F 7/038 | (2006.01) | |
| G03F 7/039 | (2006.01) | |
| G03F 7/32 | (2006.01) | |

(52) U.S. Cl.
CPC ............. *G03F 7/20* (2013.01); *H01L 21/0274* (2013.01); *C07D 209/70* (2013.01); *H01L 21/0275* (2013.01); *G03F 7/004* (2013.01); *G03F 7/038* (2013.01); *G03F 7/039* (2013.01); *G03F 7/32* (2013.01); *H01L 21/027* (2013.01); *G03F 7/0045* (2013.01); *G03F 7/0392* (2013.01); *G03F 7/0397* (2013.01); *G03F 7/325* (2013.01); *C07C 2104/00* (2013.01); *Y10S 430/114* (2013.01); *Y10S 430/115* (2013.01); *Y10S 430/128* (2013.01)
USPC ........ 430/270.1; 430/332; 430/331; 430/329; 430/435; 430/913; 430/914; 430/927

(58) Field of Classification Search
CPC ....... G03F 7/004; G03F 7/0045; G03F 7/038; G03F 7/039; G03F 7/0392; G03F 7/0397; G03F 7/20; G03F 7/32; G03F 7/325; Y01S 430/913; Y01S 430/927; Y01S 977/734; H01L 21/00; H01L 21/02; H01L 21/02104; H01L 21/027; H01L 21/0271; H01L 21/0273; H01L 21/0274; H01L 21/0275; C07C 2104/00; C07D 209/70
USPC ............. 430/270.1, 322, 331, 329, 435, 913, 430/914, 927
See application file for complete search history.

(56) References Cited

U.S. PATENT DOCUMENTS

| | | | |
|---|---|---|---|
| 6,117,617 A * | 9/2000 | Kanayama et al. ............ 430/296 |
| 6,613,771 B2 * | 9/2003 | Friedman et al. .............. 514/256 |
| 2006/0105273 A1 | 5/2006 | Fukuda et al. | |
| 2006/0188809 A1 * | 8/2006 | Hatakeyama et al. ...... 430/270.1 |
| 2007/0190447 A1 * | 8/2007 | Ogata et al. ................. 430/270.1 |
| 2008/0118874 A1 * | 5/2008 | Robinson et al. .............. 430/327 |
| 2008/0187860 A1 | 8/2008 | Tsubaki et al. | |
| 2008/0261150 A1 | 10/2008 | Tsubaki et al. | |
| 2010/0035181 A1 * | 2/2010 | Sakaguchi et al. .......... 430/271.1 |
| 2010/0190106 A1 | 7/2010 | Tsubaki | |
| 2010/0323305 A1 | 12/2010 | Tsubaki et al. | |
| 2011/0287234 A1 * | 11/2011 | Tsuchihashi et al. ....... 428/195.1 |
| 2011/0318691 A1 * | 12/2011 | Tsuchimura et al. ....... 430/285.1 |
| 2012/0058436 A1 | 3/2012 | Tsubaki et al. | |
| 2012/0251953 A1 * | 10/2012 | Robinson et al. ........... 430/285.1 |
| 2012/0315449 A1 | 12/2012 | Tsubaki et al. | |

FOREIGN PATENT DOCUMENTS

| | | |
|---|---|---|
| JP | 11-109613 A | 4/1999 |
| JP | 11-143074 A | 5/1999 |
| JP | 11-258796 A | 9/1999 |
| JP | 2005-266798 A | 9/2005 |
| JP | 2006-227398 A | 8/2006 |
| JP | 2008-33102 A | 2/2008 |
| JP | 2008-513820 A | 5/2008 |
| JP | 2008-292975 A | 12/2008 |
| JP | 2009-134020 A | 6/2009 |

(Continued)

OTHER PUBLICATIONS

International Search Report (PCT/ISA/210) dated Oct. 18, 2011, issued by the International Searching Authority in International Application No. PCT/JP2011/070623.
Written Opinion (PCT/ISA/237) dated Oct. 18, 2011, issued by the International Searching Authority, in International Application No. PCT/JP2011/070623.
Office Action dated Aug. 19, 2014, issued by the Japanese Patent Office in counterpart Japanese Patent Application No. 2011/197410.

(Continued)

*Primary Examiner* — Amanda C Walke
(74) *Attorney, Agent, or Firm* — Sughrue Mion, PLLC

(57) ABSTRACT

Provided is a negative type pattern forming method that satisfies high sensitivity, high resolution, good roughness and good dry etching resistance at the same time, and further, has a good development time dependency, the method including (i) forming a film by a chemical amplification resist composition containing (A) a fullerene derivative having an acid-decomposable group, (B) a compound generating an acid upon irradiation with an actinic ray or radiation, and (C) a solvent, (ii) exposing the film, and (iii) developing the exposed film by using an organic solvent-containing developer.

17 Claims, No Drawings

(56) References Cited

FOREIGN PATENT DOCUMENTS

| | | |
|---|---|---|
| JP | 2010-24221 A | 2/2010 |
| JP | 2010-116380 A | 5/2010 |
| JP | 2011-28201 A | 2/2011 |
| WO | 2004/012012 A1 | 2/2004 |
| WO | WO 2006030234 A3 * | 9/2006 |
| WO | 2008/153110 A1 | 12/2008 |
| WO | WO 2011061501 A2 * | 5/2011 |

* cited by examiner

PATTERN FORMING METHOD, CHEMICAL AMPLIFICATION RESIST COMPOSITION AND RESIST FILM

CROSS REFERENCE TO RELATED APPLICATIONS

This is a continuation of International Application No. PCT/JP2011/070623 filed Sep. 9, 2011, and claims priority from Japanese Patent Application No. 2010-208625 filed Sep. 16, 2010, the contents of all of which are incorporated herein by reference.

TECHNICAL FIELD

The present invention relates to a pattern forming method using a developer containing an organic solvent used suitably in a super micro lithography process such as manufacturing of a super LSI or high capacity microchip and other photo-fabrication process, a chemical amplification resist composition for use in the pattern forming method, and a resist film. Further, the present invention relates to a pattern forming method using a developer containing an organic solvent which can be used suitably in micromachining of a semiconductor device with an electron beam or EUV ray (wavelength: near 13 nm), a resist film, a chemical amplification resist composition for use in the pattern forming method and a resist film. Still further, a pattern forming method of the present invention relates to a pattern forming method which can also be used suitably in fabrication of a photomask or a mold structure for nano-imprinting a chemical amplification resist composition for use in the pattern forming method and a resist film.

BACKGROUND ART

A micromachining by a lithography using a photoresist composition has been conducted in a conventional manufacturing process of a semiconductor device such as an IC or LSI. Recently, an ultrafine pattern formation of a submicron region or a quarter micron region has been required as an integration level of an integrated circuit becomes higher. Accordingly, an exposure wavelength has a tendency to become shorter from g line to i line, and further to a KrF excimer laser ray. Furthermore, development of a lithography using an electron beam or X-ray or EUV ray other than the excimer laser ray is progressing.

These electron beam or X-ray or EUV ray lithography takes a seat as a pattern formation technique of the next generation or the next of the next generation, and a resist composition of a high sensitivity and high resolution is desired. Particularly, a high sensitization is very important problem to be solved for shortening of a processing time of wafer. However, when intending to a high sensitization, a resolution represented by a limiting resolution line width is reduced, so that development of a resist composition satisfying such characteristics is strongly desired.

The high sensitivity and the high resolution are in a relationship of tradeoff therebetween and thus it is very important how to satisfy them at the same time. As an actnic ray-sensitive or radiation-sensitive resin composition, there is a "positive type" actnic ray-sensitive or radiation-sensitive resin composition in which a resin poorly water-soluble or insoluble to an alkali developer is used to solubilize an exposed portion by a radiation exposure to form a pattern, and a "negative type" actnic ray-sensitive or radiation-sensitive resin composition in which a resin soluble to an alkali developer is used to make an exposed portion to be a poorly water-soluble or insoluble by a radiation exposure to form a pattern.

For the actnic ray-sensitive or radiation-sensitive resin composition suitable for such a lithography process using an electron beam, X-ray or EUV-ray, consideration is made mainly on a chemically amplified positive type resist composition using acid catalyzed reaction from the viewpoint of a high sensitization, and a chemical amplification type positive resist composition containing a phenolic resin (hereinafter, also referred to as a phenolic acid-decomposable resin), as a main component, which is insoluble or sparingly soluble in an alkali developer and becomes soluble by the action of an acid and an acid generator is effectively used.

In the meantime, forming a pattern that has various shapes such as a line, a trench, or a hole is requested in manufacturing a semiconductor device and the like. In order to satisfy the request for the formation of the pattern having various shapes, positive type as well as negative type actnic ray-sensitive or radiation-sensitive resin compositions have been developed, but a reduction of resolution is required in an ultrafine pattern formation. To solve such a problem, a method of developing a film obtained from an acid-decomposable resin with a developer other than an alkali developer is proposed (see, Patent Document 1).

Further, a method is known in which a film obtained from an electron beam resist containing a fullerene derivative is exposed, and subsequently, developed with the organic solvent to form a negative type pattern for the purpose of improving a dry etching resistance, resolution and sensitivity (see, for example, Patent Documents 2 and 3).

As other techniques in which a fullerene or the fullerene derivative is used in the resist composition, a method is also known in which a film is formed using a resist composition which contains a methanofullerene derivative having a specific structure, a photo-acid generator and a crosslinking agent, and an acid crosslinking reaction is performed by exposing the formed film, and then the film is developed with the organic solvent to form a negative type pattern (see, for example, Patent Document 4), or a method is known in which a film is formed using a resist composition formed by adding a predetermined amount of a fullerene derivative to a main chain scission type resist composition, the film is exposed, and then developed with the organic solvent to form a pattern (see, for example, Patent Document 5).

Further, in Patent Document 6, fullerene hydroxide exhibiting a high solubility in an ester solvent such as propylene glycol-1-monomethyl acetate (PGMEA) is disclosed as well as an application to a use of photoresist is suggested.

However, at present circumstances, a technique that can satisfy high sensitivity, high resolution, good roughness and good dry etching resistance at the same time is required.

RELATED ART

Patent Document

Patent Document 1: Japanese Patent Application Laid-Open No. 2008292975
Patent Document 2: Japanese Patent Application Laid-Open No. H11-143074
Patent Document 3: Japanese Patent Application Laid-Open No. H11-258796
Patent Document 4: Japanese Patent Application Laid-Open No. 2008-513820
Patent Document 5: Japanese Patent Application Laid-Open No. 2009-134020

Patent Document 6: Japanese Patent Application Laid-Open No. 2010-116380

DISCLOSURE OF INVENTION

Problems to be Solved by the Invention

The present invention has been made in an effort to solve the problems described above and intends to provide a pattern forming method, a chemical amplification resist composition and a resist film that satisfies high sensitivity, high resolution, good roughness and good dry etching resistance at the same time, and further, has a good development time dependency.

Means for Solving the Problems

The present invention has the following configuration, and accordingly, the above-mentioned object of the present invention is achieved.

That is, the above-mentioned problems may be solved by the following means.

[1] A negative type pattern forming method including:

(i) forming a film by a chemical amplification resist composition containing (A) a fullerene derivative having an acid-decomposable group, (B) a compound generating an acid upon irradiation with an actinic ray or radiation, and (C) a solvent, (ii) exposing the film, and (iii) developing the exposed film by using an organic solvent-containing developer.

[2] The negative type pattern forming method of [1], in which the content of the organic solvent in the organic solvent-containing developer is 90% by mass to 100% by mass based on the total amount of the developer.

[3] The negative type pattern forming method of [1] or [2], in which the content of the fullerene derivative (A) is 30% by mass to 99% by mass based on the total solid of the resist composition.

[4] The negative type pattern forming method of any one of [1] to [3], in which the compound (B) is a compound generating sulfonic acid represented by the following Formula (BI) or Formula (I) upon irradiation with an actinic ray or radiation.

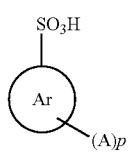
(BI)

In Formula (BI),

Ar represents an aromatic ring.

p represents an integer of 0 or more.

A represents a group having a hydrocarbon group.

When p is 2 or more, each A may be the same as or different from every other A.

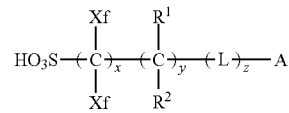
(I)

In the formula, each Xf independently represents a fluorine atom or an alkyl group substituted with at least one fluorine atom.

Each of $R^1$ and $R^2$ independently represents a group selected from a hydrogen atom, a fluorine atom and an alkyl group, and when a plurality of $R^1$ and $R^2$ are present, each of $R^1$ and $R^2$ may be the same as or different from every other $R^1$ and $R^2$.

L represents a divalent linking group, and when a plurality of L are present, each L may be the same as or different from every other L.

A represents a cyclic organic group.

x represents an integer of 1 to 20, y represents an integer of 0 to 10, and z represents an integer of 0 to 10.

[5] The negative type pattern forming method of any one of [1] to [4], in which the fullerene derivative (A) has a partial structure represented by the following Formula (a1) or Formula (a2).

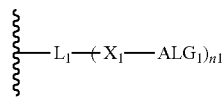
(a1)

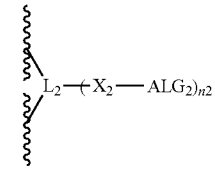
(a2)

In the formula, each of $ALG_1$ and $ALG_2$ independently represents a group capable of leaving by the action of an acid. When n1 is an integer of 2 or more, each $ALG_1$ may be bound with each other. When n2 is an integer of 2 or more, each $ALG_2$ may be bound with each other.

$L_1$ represents a single bond or an (n1+1)-valent linking group bound to one of carbon atoms forming a fullerene structure.

$L_2$ represents an (n2+2)-valent linking group bound to two of carbon atoms forming a fullerene structure.

Each of $X_1$ and $X_2$ independently represents —O— or —COO—.

Each of n1 and n2 independently represents an integer of 1 to 6.

[6] The negative type pattern forming method of any one of [1] to [5], in which the acid-decomposable group is a structure protected by a leaving group in which an alcoholic hydroxyl group is capable of decomposing and leaving by the action of an acid.

[7] The negative type pattern forming method of any one of [1] to [6], in which the developer is a developer containing at least one organic solvent selected from the group consisting of a ketone-based solvent, an ester-based solvent, an alcohol-based solvent, an amide-based solvent and an ether-based solvent.

[8] The negative type pattern forming method of any one of [1] to [7] further including (iv) washing with a rinse liquid containing an organic solvent.

[9] A chemical amplification resist composition for use in the negative type pattern forming method of any one of [1] to [8].

[10] A chemical amplification resist composition containing (A) a fullerene derivative having an acid-decomposable group, (B) a compound generating an acid upon irradiation with an actinic ray or radiation, and (C) a solvent, in which the compound (B) is a compound generating sulfonic acid represented by the following Formula (BI) or Formula (I) upon irradiation with an actinic ray or radiation.

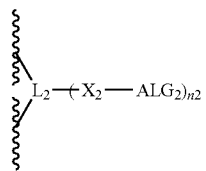

In Formula (BI),

Ar represents an aromatic ring.

p represents an integer of 0 or more.

A represents a group having a hydrocarbon group.

When p is 2 or more, each A may be the same as or different from every other A.

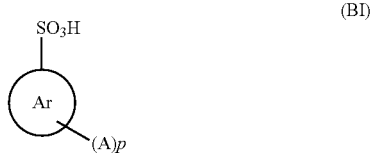

In the formula, each Xf independently represents a fluorine atom or an alkyl group substituted with at least one fluorine atom.

Each of $R^1$ and $R^2$ independently represents a group selected from a hydrogen atom, a fluorine atom and an alkyl group, and when a plurality of $R^1$ and $R^2$ are present, each of $R^1$ and $R^2$ may be the same as or different from every other $R^1$ and $R^2$.

L represents a divalent linking group, and when a plurality of L are present, each L may be the same as or different from every other L.

A represents a cyclic organic group.

x represents an integer of 1 to 20, y represents an integer of 0 to 10, and z represents an integer of 0 to 10.

[11] The chemical amplification resist composition of [9] or [10], in which the fullerene derivative (A) has a partial structure represented by the following Formula (a1) or Formula (a2).

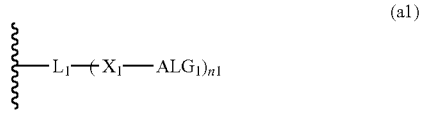

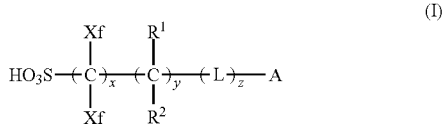

In the formula, each of $ALG_1$ and $ALG_2$ independently represents a group capable of leaving by the action of an acid. When n1 is an integer of 2 or more, each $ALG_1$ may be bound with each other. When n2 is an integer of 2 or more, each $ALG_2$ may be bound with each other.

$L_1$ represents a single bond or an (n1+1)-valent linking group bound to one of carbon atoms forming a fullerene structure.

$L_2$ represents an (n2+2)-valent linking group bound to two of carbon atoms forming a fullerene structure.

Each of $X_1$ and $X_2$ independently represents —O— or —COO—.

Each of n1 and n2 independently represents an integer of 1 to 6.

[12] The chemical amplification resist composition of any one of [9] to [11], in which the acid-decomposable group has a structure protected by a leaving group in which an alcoholic hydroxyl group is capable of decomposing and leaving by the action of an acid.

[13] A resist film formed by the chemical amplification resist composition of any one of [9] to [12].

Further, the present invention preferably has the following configuration.

[14] The pattern forming method of any one of [1] to [8], in which the water content of the organic solvent-containing developer is less than 10% by mass based on the total developer.

[15] The pattern forming method of any one of [1] to [8] and [14], in which the developer does not substantially contain water.

[16] The pattern forming method of any one of [1] to [8], in which the resist composition does not contain a crosslinking agent capable of crosslinking the fullerene derivatives by the action of an acid.

[17] The chemical amplification resist composition of any one of [9] to [12], in which the resist composition does not contain a crosslinking agent capable of crosslinking the fullerene derivatives by the action of an acid.

Effects of the Invention

According to the present invention, it is possible to provide a pattern forming method, a chemical amplification resist composition and a resist film that satisfies high sensitivity, high resolution, good roughness and good dry etching resistance at the same time, and further, has a good development time dependency.

EMBODIMENTS FOR CARRYING OUT THE INVENTION

Hereinafter, embodiments for carrying out the present invention will be described.

Meanwhile, the description of a group (atomic group) in the present specification includes a group having no substituent and a group having a substituent. For example, "an alkyl group" includes not only an alkyl group having no substituent (unsubstituted alkyl group) but also an alkyl group having a substituent (substituted alkyl group).

In the present specification, the term "actinic ray" or "radiation" indicates, for example, a bright line spectrum of mercury lamp, a far ultraviolet ray typified by excimer laser, an extreme-ultraviolet ray (EUV light), an X-ray, an electron beam or the like. Also, in the present invention, the "light" means an actinic ray or radiation.

Further, In the present invention, unless otherwise indicated, the "exposure" includes not only exposure with a mercury lamp, a far ultraviolet ray typified by excimer laser, an X-ray, EUV light or the like but also lithography with a particle beam such as electron beam and ion beam.

The chemical amplification resist composition of the present invention contains (A) a resin substantially insoluble in alkali, (B) a compound capable of generating an acid upon irradiation with an actinic ray or radiation, (C) a crosslinking agent, and (D) a solvent.

The pattern forming method of the present invention is a negative type pattern forming method including (i) forming a film by a chemical amplification resist composition containing (A) a fullerene derivative having an acid-decomposable group, (B) a compound generating an acid upon irradiation with an actinic ray or radiation, and (C) a solvent, (ii) exposing the film, and (iii) developing the exposed film by using an organic solvent-containing developer.

Fullerene is generally insoluble or sparingly soluble in an organic solvent because of a strong interaction between fullerene molecules and a high density of fullerene molecules.

However, according to the pattern forming method of the present invention, since introduction of an acid-decomposable group into fullerene reduces the interaction between fullerene molecules in unexposed portions, thereby lowering the density of fullerene molecules, the dissolution rate in the developer containing an organic solvent is increased, and thus, the unexposed portions become soluble in the developer.

Meanwhile, in exposed portions, since a leaving group in the compound (B) is left from fullerene molecules by the action of an acid generated by exposure, the interaction between fullerene molecules is enhanced, and thus, the dissolution rate in the developer is considerably decreased. As a result, the exposed portions become insoluble or sparingly soluble in the developer containing an organic solvent.

By such a mechanism, according to the pattern forming method of the present invention, it is assumed that a negative type pattern is formed by development using a developer containing an organic solvent However, in a microfabrication of semiconductor devices using an electron beam or EUV light, the line width of patterns is short, and thus, a problem such as pattern collapse is prone to occur unless the thickness of a resist film is reduced accordingly.

However, if the thickness of the resist film is reduced, another problem arises this time in that an etching resistance is deteriorated.

The film in the pattern forming method of the present invention has a very high etching resistance is very high due to the presence of a fullerene structure of a fullerene derivative. Further, as described above, it is assumed that the enhanced density of fullerene derivatives due to the enhanced interaction between fullerene molecules also contributes to enhancement in etching resistance.

Accordingly, in the present invention, although the thickness of a resist film is reduced in order to suppress a problem of pattern collapse, an excellent etching resistance can be obtained.

Further, as the film becomes thinner, the exposure, particularly, in a film thickness direction becomes more assured, thereby making the sensitivity, resolution and roughness performances excellent.

Meanwhile, in the case where the acid-decomposable group in the fullerene derivative (A) has, for example, a structure protected by a leaving group in which an alkali-soluble group is capable of decomposing and leaving by the action of an acid, there is a possibility of forming a positive pattern by using an alkaline developer instead of an organic solvent-containing developer. However, even though the fullerene derivative has an alkali-soluble group by acid decomposition, it is difficult to dissolve exposed portions in the alkaline developer because of the presence of the fullerene structure. Accordingly, it is hard to obtain a pattern having excellent sensitivity, resolution and roughness performances.

Furthermore, in the case of the positive pattern forming method, since the enhancement in interaction between fullerene molecules as described above does not occurs in unexposed portions, it is also difficult to enhance the etching resistance as in the present invention.

Accordingly, from the viewpoint of enhancing the etching resistance, in the resist film remained after development (exposed portion in a negative type pattern), it is preferred to enhance the density of the fullerene derivatives in the film after development by making the level of the interaction between fullerene derivative molecules close to the level of a very strong interaction between unmodified fullerene molecules as possible.

For that reason, in the present invention, it is preferred that the fullerene derivative has no crosslinkable group capable of crosslinking with other fullerene derivatives in the presence or absence of a crosslinking agent, other than an acid-decomposable group. Further, it is preferred that the chemical amplification resist composition in the present invention has no crosslinking agent capable of crosslinking fullerene derivatives by the action of an acid.

The reason is that, if the fullerene derivatives are crosslinked with each other by a crosslinking component and the like, the approach of the fullerene structures to each other is suppressed, thereby intervening the enhancement in density of the fullerene derivatives.

In the pattern forming method of the present invention, the developer is preferably a developer containing at least one organic solvent selected from the group consisting of a ketone-based solvent, an ester-based solvent, an alcohol-based solvent, an amide-based solvent and an ether-based solvent.

It is preferred that the pattern forming method of the present invention further includes (iv) washing with a rinse liquid containing an organic solvent.

The rinse liquid is preferably a rinse liquid containing at least one organic solvent selected from the group consisting of a ketone-based solvent, an ester-based solvent, an alcohol-based solvent, an amide-based solvent and an ether-based solvent.

The pattern forming method of the present invention preferably includes (v) heating after (ii) exposing.

The pattern forming method of the present invention may include (ii) exposing several times.

The pattern forming method of the present invention may include (v) heating several times.

The resist film of the present invention is a film formed by the chemically amplified resist composition, for example, a film formed by applying the resist composition on a substrate.

Hereinafter, the resist composition which can be used in the present invention will be described.

[1] Fullerene Derivative Having an Acid-Decomposable Group

The term "fullerene" in the fullerene derivative used in the resist composition of the present invention (hereinafter, simply referred to as fullerene derivative (A)) refers to a carbon cluster having a closed shell structure. The carbon number of fullerenes is generally an even number of 60 to 130.

Specific examples of fullerene include $C_{60}$, $C_{70}$, $C_{76}$, $C_{78}$, $C_{82}$, $C_{84}$, $C_{90}$, $C_{94}$, $C_{96}$ and higher carbon clusters having more carbons than them. Herein, a fullerene structure indicates a structure constituting a closed shell structure of the fullerene, and refers to a closed shell carbon structure constituted only with carbon atoms.

The fullerene structure possessed by the fullerene derivative (A) is not limited, but among them, fullerene $C_{60}$ or fullerene $C_{70}$ is preferred, and fullerene $C_{60}$ is more preferred. Since fullerene $C_{60}$ and fullerene $C_{70}$ are advantageous from the viewpoint of easy availability because they are obtained as main products in the preparation of fullerene. That is, the fullerene derivative of the present invention is preferably a derivative of fullerene $C_{60}$ or fullerene $C_{70}$, and more preferably a derivative of fullerene $C_{70}$.

Further, the fullerene derivative (A) includes a derivative that includes, for example, metal, compounds and the like inside the fullerene structure and a derivative that forms a complex with other metal atoms, compounds and the like.

The fullerene derivative used in the resist composition of the present invention has an acid-decomposable group. More particularly, the fullerene derivative is preferably composed by forming a partial structure having an acid-decomposable group on the surface of fullerene.

The number of the acid-decomposable group is generally 2 or more, preferably 3 or more, still more preferably 4 or more, and generally 30 or less, preferably 20 or less, still more preferably 10 or less.

Here, the acid-decomposable group is not particularly limited as long as the group has a structure generating a group capable of decomposing and leaving by the action of an acid, but it is preferred to have a structure protected by a leaving group in which a polar group is decomposed and left by the action of an acid.

The polar group is not particularly limited, but may include an alcoholic hydroxyl group, a phenolic hydroxyl group, a carboxyl group, a fluorinated alcohol group (preferably a hexafluoroisopropanol group), a sulfonate group, a sulfonamide group, a sulfonylimide group, a (alkylsulfonyl)(alkylcarbonyl)methylene group, a (alkylsulfonyl)(alkylcarbonyl) imide group, a bis(alkylcarbonyl)methylene group, a bis(alkylcarbonyl)imide group, a bis(alkylsulfonyl)methylene group, a bis(alkylsulfonyl)imide group, a tris(alkylcarbonyl) methylene group, a tris(alkylsulfonyl)methylene group and the like.

Examples of preferred polar groups include an alcoholic hydroxyl group, a carboxyl group, a fluorinated alcohol group (preferably a hexafluoroisopropanol group) and a sulfonate group, and an alcoholic hydroxyl group is more preferred.

The fullerene derivative (A) preferably has a partial structure represented by the following Formula (a1) or Formula (a2), containing an acid-decomposable group.

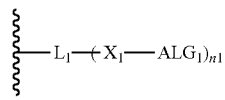

(a1)

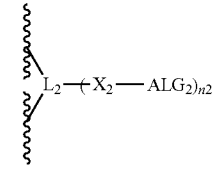

(a2)

In the formula, each of $ALG_1$ and $ALG_2$ independently represents a group capable of leaving by the action of an acid (leaving group). When n1 is an integer of 2 or more, each $ALG_1$ may be bound with each other. When n2 is an integer of 2 or more, each $ALG_2$ may be bound with each other.

$L_1$ represents a single bond or an (n1+1)-valent linking group bound to one of carbon atoms forming a fullerene structure.

$L_Z$ represents an (n2+2)-valent linking group bound to two of carbon atoms forming a fullerene structure.

Each of $X_1$ and $X_2$ independently represents —O— or —COO—.

Each of n1 and n2 independently represents an integer of 1 to 6.

When n1 is 1, the divalent linking group as $L_1$ may include —COO—, —COO—, —CO—, —CS—, —O—, —S—, —SO—, —SO$_2$—, —NR— (R is a hydrogen atom or an alkyl group), an alkylene group, an alkenylene group, a cycloalkylene group, a cycloalkenylene group, a divalent nitrogen-containing non-aromatic heterocyclic group, a divalent aromatic ring group or a group to which two or more of the above-mentioned groups are linked, and preferably a linking group having a total carbon number of 12 or less.

In —NR—, the alkyl group represented by R may include an alkyl group having 20 or less carbon atoms, such as a methyl group, an ethyl group, a propyl group, an isopropyl group, an n-butyl group, a sec-butyl group, a hexyl group, a 2-ethylhexyl group, an octyl group and a dodecyl group, more preferably an alkyl group having 8 or less carbon atoms, and particularly preferably an alkyl group having 3 or less carbon atoms. R is particularly preferably a hydrogen atom, a methyl group or an ethyl group.

In $L_1$, the alkylene group may be either straight or branched, and preferred examples thereof may include an alkylene group having 1 to 8 carbon atoms such as a methylene group, an ethylene group, a propylene group, a butylene group, a hexylene group and an octylene group. An alkylene group having 1 to 6 carbon atoms is more preferred, and an alkylene group having 1 to 4 carbon atoms is particularly preferred.

The alkenylene group in $L_1$ may include a group having a double bond at any position of the alkylene group as described above.

The cycloalkylene group in $L_1$ may be monocyclic or polycyclic, and preferred examples thereof may include a divalent aliphatic hydrocarbon ring group having 3 to 17 carbon atoms such as a cyclobutylene group, a cyclopentylene group, a cyclohexylene group, a norbornanylene group, an adamantylene group and a diadamantanylene group. A divalent aliphatic hydrocarbon ring group having 5 to 12 carbon atoms is more preferred, and a divalent aliphatic hydrocarbon ring group having 6 to 10 carbon atoms is particularly preferred.

The cycloalkenylene group in $L_1$ may include a group having a double bond at any position of the cycloalkylene group as described above.

The divalent nitrogen-containing non-aromatic heterocyclic group in $L_1$ refers to preferably a 3- to 8-membered non-aromatic heterocyclic group having at least one nitrogen atom, and specifically, may include a divalent linking group having the following structure.

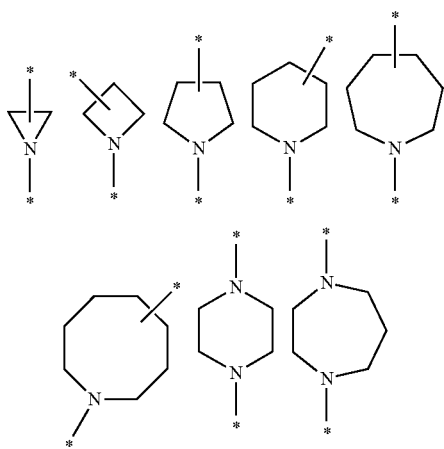

The divalent aromatic ring group in $L_1$ may include an arylene group having 6 to 14 carbon atoms which may have a substituent, such as a phenylene group, a tolylene group and a naphthylene group, or a divalent aromatic ring group containing a heterocycle such as thiophene, furan, pyrrole, benzothiophene, benzofuran, benzopyrrole, triazine, imidazole, benzimidazole, triazole, thiadiazole and thiazole.

The alkyl group in the alkylene group, the alkenylene group, the cycloalkylene group, the cycloalkenylene group, the divalent nitrogen-containing non-aromatic heterocyclic group and the divalent aromatic ring group and as R in —NR—, in $L_1$, may further have a substituent, and examples of the further substituent may include a hydroxyl group, a halogen atom (a fluorine atom, a chlorine atom, a bromine atom, an iodine atom and the like), a nitro group, a cyano group, an amide group, a sulfonamide group, an alkyl group such as a methyl group, an ethyl group, a propyl group, an n-butyl group, a sec-butyl group, a hexyl group, a 2-ethylhexyl group and an octyl group, an alkoxy group such as a methoxy group, an ethoxy group, a hydroxyethoxy group, a propoxy group, a hydroxypropoxy group and a butoxy group, an alkoxycarbonyl group such as a methoxycarbonyl group and an ethoxycarbonyl group, an acyl group such as a formyl group, an acetyl group and a benzoyl group, an acyloxy group such as an acetoxy group and a butyryloxy group, and a carboxyl group.

When n1 is an integer of 2 or more, specific examples of the (n1+1)-valent linking group of $L_1$ may include a group formed by removing any (n1-1) hydrogen atoms from the divalent group as specifically exemplified as $L_1$ above.

Specific examples of the (n2+2)-valent linking group in $L_2$ may include a group formed by removing any n2 hydrogen atoms from the divalent group as specifically exemplified as $L_1$ above.

When $X_1$ and $X_2$ are —COO—, the partial structures represented by Formula (a1) and Formula (a2) are structures which are decomposed by the action of an acid to produce a carboxyl group. In this case, it is preferred that each of $ALG_1$ and $ALG_2$ is independently a group represented by —C(Rx$_1$)(Rx$_2$)(Rx$_3$).

In the formula, each of $Rx_1$ to $Rx_3$ independently represents a monovalent organic group.

$Rx_1$ and $Rx_2$ may be bound with each other to form a ring.

The monovalent organic group as $Rx_1$ to $Rx_3$ is preferably a (straight or branched) alkyl group or a (monocyclic or polycyclic) cycloalkyl group.

The alkyl group of $Rx_1$ to $Rx_3$ is preferably an alkyl group having 1 to 4 carbon atoms such as a methyl group, an ethyl group, a n-propyl group, an isopropyl group, an n-butyl group, an isobutyl group and a t-butyl group.

The cycloalkyl group of $Rx_1$ to $Rx_3$ is preferably a monocyclic cycloalkyl group having 3 to 20 carbon atoms such as a cyclopentyl group and a cyclohexyl group, or a polycyclic cycloalkyl group such as a norbornyl group, a tetracyclodecanyl group, a tetracyclododecanyl group and an adamantyl group.

The ring formed by $Rx_1$ and $Rx_2$ bound with each other is preferably a (monocyclic or polycyclic) cycloalkyl group. The cycloalkyl group is preferably a monocyclic cycloalkyl group such as a cyclopentyl group and cyclohexyl group, or a polycyclic cycloalkyl group such as a norbornyl group, a tetracyclodecanyl group, a tetracyclododecanyl group and an adamantyl group. a monocyclic cycloalkyl group having 5 or 6 carbon atoms is more preferred, and a cyclohexyl group is particularly preferred.

An aspect in which $Rx_1$ is a methyl group or an ethyl group, and $Rx_2$ and $Rx_3$ are combined to form the cycloalkyl group as described above is preferred.

$Rx_1$ to $Rx_3$ may further have a substituent, and examples of the substituent may include an alkyl group (having 1 to 4 carbon atoms), a halogen atom, a hydroxyl group, an alkoxy group (having 1 to 4 carbon atoms), a carboxyl group, an alkoxycarbonyl group (having 2 to 6 carbon atoms), an aryl group (having 6 to 10 carbon atoms) and the like, and a group having 8 or less carbon atoms is preferred.

When $X_1$ and $X_2$ is —O—, the partial structures represented by Formula (a1) and Formula (a2) are structures which are decomposed by the action of an acid to produce a hydroxyl group. In this case, it is preferred that each of $ALG_1$ and $ALG_2$ is independently a group represented by —C(Rx$_4$)$_2$ORx$_5$, a group represented by —C(=O)OC(Rx$_4'$)(Rx$_5'$)$_2$ or a group represented by —C(Rx$_6$)$_3$.

Each $Rx_4$ independently represents a hydrogen atom or a monovalent organic group. $Rx_4$ may be bound with each other to form a ring.

$Rx_5$ represents a monovalent organic group. $Rx_4$ and $Rx_5$ may be bound with each other to form a ring.

$Rx_4'$ represents a hydrogen atom or a monovalent organic group.

Each $Rx_5'$ independently represents a monovalent organic group. $Rx_5'$ may be bound with each other to form a ring. Further, one $Rx_5'$ and $Rx_4'$ may be bound with each other to form a ring.

Each $Rx_6$ independently represents a hydrogen atom, alkyl group, a cycloalkyl group, aryl group, an alkenyl group or an alkynyl group. Two $Rx_6$ may be bound with each other to form a ring. However, when one or two of three $Rx_6$ is a hydrogen atom, at least one of the remaining $Rx_6$ represents an aryl group, an alkenyl group or an alkynyl group.

Each of $Rx_4$ and $Rx_4'$ independently represents, as described above, a hydrogen atom or a monovalent organic group. Each of $Rx_4$ and $Rx_4'$ is independently preferably a hydrogen atom, an alkyl group or a cycloalkyl group, and more preferably a hydrogen atom or an alkyl group.

The alkyl group of $Rx_4$ and $Rx_4'$ may be either straight or branched. The alkyl group preferably has 1 to 10 carbon atoms, and more preferably 1 to 3 carbon atoms. Examples of the alkyl group of $Rx_4$ may include a methyl group, an ethyl group, a n-propyl group, an isopropyl group and an n-butyl group.

The cycloalyl group of $Rx_4$ and $Rx_4'$ may be either monocyclic or polycyclic. The cycloalkyl group preferably has 3 to 10 carbon atoms, and more preferably 4 to 8 carbon atoms. Examples of the cycloalkyl group of $Rx_4$ may include a cyclopropyl group, a cyclobutyl group, a cyclopentyl group, cyclohexyl group, a norbornyl group and an adamantyl group.

Further, at least one $Rx_4$ is preferably a monovalent organic group. If such a configuration is adopted, an especially high sensitivity can be achieved.

The alkyl group and the cycloalkyl group as $Rx_4$ and $Rx_4'$ may further have a substituent, and examples of the substituent may include groups as described in the substituent which $Rx_1$ to $Rx_3$ may further have.

Each of $Rx_5$ and $Rx_5'$ independently represents, as described above, a monovalent organic group. Each of $Rx_5$ and $Rx_5'$ is independently preferably an alkyl group or a cycloalkyl group, and more preferably an alkyl group. The alkyl group and the cycloalkyl group may further have a substituent, and examples of the substituent may include groups as described in the substituent which $Rx_1$ to $Rx_3$ may further have.

It is preferred that the alkyl group of $Rx_5$ and $Rx_5'$ has no substituent or has one or more aryl groups as a substituent. The unsubstituted alkyl group preferably has 1 to 20 carbon atoms. The alkyl group moiety in the alkyl group substituted with one or more aryl groups preferably has 1 to 25 carbon atoms.

Specific examples of the alkyl group of $Rx_5$ and $Rx_5'$ may be similarly exemplified by the specific examples of the alkyl group of $Rx_4$ and $Rx_4'$. Further, the aryl group in the alkyl group substituted with one or more aryl groups preferably has 6 to 10 carbon atoms, and specifically, may include a phenyl group and a naphthyl group.

Further, when the cycloalkyl group of $Rx_5$ and $Rx_5'$ has no substituent, the carbon number is preferably 3 to 20.

Specific examples of the cycloalkyl group of $Rx_5$ and $Rx_5'$ may be similarly exemplified by the specific examples of the cycloalkyl group of $Rx_4$ and $Rx_4'$.

$Rx_6$ represents a hydrogen atom, an alkyl group, a cycloalkyl group, an aryl group, an alkenyl group or an alkynyl group. However, when one or two of three $Rx_6$ are a hydrogen atom, at least one of the remaining $Rx_6$ represents an aryl group, an alkenyl group or an alkynyl group. $Rx_6$ is preferably a hydrogen atom or an alkyl group.

The alkyl group, the cycloalkyl group, the aryl group, the alkenyl group and the alkynyl group as $Rx_6$ may further have a substituent, and examples of the subsistent may include groups as described in the substituent which $Rx_1$ to $Rx_3$ may further have.

The alkyl group and the cycloalkyl group as $Rx_6$ may include groups as described in the alkyl group and the cycloalkyl group of $Rx_4$ and $Rx_4'$. Specifically, when the alkyl group has no substituent, the carbon number is preferably 1 to 6, more preferably 1 to 3.

Examples of the aryl group of $Rx_6$ may include an aryl group having 6 to 10 carbon atoms such as a phenyl group and a naphthyl group.

Examples of the alkenyl group of $Rx_6$ may include an alkenyl group having 2 to 5 carbon atoms such as a vinyl group, a propenyl group and an allyl group.

Examples of the alkynyl group as $Rx_6$ may include an alkynyl group having 2 to 5 carbon atoms such as an ethynyl group, a propynyl group and a butynyl group.

When $Rx_4$ and $Rx_5$ are linked to each other to form a ring, it is preferred that one $Rx_4$ and $Rx_5$ are linked to each other to form a ring.

The ring which may be formed by combining two $Rx_4$, two $Rx_5'$, two $Rx_6$, $Rx_4$ and $Rx_5$, and $Rx_5'$ and $Rx_4'$ with each other is preferably a ring as described as the ring in the cycloalkyl group of $Rx_4$ and $Rx_4$.

The acid-decomposable group is preferably a structure protected by a leaving group in which an alcoholic hydroxyl group is decomposed and left by the action of an acid. Accordingly, the tolerance of development conditions can be extended.

Here, an alcoholic hydroxyl group refers to a hydroxyl group bound to a hydrocarbon group, and is not limited as long as the group is other than a hydroxyl group directly bound to an aromatic ring (a phenolic hydroxyl group).

The alcoholic hydroxyl group is preferably a group other than a hydroxyl group in an aliphatic alcohol in which a carbon atom at the α-position (a carbon atom to which a hydroxyl group is bound) is substituted with an electron-withdrawing group (a halogen atom, a cyano group, a nitro group and the like). The hydroxyl group is preferably a primary alcoholic hydroxyl group (a group in which a carbon atom substituted with a hydroxyl group has two hydrogen atom, separately from the hydroxyl group) or a secondary alcoholic hydroxyl group in which no electron-withdrawing groups are bound to the carbon atom substituted with a hydroxyl group.

Namely, this is the case where the fullerene derivative (A) has a partial structure represented by Formula (a1) and a partial structure represented by Formula (a2), and further, in the case of a group generating an alcoholic hydroxyl group by the action of an acid, $X_1$ and $X_2$ represent —O—, and at the same time, $L_1$ and $L_2$ are selected such that each of a partial structure represented by the following Formula (a1-1) and a partial structure represented by the following Formula (a2-1) obtained when the above-mentioned partial structures are acid-decomposed becomes an alcoholic hydroxyl group.

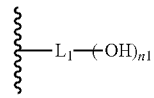

(a1-1)

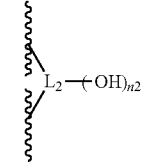

(a2-1)

Further, as one form of the fullerene derivative having an acid-decomposable group in the present invention, a form protected by a leaving group in which a hydroxyl group of fullerene hydroxide is decomposed and left by the action of an acid (that is, in Formula (a1), $L_1$=a single bond, $X_1$=an oxygene atom, n1=1) is also preferred.

Hereinafter, specific examples of the partial structure represented by Formula (a1) are shown, but not limited thereto.

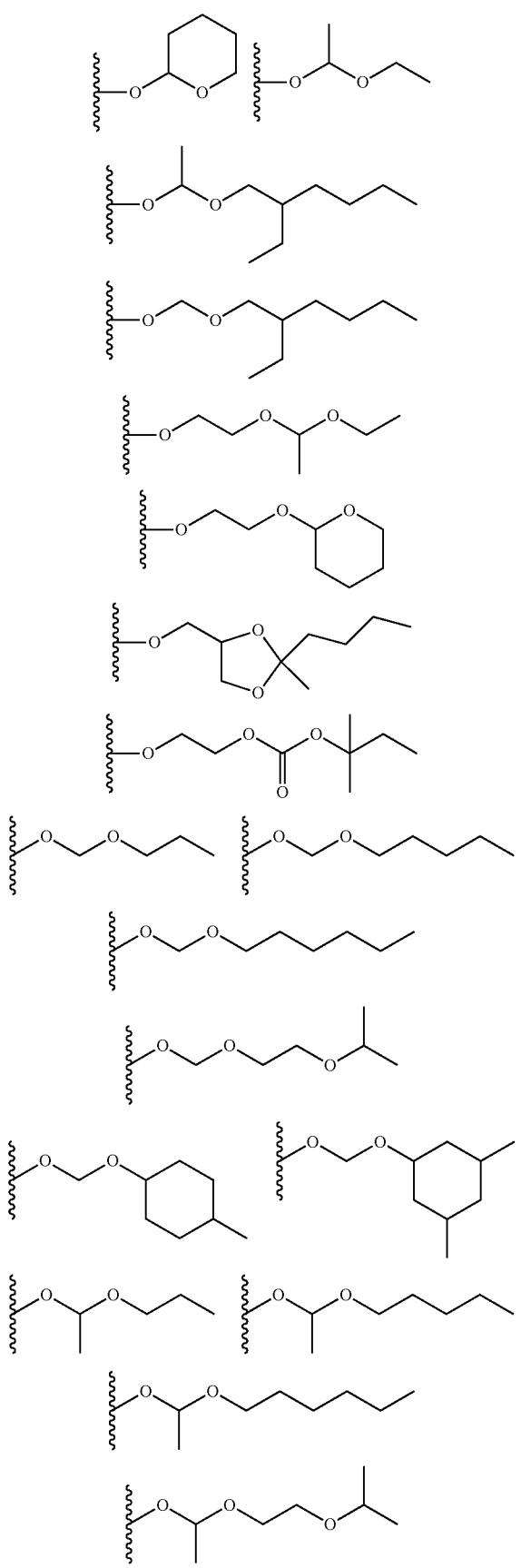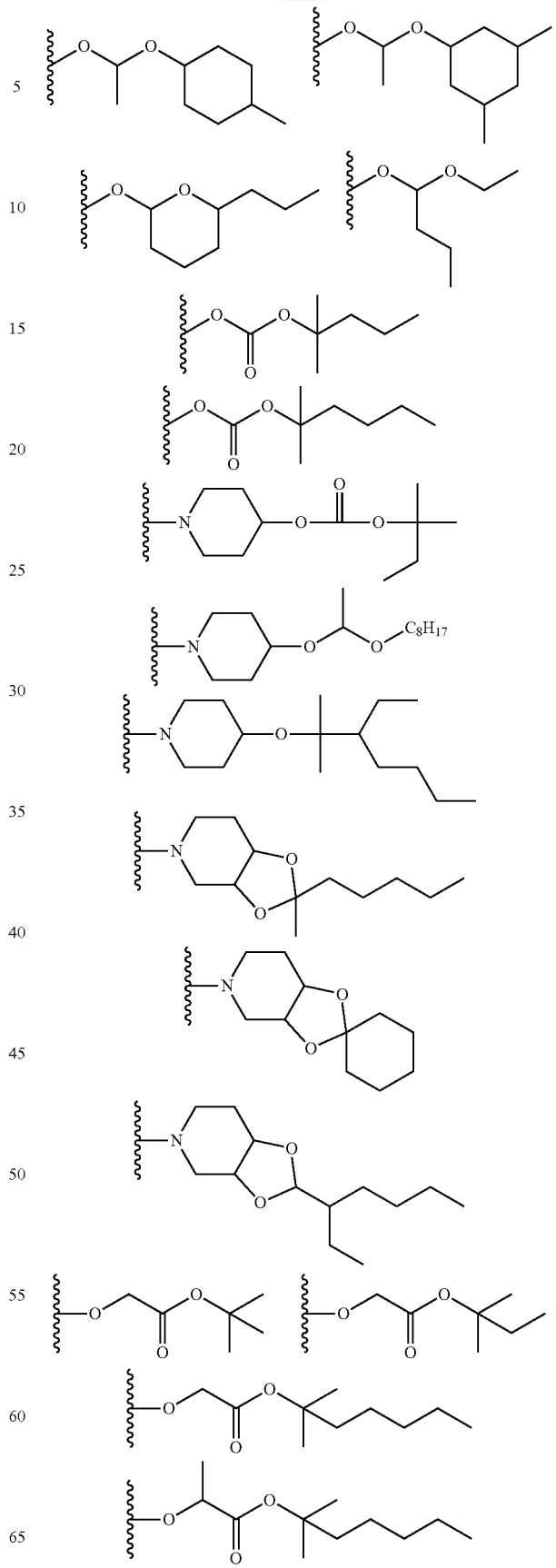

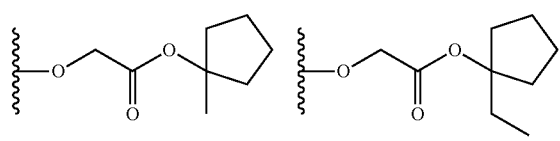
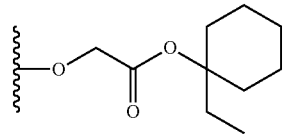
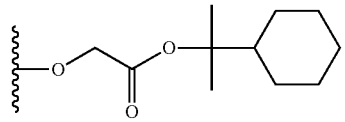
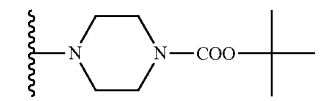
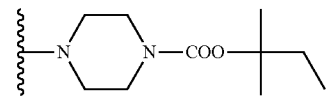
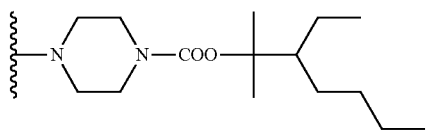
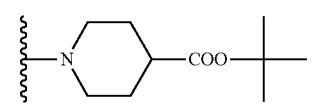
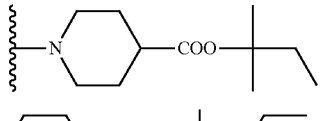
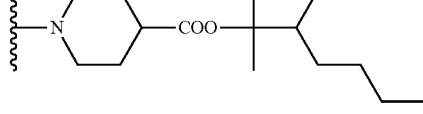
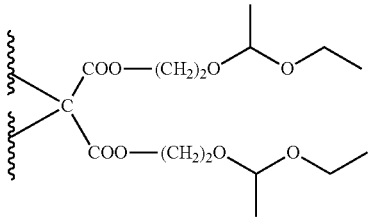
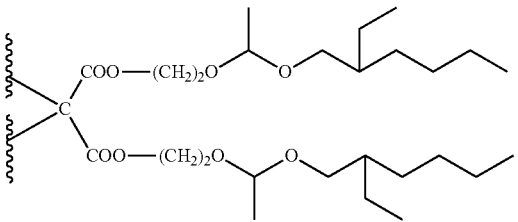
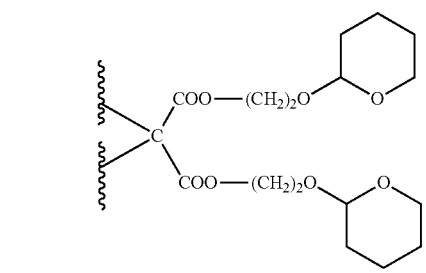
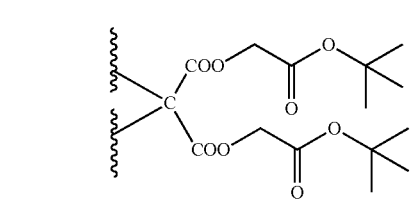
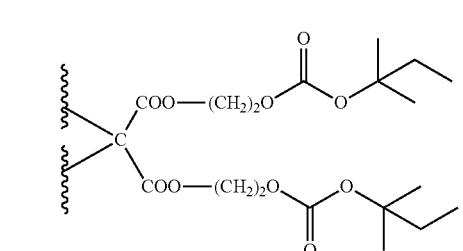
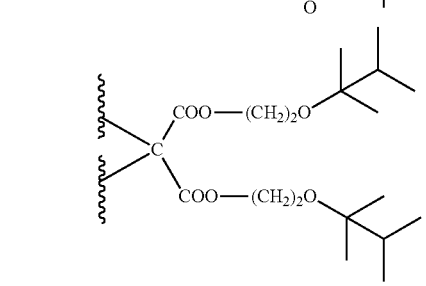
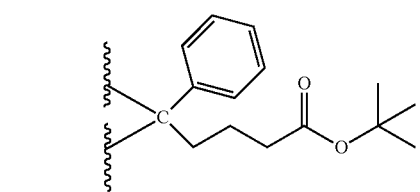
Hereinafter, specific examples of the partial structure represented by Formula (a2) are shown, but not limited thereto.
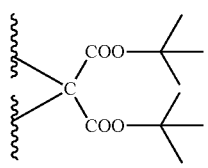
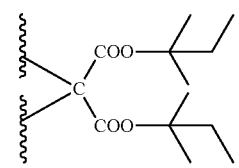
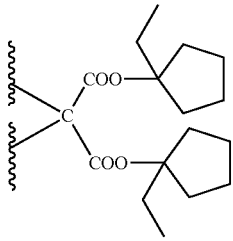
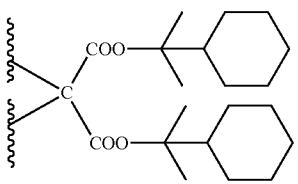

-continued

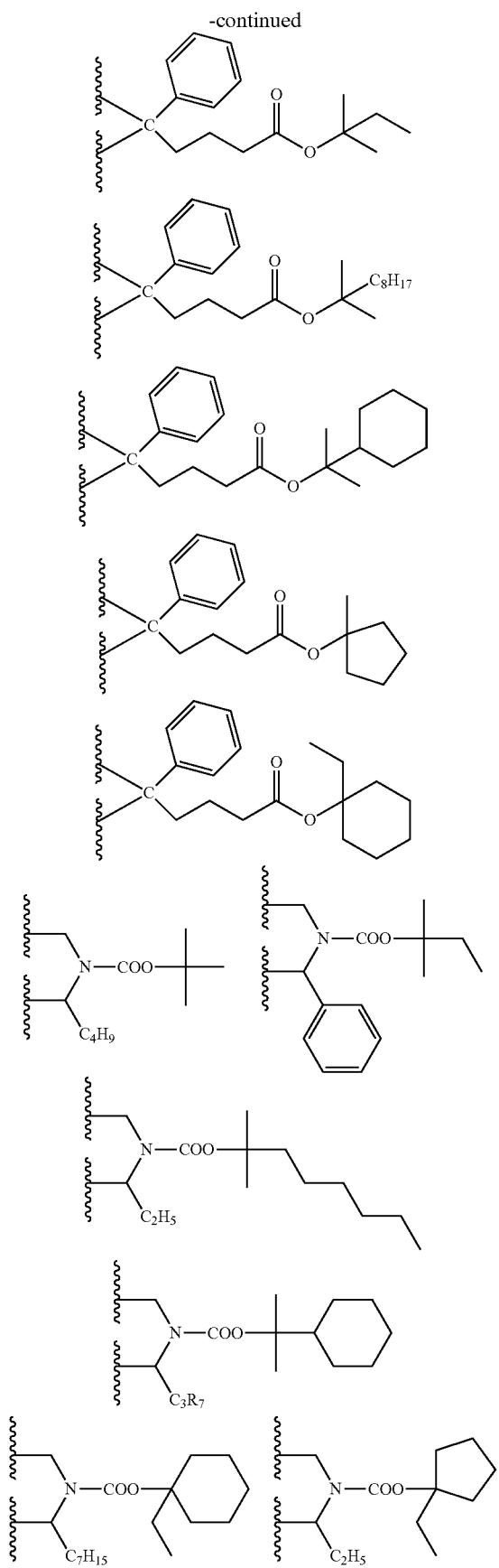

A method for synthesizing the fullerene derivative (A) from fullerene is not particularly limited, but, examples thereof may include (1) a method of etherifying fullerene hydroxide as a raw material by reacting with an etherifying agent corresponding to an acid-decomposable group, (2) a method of esterifying fullerene hydroxide as a raw material by reacting with an esterifying agent corresponding to an acid-decomposable group, (3) a method carbonating fullerene hydroxide as a raw material by reacting with a carbonating agent corresponding to an acid-decomposable group and the like.

Herein, the number of hydroxyl groups in the fullerene hydroxide used in the reaction is generally 2 or more, preferably 4 or more, and more preferably 6 or more, and generally 46 or less, preferably 20 or less, and more preferably 14 or less.

All the hydroxyl groups of fullerene hydroxide may be derived to acid-decomposable groups, or a part of the hydroxyl groups may be derived to acid-decomposable groups.

When a part of the hydroxyl groups is derived to acid-decomposable groups, "the number of acid-decomposable groups:the number of hydroxyl groups" is preferably 100:0 to 20:80, more preferably 90:10 to 30:70, and still more preferably 80:20 to 40:60.

The fullerene derivative (A) may contain two or more kinds of acid-decomposable groups. If such a configuration is adopted, it is possible to finely adjust reactivity and/or developability, thereby facilitating optimization of various performances.

The fullerene derivative (A) may further have a substituent other than acid-decomposable group. Examples of the substituent may include an alkyl group (having 1 to 4 carbon atoms), a halogen atom, a hydroxyl group, an alkoxy group (having 1 to 4 carbon atoms), a carboxyl group, an alkoxycarbonyl group (having 2 to 6 carbon atoms), an aryl group (having 6 to 10 carbon atoms) and the like.

In the resist composition of the present invention, the mixing ratio of the fullerene derivative (A) in the whole composition is preferably 30% by mass to 99% by mass, and more preferably 55% by mass to 95% by mass based on the total solid.

Further, in the present invention, the fullerene derivative (A) may be used either alone or in combination of two or more. Or, the fullerene derivative (A) may be used in combination with other fullerene derivatives, which do not correspond to fullerene or the fullerene derivative (A). In this case, it is preferred that the fullerene derivative (A) is present in the whole resin in an amount of 50% by mass or more.

[2] Compound (B) Generating an Acid Upon Irradiation with an Actinic Ray or Radiation The composition of the present invention contains a compound generating an acid upon irradiation with an actinic ray or radiation (hereinafter, referred to as "acid generator").

As an acid generator, any known compounds generating an acid upon irradiation with an actinic ray or radiation, and mixtures thereof, which are used in a photoinitiator for photocation polymerization, a photoinitiator for photoradical polymerization, a photo-achromatizer or a photo-chromatizer for colorants, or microresist and the like, may be appropriately selected and used.

Examples thereof may include a diazonium salt, a phosphonium salt, a sulfonium salt, an iodonium salt, an imidosulfonate, an oximsulfonate, a diazodisulfone, a disulfone and o-nitrobenzylsulfonate.

A preferred compound among acid generators may be exemplified by a compound represented by the following Formula (ZI), Formula (ZII) or Formula (ZIII).

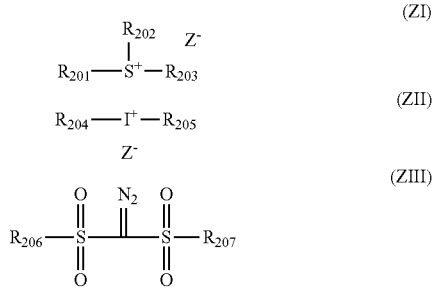

In Formula (ZI), each of $R_{201}$, $R_{202}$ and $R_{203}$ independently represents an organic group.

The number of the organic group as $R_{201}$, $R_{202}$ and $R_{203}$ is generally 1 to 30, and preferably 1 to 20.

Further, two of $R_{201}$ to $R_{203}$ may be combined to form a ring structure, and the ring may contain an oxygen atom, a sulfur atom, an ester bond, an amide bond or a carbonyl group. Examples of the group which two of $R_{201}$ to $R_{203}$ are combined to form may include an alkylene group (for example, a butylene group and a pentylene group).

$Z^-$ represents a non-nucleophilic anion.

Examples of the non-nucleophilic anion as $Z^-$ may include a sulfonate anion, a carboxylate anion, a sulfonylimide anion, a bis(alkylsulfonyl)imide anion, a tris(alkylsulfonyl)methyl anion and the like.

The non-nucleophilic anion refers to an anion having a remarkably low ability to cause a nucleophilic reaction, and an anion capable of suppressing decomposition with the lapse of time by an intramolecular nucleophilic reaction. Accordingly, the stability of the resist composition over time can be enhanced.

Examples of the sulfonate anion may include an aliphatic sulfonate anion, an aromatic sulfonate anion, a camphorsulfonate anion and the like.

Examples of the carboxylate anion may include an aliphatic carboxylate anion, an aromatic carboxylate anion, an aralkylcarboxylate anion and the like.

The aliphatic moiety in the aliphatic sulfonate amnion and the aliphatic carboxylate anion may be either an alkyl group or a cycloalkyl group, and preferably an alkyl group having 1 to 30 carbon atoms and a cycloalkyl group having 3 to 30 carbon atoms, for example, a methyl group, an ethyl group, a propyl group, an isopropyl group, an n-butyl group, an isobutyl group, a sec-butyl group, a pentyl group, a neopentyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, an eicosyl group, a cyclopropyl group, a cyclopentyl group, a cyclohexyl group, an adamantyl group, a norbornyl group, a bornyl group and the like.

Examples of the aromatic group in the aromatic sulfonate anion and the aromatic carboxylate anion may include preferably an aryl group having 6 to 14 carbon atoms, for example, a phenyl group, a tolyl group, a naphthyl group and the like.

The alkyl group, the cycloalkyl group and the aryl group in the aliphatic sulfonate anion and the aromatic sulfonate anion may have a substituent. Examples of the substituent of the alkyl group, the cycloalkyl group and the aryl group in the aliphatic sulfonate anion and the aromatic sulfonate anion may include a nitro group, a halogen atom (a fluorine atom, a chlorine atom, a bromine atom and an iodine atom), a carboxyl group, a hydroxyl group, an amino group, a cyano group, an alkoxy group (having preferably 1 to 15 carbon atoms), a cycloalkyl group (having preferably 3 to 15 carbon atoms), an aryl group (having preferably 6 to 14 carbon atoms), an alkoxycarbonyl group (having preferably 2 to 7 carbon atoms), an acyl group (having preferably 2 to 12 carbon atoms), an alkoxycarbonyloxy group (having preferably 2 to 7 carbon atoms), an alkylthio group (having preferably 1 to 15 carbon atoms), an alkylsulfonyl group (having preferably 1 to 15 carbon atoms), an alkyliminosulfonyl group (having preferably 1 to 15 carbon atoms), an aryloxysulfonyl group (having preferably 6 to 20 carbon atoms), an alkylaryloxysulfonyl group (having preferably 7 to 20 carbon atoms), a cycloalkylaryloxysulfonyl group (having preferably 10 to 20 carbon atoms), an alkyloxyalkyloxy group (having preferably 5 to 20 carbon atoms), a cycloalkylalkyloxyalkyloxy group (having preferably 8 to 20 carbon atoms) and the like. The aryl group and the ring structure possessed by each group may further include an alkyl group (having preferably 1 to 15 carbon atoms) or a cycloalkyl group (having preferably 3 to 15 carbon atoms) as a substituent.

Examples of the aralkyl group in the aralkylcarboxylate anion may include preferably an aralkyl group having 7 to 12 carbon atoms, for example, a benzyl group, a phenethyl group, a naphthylmethyl group, a naphthylethyl group, a naphthylbutyl group and the like.

The alkyl group, the cycloalkyl group, the aryl group and aralkyl group in the aliphatic carboxlyate anion, the aromatic carboxlyate anion and the aralkylcarboxylate anion may have a substituent. Examples of the substituent may include a halogen atom, an alkyl group, a cycloalkyl group, an alkoxy group, an alkylthio group and the like, as in the aromatic sulfonate anion.

Examples of the sulfonylimide anion may include a saccharin anion.

The alkyl group in the bis(alkylsulfonyl)imide anion and the tris(alkylsulfonyl)methide anion is preferably an alkyl group having 1 to 5 carbon atoms, and examples thereof may include a methyl group, an ethyl group, a propyl group, an isopropyl group, an n-butyl group, an isobutyl group, a sec-butyl group, a pentyl group, a neopentyl group and the like. Examples of the substituent of the alkyl group may include a halogen atom, an alkyl group substituted with a halogen atom, an alkoxy group, an alkylthio group, an alkyloxysulfonyl group, an aryloxysulfonyl group, a cycloalkylaryloxysulfonyl group and the like, and preferably an alkyl group substituted with a fluorine atom.

Examples of other non-nucleophilic anion may include phosphorus fluoride, boron fluoride, antimony fluoride and the like.

The non-nucleophilic anion of $Z^-$ is preferably an aliphatic sulfonate anion substituted with a fluorine atom at least at the α-position of the sulfonate, an aromatic sulfonate anion substituted with a fluorine atom or a group having a fluorine atom, a bis(alkylsulfonyl)imide anion in which the alkyl group is substituted with a fluorine atom and a tris(alkylsulfonyl)methide anion in which the alkyl group is substituted with a fluorine atom. The non-nucleophilic anion is more preferably perfluoroaliphatic sulfonate anion having 4 to 8 carbon atoms, a benzensulfonate anion having a fluorine atom, and still more preferably a nonafluorobutanesulfonate anion, a perfluorooctanesulfonate anion, a pentafluorobenzenesulfonate anion, and a 3,5-a bis(trifluoromethyl)benzenesulfonate anion.

The acid generator is preferably a compound generating sulfonic acid represented by Formula (BI), and accordingly, it is possible to make the resolution and roughness performances more excellent. The sulfonic acid represented by Formula (BI) has an aromatic ring, which is a cyclic organic group. Since such a cyclic organic group is bulky and tends to allow the sulfonic acid generated in exposed portions to remain in the exposed portions as compared to a chained group, it is considered that the concern about causing undesirable reactions by diffusion of acid into unexposed portions can be reduced, thereby improving the above-mentioned performances. Further, although the reason is not clear, the developing time dependency can be improved as well.

Accordingly, when the acid generator is, for example, a compound represented by Formula (ZI) or Formula (ZII), the aromatic sulfonate anion is preferably an anion generating an arylsulfonic acid represented by the following Formula (BI).

(BI)

In Formula (BI),

Ar represents an aromatic ring, and may further have a substituent other than a sulfonate group and an A group.

p represents an integer of 0 or more.

A represents a group having a hydrocarbon group.

When p is 2 or more, each A may be the same as or different from every other A.

Formula (BI) will be described in more detail.

The aromatic ring represented by Ar is preferably an aromatic ring having 6 to 30 carbon ring.

Specific examples thereof may include a benzene ring, a naphthalene ring, a pentalene ring, an indene ring, an azulene ring, a heptalene ring, an indecene ring, a perylene ring, a pentacene ring, an acetaphthalene ring, a phenanthrene ring, an antracene ring, a naphthacene ring, a pentacene ring, a chrysene ring, a triphenylene ring, an indene ring, a fluorene ring, a triphenylene ring, a naphthacene ring, a biphenyl ring, a pyrrole ring, a furan ring, a thiophene ring, an imidazole ring, an oxazole ring, thiazole ring, a pyridine ring, a pyrazine ring, a pyrimidine ring, a pyridazine ring, an indolizine ring, an indole ring, a benzofuran ring, a benzothiophene ring, an isobenzofuran ring, a quinolizine ring, a quinoline ring, a phthalazine ring, a naphthyridine ring, a quinoxaline ring, a quinoxazoline ring, an isoquinoline ring, a carbazole ring, a phenanthridine ring, an acridine ring, a phenanthroline ring, a thianthrene ring, a chromene ring, a xanthene ring, a phenoxathiine ring, a phenothiazine ring, a phenazine ring and the like, preferably a benzene ring, a naphthalene ring and an antracene ring, and more preferably a benzene ring.

Examples of the substituent, other than a sulfonate group and an A group, which may be possessed by the aromatic ring may include a halogen atom (a fluorine atom, a chlorine atom, a bromine atom, an iodine atom and the like), a hydroxyl group, a cyano group, a nitro group, a carboxyl group and the like. Further, in the case of having 2 or more substituents, at least two substituents may be bound with each other to form a ring.

Examples of the group having a hydrocarbon group represented by A may include an alkoxy group such as a methoxy group, an ethoxy group and a tert-butoxy group, an aryloxy group such as a phenoxy group and a p-tolyloxy group, an alkylthioxy group such as a methylthioxy group, an ethylthioxy group and a tert-butylthioxy group, an arylthioxy group such as a p-tolylthioxy group, an alkoxycarbonyl group such as a methoxycarbonyl group, a butoxycarbonyl group and a phenoxycarbonyl group, an acetoxy group, a straight alkyl group and branched alkyl group such as a methyl group, an ethyl group, a propyl group, a butyl group, a heptyl group, a hexyl group, a dodecyl group and 2-ethylhexyl group, an alkenyl group such as a vinyl group, a propenyl group and hexenyl group, an alkynyl group such as an acetylene group, a propynyl group and a hexynyl group, an aryl group such as a phenyl group and tolyl group, and an acyl group such as a benzoyl group, an acetyl group and a tolyl group.

Examples of the hydrocarbon group in the group having a hydrocarbon group represented by A may include an acyclic hydrocarbon atom or a cyclic aliphatic group, and the carbon number of the hydrocarbon group is preferably 3 or more.

The A group is preferably a group in which the carbon atom adjacent to Ar is a tertiary or quaternary carbon atom.

Examples of the acyclic in the A group may include an isopropyl group, a t-butyl group, t-a pentyl group, a neopentyl group, a s-butyl group, an isobutyl group, an isohexyl group, a 3,3-dimethylpentyl group, a 2-ethylhexyl group and the like. The upper limit of the number of carbon possessed by the acyclic hydrocarbon group is preferably 12 or less, and more preferably 10 or less.

Examples of the cyclic aliphatic group in the A group may include a cycloalkyl group such as a cyclobutyl group, a cyclopentyl group, cyclohexyl group, a cycloheptyl group and a cyclooctyl group, an adamantyl group, a norbornyl group, a bornyl group, a camphenyl group, a decahydronaphthyl group, a tricyclodecanyl group, a tetracyclodecanyl group, a camphoroyl group, a dicyclohexyl group, a pinenyl group and the like, and may have a substituent. The upper limit of the number of carbon possessed by the cyclic aliphatic group is preferably 15 or less, and more preferably 12 or less.

When the acyclic hydrocarbon group or the cyclic aliphatic group has a substituent, examples of the substituent may include a halogen atom such as a fluorine atom, a chlorine atom, a bromine atom and an iodine atom, an alkoxy group such as a methoxy group, an ethoxy group and a tert-butoxy group, an aryloxy group such as a phenoxy group and a p-tolyoxy group, an alkylthioxy group such as a methylthioxy group, an ethylthioxy group and a tert-butythioxy group, an arylthioxy group such as a phenylthioxy group and a p-tolylthioxy group, an alkoxycarbonyl group such as a methoxycarbonyl group, a butoxycarbonyl group and a phenoxycarbonyl group, an acetoxy group, a straight alkyl group and branched alkyl group such as a methyl group, an ethyl group, a propyl group, a butyl group, a heptyl group, a hexyl group, a dodecyl group and a 2-ethylhexyl group, a cyclic alkyl group such as a cyclohexyl group, an alkenyl group such as a vinyl group, a propenyl group and a hexenyl group, an alkynyl group such as an acetylene group, a propynyl group and a hexynyl group, an aryl group such as a phenyl group and a tolyl group, a hydroxyl group, a carboxyl group, a sulfonate group, carbonyl group, a cyano group and the like.

Specific examples of the cyclic aliphatic group or the acyclic hydrocarbon group as A may include the followings.

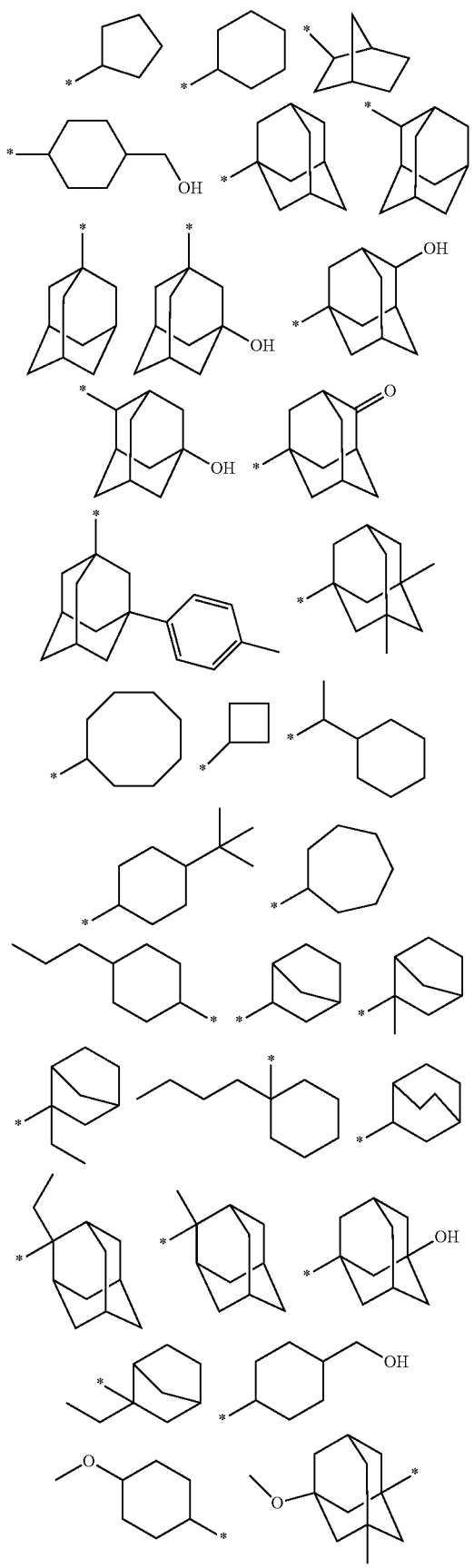
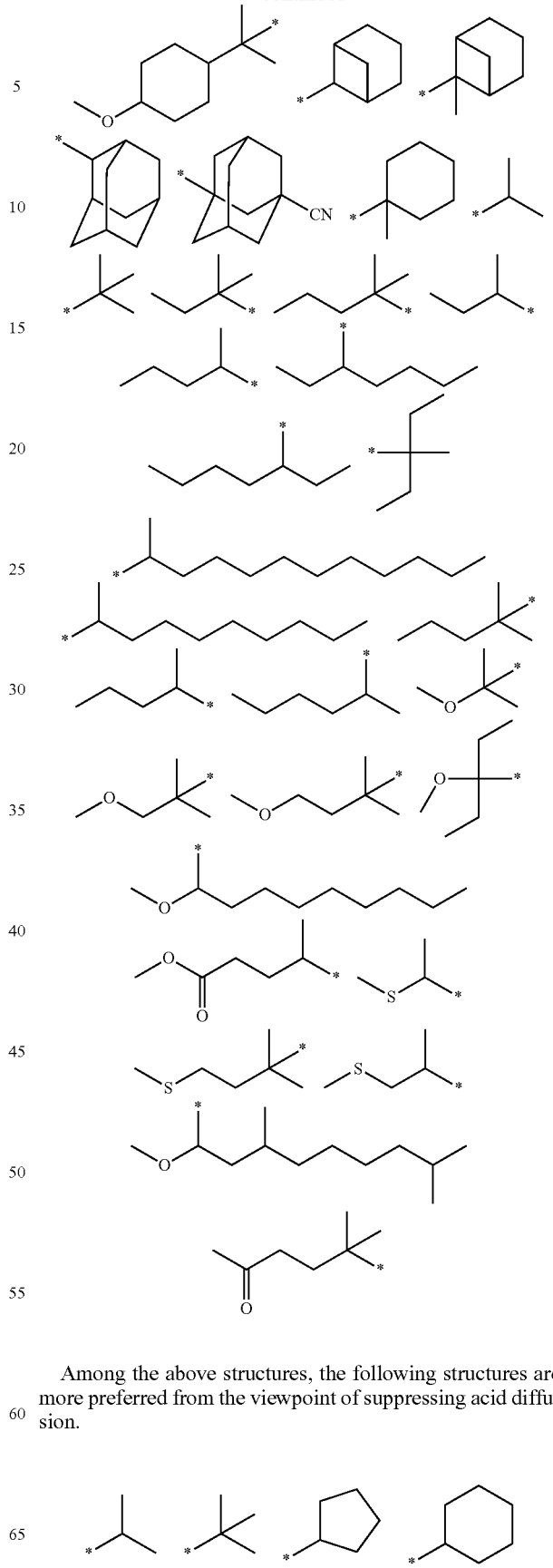
Among the above structures, the following structures are more preferred from the viewpoint of suppressing acid diffusion.

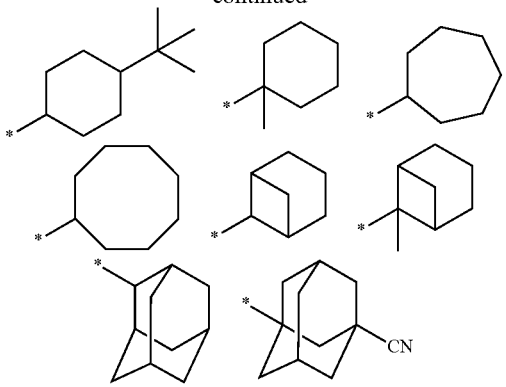

p represents an integer of 0 or more, and the upper limit is not particularly limited as long as it is a chemically possible number. From the viewpoint of suppressing acid diffusion, p represents generally 0 to 5, preferably 1 to 4, more preferably 2 to 3, and most preferably 3.

From the viewpoint of suppressing acid diffusion, the A group is preferably a structure substituting at least one o-position, and more preferably a structure substituting two o-positions.

In an aspect, the acid generator of the present invention is a compound generating an acid represented by Formula (BII).

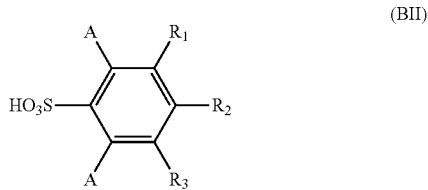

In the formula, A is the same as A is Formula (BI), and each A may be the same as or different from every other A. Each of $R_1$ to $R_3$ independently represents a hydrogen atom, a group having a hydrocarbon group, a halogen atom, a hydroxyl group, a cyano group or a nitro group. Specific examples of the group having a hydrocarbon group may include the groups exemplified above.

The acid generator is preferably a compound generating sulfonica acid represented by the following Formula (I). Since the sulfonic acid represented by Formula (I) has a cyclic organic group, the resolution and roughness performances can be improved for the above-mentioned reason. Further, although the reason is not clear likewise, the developing time dependency can be improved as well.

Accordingly, when the acid generator is, for example, a compound represented by Formula (ZI) or Formula (ZII), the aromatic sulfonate anion is preferably an anion generating the acid represented by the following Formula (I).

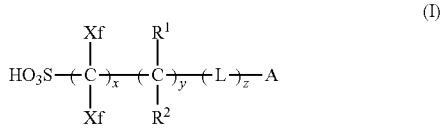

In the formula, each Xf independently represents a fluorine atom or an alkyl group substituted with at least one fluorine atom.

Each of $R^1$ and $R^2$ independently represents a group selected from a hydrogen atom, a fluorine atom and an alkyl group, and when a plurality of $R^1$ and $R^2$ are present, each of $R^1$ and $R^2$ may be the same as or different from every other $R^1$ and $R^2$.

L represents a divalent linking group, and when a plurality of L are present, each L may be the same as or different from every other L.

A represents a cyclic organic group.

x represents an integer of 1 to 20, y represents an integer of 0 to 10, and z represents an integer of 0 to 10.

Formula (I) will be described in more detail.

The alkyl group in the alkyl group substituted with a fluorine atom of Xf is preferably an alkyl group having 1 to 10 carbon atoms, and more preferably 1 to 4 carbon atoms. Further, the alkyl group substituted with a fluorine atom of Xf is preferably a perfluoroalkyl group.

Xf is preferably a fluorine atom or a perfluoroalkyl group having 1 to 4 carbon atoms. Specific examples of Xf may include a fluorine atom, $CF_3$, $C_2F_5$, $C_3F_7$, $C_4F_9$, $C_5F_{11}$, $C_6F_{13}$, $C_7F_{15}$, $C_8F_7$, $CH_2CF_3$, $CH_2CH_2CF_3$, $CH_2C_2F_5$, $CH_2CH_2C_2F_5$, $CH_2C_3F_7$, $CH_2CH_2C_3F_7$, $CH_2C_4F_9$ and $CH_2CH_2C_4F_9$, and among them, a fluorine atom and $CF_3$ are preferred. Especially, it is preferred that both Xf's are a fluorine atom.

The alkyl group of $R^1$ and $R^2$ may have a substituent (preferably a fluorine atom), and preferably has 1 to 4 carbon atoms. A perfluoroalkyl group having 1 to 4 carbon atoms is more preferred. Specific examples of the alkyl group having a substituent of $R^1$ and $R^2$ may include $CF_3$, $C_2F_5$, $C_3F_7$, $C_4F_9$, $C_5F_{11}$, $C_6F_{13}$, $C_7F_{15}$, $C_8F_{17}$, $CH_2CF_3$, $CH_2CH_2CF_3$, $CH_2C_2F_5$, $CH_2CH_2C_2F_5$, $CH_2C_3F_7$, $CH_2CH_2C_3F_7$, $CH_2C_4F_9$ and $CH_2CH_2C_4F_9$, and among them, $CF_3$ is preferred.

$R^1$ and $R^2$ are preferably a fluorine atom or $CF_3$.

y is preferably 0 to 4, and more preferably 0. x is preferably 1 to 8, and among them, preferably 1 to 4, and particularly 1. z is preferably 0 to 8, and among them, preferably 0 to 4.

The divalent linking group of L is not particularly limited, and examples thereof may include —COO—, —OCO—, —CONR— (R is a hydrogen atom, an alkyl group or a cycloalkyl group), —CO—, —O—, —S—, —SO—, —SO$_2$—, an alkylene group, a cycloalkylene group, an alkenylene group or a linking group formed by combining two or more thereof, and a linking group having a total carbon number of 12 or less. Among them, —COO—, —OCO—, —CONR—, —CO—, —O— and —SO$_2$— are preferred, and —COO—, —OCO— and —SO$_2$— are more preferred.

The cyclic organic group of A is not particularly limited as long as it has a cyclic structure, and may include an alicyclic, an aryl group, a heterocyclic group (including a group having an aromaticity as well as a group not having an aromaticity, for example, a tetrahydropyran ring and lactone ring structure) and the like.

The alicyclic group may be either monocyclic or polycyclic, and is preferably a monocyclic cycloalkyl group such as a cyclopentyl group, cyclohexyl group and a cyclooctyl group, and a polycyclic cycloalkyl group such as a norbornyl group, a tricyclodecanyl group, a tetracyclodecanyl group, a tetracyclododecanyl group and an adamantyl group. Among them, alicyclic groups having a bulky structure of 7 or more carbon atoms such as a norbornyl group, a tricyclodecanyl group, a tetracyclodecanyl group, a tetracyclododecanyl group and an adamantyl group are preferred from the viewpoint of improvement in MEEF (Mask Error Enhancement Factor) because diffusion into a film can be suppressed in PEB (Post Exposure Bake) process.

The aryl group may be either monocyclic or polycyclic, and may include a benzene ring, a naphthalene ring, a phenanthrene ring and an antracene ring. Among them, naphthalene having a low absorbance is preferred from the viewpoint of an absorbance at 193 nm.

The heterocyclic group may be either monocyclic or polycyclic, and may include a group derived from furan ring, a thiophene ring, a benzofuran ring, a benzothiophene ring, a dibenzofuran ring, a dibenzothiophene ring, a pyridine ring or a decahydroisoquinoline ring. Among them, a group derived from a furan ring, thiophene ring, a pyridine ring or a decahydroisoquinoline ring is preferred.

Further, the cyclic organic group may include a lactone structure as well.

The cyclic organic group may have a substituent, and examples of the substituent may include an alkyl group (which may be either straight or branched, and preferably has 1 to 12 carbon atoms), a cycloalkyl group (which may be any of a monocyclic, polycyclic and Spiro ring, and preferably has 3 to 20 carbon atoms), an aryl group (preferably having 6 to 14 carbon atoms), a hydroxyl group, an alkoxy group, an ester group, an amide group, an urethane group, an ureido group, a thioether group, a sulfonamide group, a sulfonate ester and the like. Meanwhile, the carbon constituting the cyclic organic group (carbon contributing to ring formation) may be a carbonyl carbon.

Examples of the organic group represented by $R_{201}$, $R_{202}$ and $R_{203}$ may include the corresponding groups in the compounds (ZI-1), (ZI-2), (ZI-3) and (ZI-4) as described below.

Meanwhile, the compound may have a plurality of structures represented by Formula (ZI). For example, the compound may have a structure in which at least one of $R_{201}$ to $R_{203}$ of the compound represented by Formula (ZI) is bound via a single bond or a linking group to at least one of $R_{201}$ to $R_{203}$ of another compound represented by Formula (ZI).

Examples of a more preferred component (ZI) may include the compounds (ZI-1), (ZI-2) and (ZI-3) and (ZI-4) as described below.

The compound (ZI-1) is an arylsulfonium compound in which at least one of $R_{201}$ to $R_{203}$ in Formula (ZI) is an aryl group, that is, a compound having arylsulfonium as a cation.

In the arylsulfonium compound, all of $R_{201}$ to $R_{203}$ may be an aryl group, or some of $R_{201}$ to $R_{203}$ may be an aryl group, and the rest may be an alkyl group or a cycloalkyl group.

Examples of the arylsulfonium compound may include a triarylsulfonium compound, a diarylalkylsulfonium compound, an aryldialkylsulfonium compound, a diarylcycloalkylsulfonium compound and an aryldicycloalkylsulfonium compound.

The aryl group of the arylsulfonium compound is preferably a phenyl group or a naphthyl group, and more preferably a phenyl group. The aryl group may be an aryl group having a heterocyclic structure having an oxygen atom, a nitrogen atom, a sulfur atom and the like. Examples of the heterocyclic structure may include a pyrrole residue structure, furan residue structure, thiophene residue structure, an indole residue structure, a benzofuran residue structure, a benzothiophene residue structure and the like. When the arylsulfonium compound has two or more aryl groups, the two aryl groups may be the same as or different from each other.

The alkyl group or the cycloalkyl group possessed as necessary by the arylsulfonium compound is preferably a straight or branched alkyl group having 1 to 15 carbon atoms and a cycloalkyl group having 3 to 15 carbon atoms, for example, a methyl group, an ethyl group, a propyl group, an n-butyl group, a sec-butyl group, a t-butyl group, a cyclopropyl group, a cyclobutyl group, cyclohexyl group and the like.

The aryl group, the alkyl group and the cycloalkyl group of $R_{201}$ to $R_{203}$ may have an alkyl group (for example, having 1 to 15 carbon atoms), a cycloalkyl group (for example, having 3 to 15 carbon atoms), an aryl group (for example, having 6 to 14 carbon atoms), an alkoxy group (for example, having 1 to 15 carbon atoms), a halogen atom, a hydroxyl group or a phenylthio group as a substituent. A preferred substituent is a straight or branched alkyl group having 1 to 12 carbon atoms, a cycloalkyl group having 3 to 12 carbon atoms or a straight, branched or cyclic alkoxy group having 1 to 12 carbon atoms, and more preferably an alkyl group having 1 to 4 carbon atoms or an alkoxy group having 1 to 4 carbon atoms. The substituent may be substituted to any one of three $R_{201}$ to $R_{203}$, or may be substituted to all of the three groups. Further, when $R_{201}$ to $R_{203}$ are an aryl group, the substituent is preferably substituted at the p-position of the aryl group.

Next, the compound (ZI-2) will be described.

The compound (ZI-2) is a compound in which each of $R_{201}$ to $R_{203}$ in Formula (ZI) independently represents an organic group having no aromatic ring. Herein, the aromatic ring includes an aromatic ring containing a heteroatom as well.

The organic group containing no aromatic ring as $R_{201}$ to $R_{203}$ has generally 1 to 30 carbon atoms, and preferably 1 to 20 carbon atoms.

Each of $R_{201}$ to $R_{203}$ is independently preferably an alkyl group, a cycloalkyl group, an allyl group or a vinyl group, more preferably a straight or branched 2-oxoalkyl group, a 2-oxocycloalkyl group, an alkoxycarbonylmethyl group, and particularly preferably a straight or branched 2-oxoalkyl group.

Examples of the alkyl group and the cycloalkyl group of $R_{201}$ to $R_{203}$ may include preferably a straight or branched alkyl group having 1 to 10 carbona atoms (for example, a methyl group, an ethyl group, a propyl group, a butyl group and a pentyl group) and a cycloalkyl group having 3 to 10 carbon atoms (a cyclopentyl group, a cyclohexyl group and a norbornyl group). The alkyl group may include more preferably 2-oxoalkyl group and an alkoxycarbonylmethyl group. The cycloalkyl group may include more preferably a 2-oxocycloalkyl group.

The 2-oxoalkyl group may be either straight or branched, and may include preferably a group having >C=O at the 2-position of the alkyl group.

The 2-oxocycloalkyl group may include preferably a group having >C=O at the 2-position of the cycloalkyl group.

Example of the alkoxy group in the alkoxycarbonylmethyl group may include preferably an alkoxy group having 1 to 5 carbon atoms (a methoxy group, an ethoxy group, a propoxy group, a butoxy group and a pentoxy group).

$R_{201}$ to $R_{203}$ may be further substituted with a halogen atom, an alkoxy group (for example, having 1 to 5 carbon atoms), a hydroxyl group, a cyano group or a nitro group.

Next, the compound (ZI-3) will be described.

The compound (ZI-3) is a compound represented by the following Formula (ZI-3) and having a phenacylsulfonium salt structure.

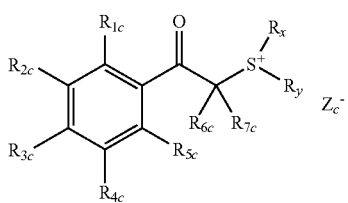

(ZI-3)

In Formula (ZI-3),

Each of $R_{1c}$ to $R_{5c}$ independently represents a hydrogen atom, an alkyl group, a cycloalkyl group, an aryl group, an alkoxy group, an aryloxy group, an alkoxycarbonyl group, an alkylcarbonyloxy group, a cycloalkylcarbonyloxy group, a halogen atom, a hydroxyl group, a nitro group, an alkylthio group or an arylthio group.

Each of $R_{6c}$ and $R_{7c}$ independently represents a hydrogen atom, an alkyl group, a cycloalkyl group, a halogen atom, a cyano group or an aryl group.

Each of $R_x$ and $R_y$ independently represents an alkyl group, a cycloalkyl group, a 2-oxoalkyl group, a 2-oxocycloalkyl group, an alkoxycarbonylalkyl group, an allyl group or a vinyl group.

Any two or more of $R_{1c}$ to $R_{5c}$, $R_{5c}$ and $R_{6c}$, $R_{6c}$ and $R_{7c}$, $R_{5c}$ and $R_x$, and $R_x$ and $R_y$ may be bound with each other to form a ring structure, and the ring structure may contain an oxygen atom, a sulfur atom, a ketone group, an ester bond or an amide bond.

Examples of the ring structure may include an aromatic or non-aromatic hydrocarbon ring, an aromatic or non-aromatic heterocycle, or a polycyclic condensed ring formed by combining two or more of the rings. The ring structure may be a 3- to 10-membered ring, preferably 4- to 8-membered ring, and more preferably 5- or 6-membered ring.

Examples of the group which any two or more of $R_{1c}$ to $R_{5c}$, $R_{6c}$ and $R_{7c}$, and $R_x$ and $R_y$ are combined to form may include a butylene group, a pentylene group and the like.

The group which $R_{5c}$ and $R_{6c}$, and $R_{5c}$ and $R_x$ are bound to form is preferably a single bond or an alkylene group, and the alkylene group may be a methylene group, an ethylene group or the like.

$Zc^-$ represents a non-nucleophilic anion, and may be exemplified by the same non-nucleophilic anion as $Z^-$ in Formula (ZI).

The alkyl group as $R_{1c}$ to $R_{7c}$ may be either straight or branched, and examples thereof may include an alkyl group having 1 to 20 carbon atoms, and preferably a straight or branched alkyl group having 1 to 12 carbon atoms (for example, a methyl group, an ethyl group, a straight or branched propyl group, a straight or branched butyl group and a straight or branched pentyl group), and examples of the cycloalkyl group may include a cycloalkyl group having 3 to 10 carbon atoms (for example, a cyclopentyl group and a cyclohexyl group).

The aryl group as $R_{1c}$ to $R_{5c}$ preferably has 5 to 15 carbon atoms, and examples thereof may include a phenyl group and a naphthyl group.

The alkoxy group as $R_{1c}$ to $R_{5c}$ may be either straight, branched or cyclic, and examples thereof may include an alkoxy group having 1 to 10 carbon atoms, and preferably a straight and branched alkoxy group having 1 to 5 carbon atoms (for example, a methoxy group, an ethoxy group, a straight or branched propoxy group, a straight or branched butoxy group, a straight or branched pentoxy group) and a cyclic alkoxy group having 3 to 10 carbon atoms (for example, a cyclopentyloxy group, a cyclohexyloxy group).

Specific examples of the alkoxy group in the alkoxycarbonyl group as $R_{1c}$ to $R_{5c}$ are the same as the specific examples of the alkoxy group as $R_{1c}$ to $R_{5c}$.

Specific examples of the alkyl group in the alkylcarbonyloxy group and the alkylthio group as $R_{1c}$ to $R_{5c}$ are the same as specific examples of the alkyl group as $R_{1c}$ to $R_{5c}$.

Specific examples of the cycloalkyl group in the cycloalkylcarbonyloxy group as $R_{1c}$ to $R_{5c}$ are the same as the specific examples of the cycloalkyl group as $R_{1c}$ to $R_{5c}$.

Specific examples of the aryl group in the aryloxy group and an arylthio group as $R_{1c}$ to $R_{5c}$ are the same as the specific examples of the aryl group as $R_{1c}$ to $R_{5c}$.

Preferably, any of $R_{1c}$ to $R_{5c}$ is a straight or branched alkyl group, a cycloalkyl group or a straight, branched or cyclic alkoxy group, and more preferably the sum of the number of carbon of $R_{1c}$ to $R_{5c}$ is 2 to 15. Accordingly, the solubility in solvents may be enhanced more, thereby suppressing the generation of particles during storage.

Examples of the ring which may be formed by combining any two of $R_{1c}$ to $R_{5c}$ with each other may include preferably a 5-membered or 6-membered ring, and particularly preferably 6-membered ring (for example, a phenyl ring).

Examples of the ring structure which may be formed by combining $R_{5c}$ and $R_{6c}$ with each other may include a 4- or greater membered ring (particularly preferably a 5- or 6-membered ring) formed together with the carbonyl carbon atom and the carbon atom in Formula (I) by combining $R_{5c}$ and $R_{6c}$ to each other to constitute a single bond or an alkylene group (such as a methylene group or an ethylene group).

The aryl group as $R_{6c}$ and $R_{7c}$ has preferably 5 to 15 carbon atoms, and examples thereof may include a phenyl group and a naphthyl group.

An aspect in which both of $R_{6c}$ and $R_{7c}$ are an alkyl group is preferred. In particular, an aspect in which each of $R_{6c}$ and $R_{7c}$ is a straight or branched alkyl group having 1 to 4 carbon atoms is preferred, and an aspect in which both are a methyl group is particularly preferred.

Further, when $R_{6c}$ and $R_{7c}$ are bound with each other to form a ring, the group formed by combining $R_{6c}$ and $R_{7c}$ is preferably an alkylene group having 2 to 10 carbon atoms, and examples thereof may include an ethylene group, a propylene group, a butylene group, a pentylene group, a hexylene group and the like. In addition, the ring formed by combining $R_{6c}$ and $R_{7c}$ may have a heteroatom such as an oxygen atom in the ring.

Examples of the alkyl group and the cycloalkyl group as $R_x$ and $R_y$ are the same as those of the alkyl group and the cycloalkyl group in $R_{1c}$ to $R_{7c}$.

Examples of the 2-oxoalkyl group and the 2-oxocycloalkyl group as $R_x$ and $R_y$ may include a group having >C=O at the 2-position of the alkyl group and the cycloalkyl group as $R_{1c}$ to $R_{7c}$.

Examples of the alkoxy group in the alkoxycarbonylalkyl group as $R_x$ and $R_y$ are the same as those of the alkoxy group in $R_{1c}$ to $R_{5c}$, and examples of the alkyl group may include an alkyl group having 1 to 12 carbon atoms, and preferably a straight alkyl group having 1 to 5 carbon atoms (for example, a methyl group and an ethyl group).

The allyl group as $R_x$ and $R_y$ is not particularly limited, but is preferably an unsubstituted allyl group, or an allyl group substituted with a monocyclic or polycyclic cycloalkyl group (preferably a cycloalkyl group having 3 to 10 carbon atoms).

The vinyl group as $R_x$ and $R_y$ is not particularly limited, but is preferably an unsubstituted vinyl group, or a vinyl group substituted with a monocyclic or polycyclic cycloalkyl group (preferably a cycloalkyl group having 3 to 10 carbon atoms).

Examples of the ring structure which may be formed by combining $R_{5c}$ and $R_x$ with each other may include a 5- or greater membered ring (particularly preferably a 5-membered ring) formed together with a sulfur atom and a carbonyl carbon atom in Formula (I) by combining $R_{5c}$ and $R_x$ with each other to constitute a single bond or an alkylene group (a methylene group, an ethylene group or the like).

Examples of the ring structure which may be formed by combining $R_x$ and $R_y$ with each other may include a 5- or 6-membered ring, particularly preferably a 5-membered ring (that is, a tetrahydrothiophene ring), formed together with a sulfur atom in Formula (ZI-3) by divalent $R_x$ and $R_y$ (for example, a methylene group, an ethylene group, a propylene group and the like).

Each of $R_x$ and $R_y$ is preferably an alkyl group or a cycloalkyl group having 4 or more carbon atoms, more preferably 6 or more carbon atoms, and still more preferably 8 or more carbon atoms.

Each of $R_{1c}$ to $R_{7c}$ and $R_x$ and $R_y$ may further have a substituent, and examples of the substituent may include a halogen atom (for example, a fluorine atom), a hydroxyl group, a carboxyl group, a cyano group, a nitro group, an alkyl group, a cycloalkyl group, an aryl group, an alkoxy group, an aryloxy group, an acyl group, an arylcarbonyl group, an alkoxyalkyl group, an aryloxyalkyl group, an alkoxycarbonyl group, an aryloxycarbonyl group, an alkoxycarbonyloxy group, an aryloxycarbonyloxy group and the like.

In Formula (ZI-3), it is more preferred that each of $R_{1c}$, $R_{2c}$, $R_{4c}$ and $R_{5c}$ independently represents a hydrogen atom and $R_{3c}$ represents a group other than a hydrogen atom, that is, an alkyl group, a cycloalkyl group, an aryl group, an alkoxy group, an aryloxy group, an alkoxycarbonyl group, an alkylcarbonyloxy group, a cycloalkylcarbonyloxy group, a halogen atom, a hydroxyl group, a nitro group, an alkylthio group or an arylthio group.

The cation in the compound (ZI-2) or (ZI-3) in the present invention may be exemplified by the following specific examples.

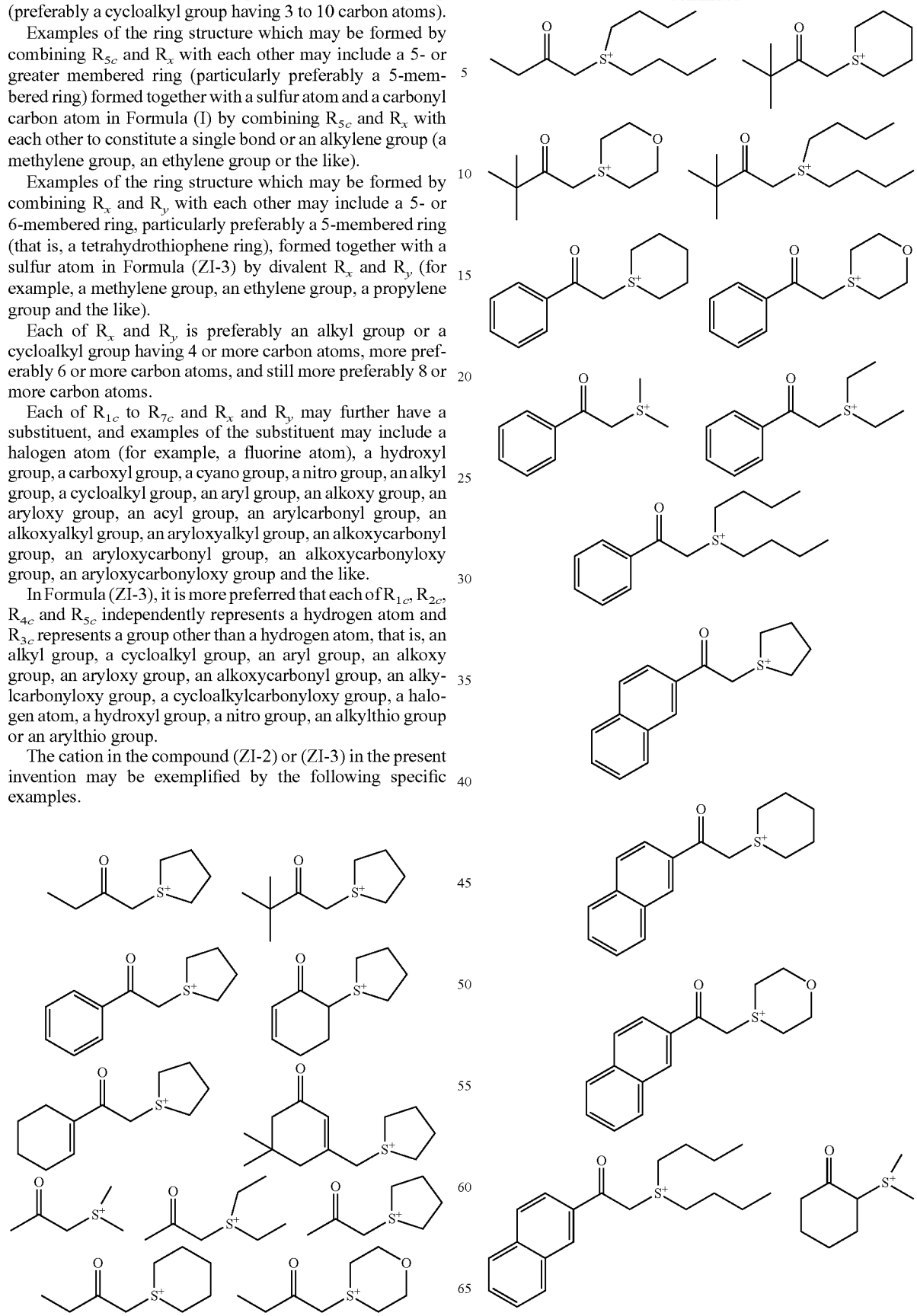

35
-continued
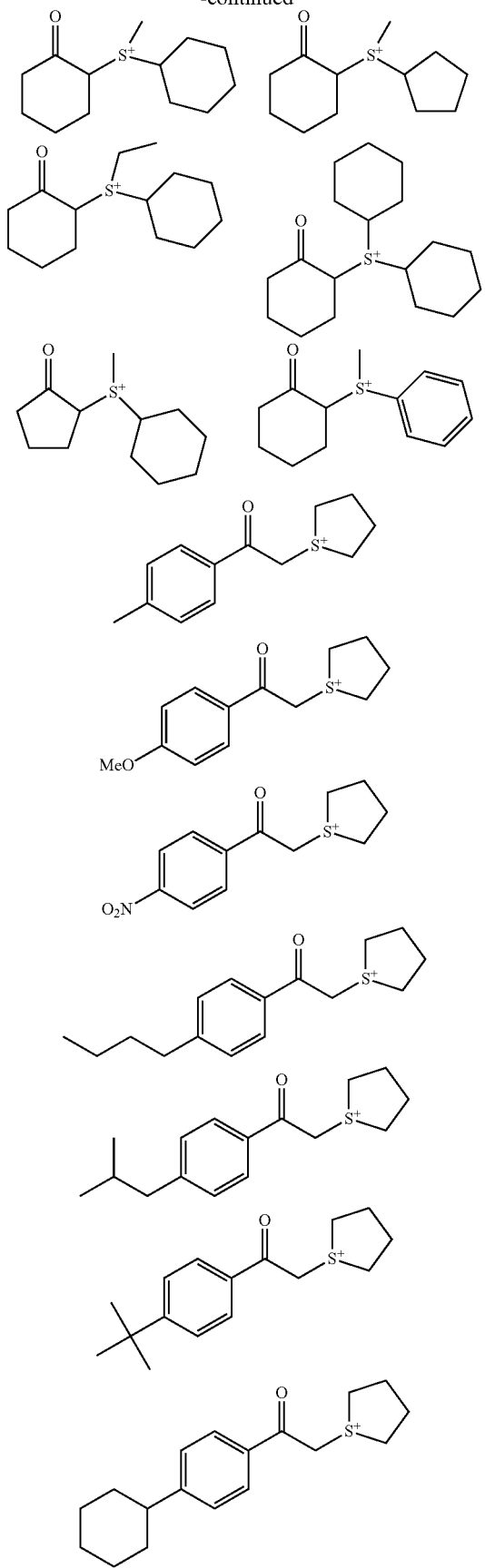
36
-continued
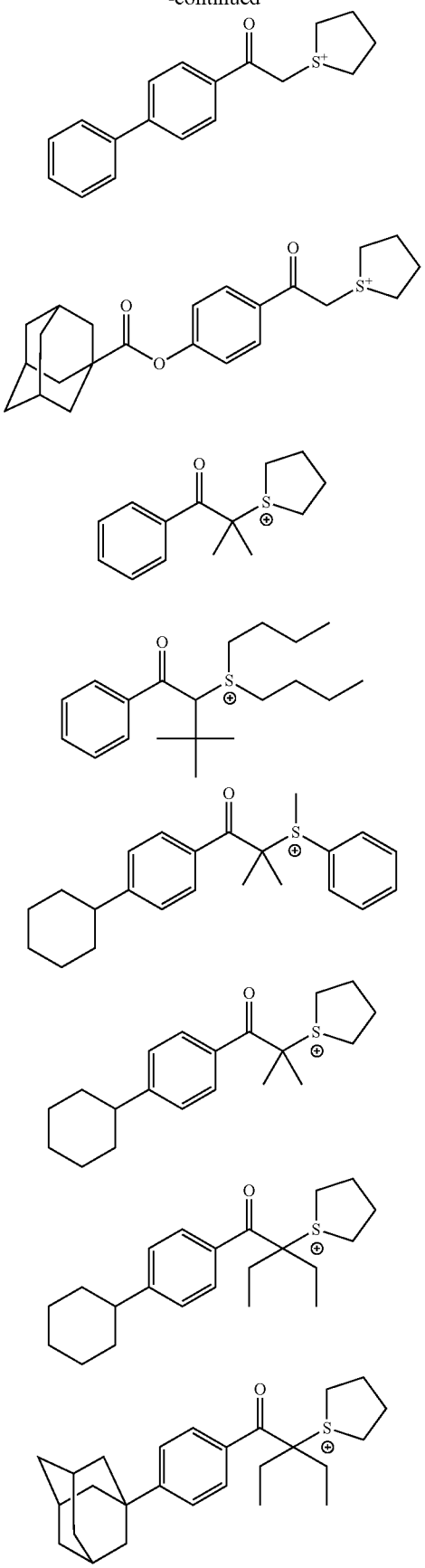

37
-continued
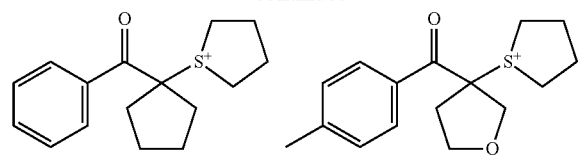
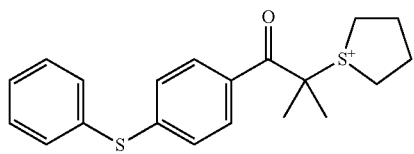
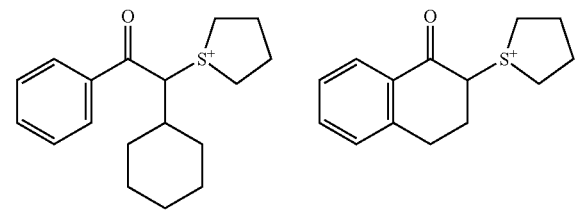
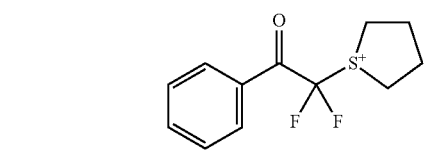
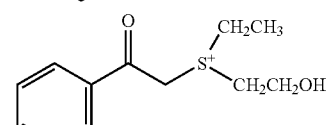
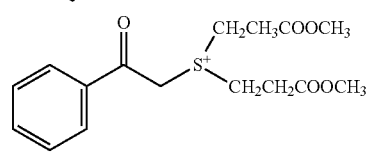
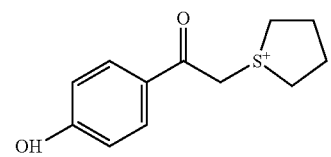
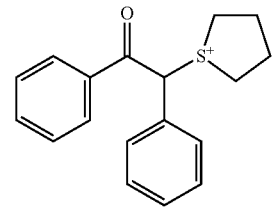
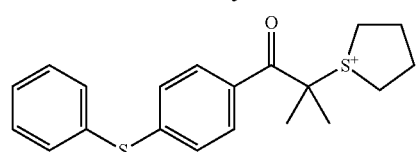
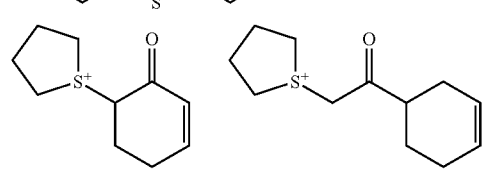
38
-continued
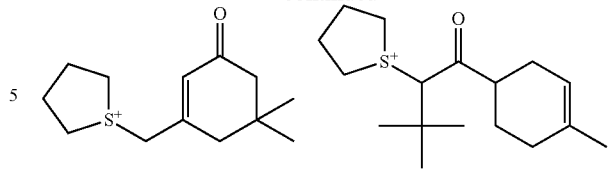
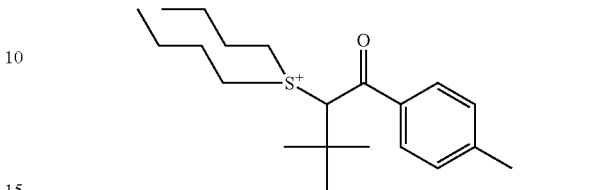
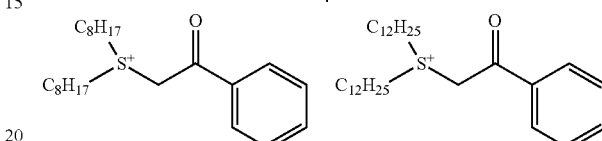
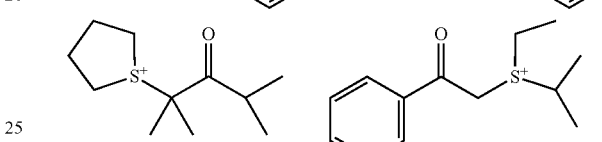
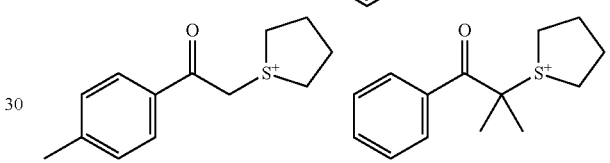
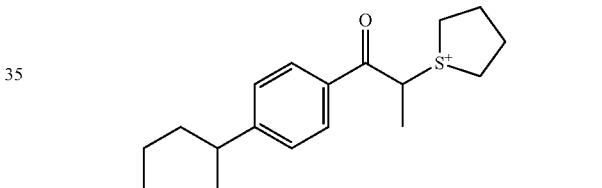
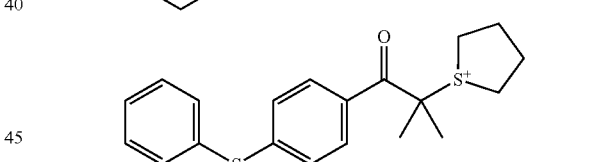
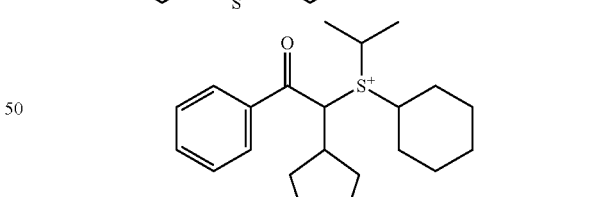
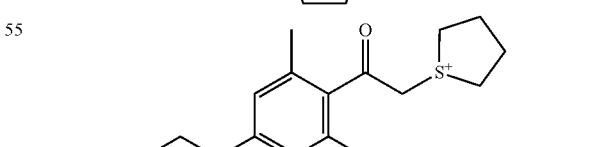
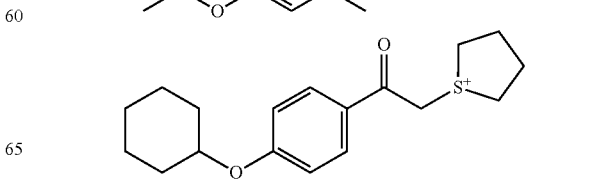

-continued

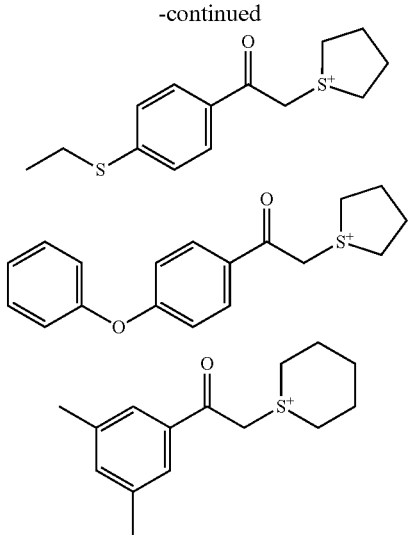

Next, the compound (ZI-4) will be described.

The compound (ZI-4) is represented by the following Formula (ZI-4).

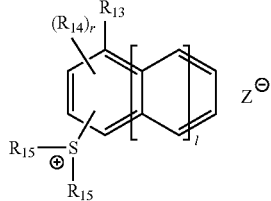

(ZI-4)

In Formula (ZI-4), $R_{13}$ represents a hydrogen atom, a fluorine atom, a hydroxyl group, an alkyl group, a cycloalkyl group, an alkoxy group, an alkoxycarbonyl group or a group having a cycloalkyl group. These groups may have a substituent.

When a plurality of $R_{14}$ is present, each $R_{14}$ independently represents a hydroxyl group, an alkyl group, a cycloalkyl group, an alkoxy group, an alkoxycarbonyl group, an alkylcarbonyl group, an alkylsulfonyl group, a cycloalkylsulfonyl group or a group having a cycloalkyl group. These groups may have a substituent.

Each $R_{15}$ independently represents an alkyl group, a cycloalkyl group or a naphthyl group. Two of $R_{15}$ may be bonded to each other to form a ring. These groups may have a substituent.

l represents an integer of 0 to 2.

r represents an integer of 0 to 8.

$Z^-$ represents a non-nucleophilic anion, and examples thereof are the same as those of the non-nucleophilic anion of $Z^-$ in Formula (ZI).

In Formula (ZI-4), the alkyl group of $R_{13}$, $R_{14}$ and $R_{15}$ is preferably a straight or branched alkyl group having 1 to 10 carbon atoms, and preferably red examples thereof include a methyl group, an ethyl group, an n-butyl group, a t-butyl group and the like.

Examples of the cycloalkyl group of $R_{13}$, $R_{14}$ and $R_{15}$ may include a monocyclic or polycyclic cycloalkyl group (preferably a cycloalkyl group having 3 to 20 carbon atoms), and particularly preferably cyclopropyl, cyclopentyl, cyclohexyl, cycloheptyl and cyclooctyl.

The alkoxy group of $R_{13}$ and $R_{14}$ is preferably a straight or branched alkoxy group having 1 to 10 carbon atoms, and preferred examples thereof include a methoxy group, an ethoxy group, an n-propoxy group, an n-butoxy group and the like.

The alkoxycarbonyl group of $R_{13}$ and $R_{14}$ is preferably a straight or branched alkoxycarbonyl group having 2 to 11 carbon atoms, and preferred examples thereof include a methoxycarbonyl group, an ethoxycarbonyl group, an n-butoxycarbonyl group and the like.

Examples of the group having a cycloalkyl group of $R_{13}$ and $R_{14}$ may include a monocyclic or polycyclic cycloalkyl group (preferably a cycloalkyl group having 3 to 20 carbon atoms), and examples thereof may include a monocyclic or polycyclic cycloalkyloxy group and an alkoxy group having a monocyclic or polycyclic cycloalkyl group. These groups may further have a substituent.

The monocyclic or polycyclic cycloalkyloxy group of $R_{13}$ and $R_{14}$ has a total carbon number of preferably 7 or more, and more preferably 7 to 15, and preferably has a monocyclic cycloalkyl group. The monocyclic cycloalkyloxy group having a total carbon number of 7 or more represents a monocyclic cycloalkyloxy group in which a cycloalkyloxy group such as a cyclopropyloxy group, a cyclobutyloxy group, a cyclopentyloxy group, a cyclohexyloxy group, a cycloheptyloxy group, a cyclooctyloxy group and a cyclododecanyloxy group arbitrarily has a substituent such as an alkyl group such as a methyl group, an ethyl group, a propyl group, a butyl group, a pentyl group, a hexyl group, a heptyl group, an octyl group, a dodecyl group, a 2-ethylhexyl group, an isopropyl group, a sec-butyl group, a t-butyl group and an iso-amyl group, a hydroxyl group, halogen atom (fluorine, chlorine, bromine and iodine), a nitro group, a cyano group, an amide group, a sulfonamide group, alkoxy group such as a methoxy group, an ethoxy group, a hydroxyethoxy group, a propoxy group, a hydroxypropoxy group and a butoxy group, an alkoxycarbonyl group such as a methoxycarbonyl group and an ethoxycarbonyl group, an acyl group such as a formyl group, an acetyl group and a benzoyl group, an acyloxy group such as an acetoxy group and a butyryloxy group, a carboxyl group, and the like, and in which the total carbon number inclusive of the carbon number of an arbitrary substituent on the cycloalkyl group is 7 or more.

Further, examples of the polycyclic cycloalkyloxy group having a total carbon number of 7 or more include a norbornyloxy group, a tricyclodecanyloxy group, a tetracyclodecanyloxy group, an adamantyloxy group and the like.

The alkoxy group having a monocyclic or polycyclic cycloalkyl group of $R_{13}$ and $R_{14}$ has preferably a total carbon number of 7 or more, and more preferably a total carbon number ranging from 7 to 15, and is preferably an alkoxy group having a monocyclic cycloalkyl group. The alkoxy group having a total carbon number of 7 or more and having a monocyclic cycloalkyl group represents an alkoxy group in which an alkoxy group such as methoxy, ethoxy, propoxy, butoxy, pentyloxy, hexyloxy, heptoxy, octyloxy, dodecyloxy, 2-ethylhexyloxy, isopropoxy, sec-butoxy, t-butoxy and iso-amyloxy is substituted with the above-described monocyclic cycloalkyl group which may have a substituent, and where the total carbon number inclusive of the carbon number of the substituent is 7 or more. Examples thereof include a cyclohexylmethoxy group, a cyclopentylethoxy group, a cyclohexylethoxy group and the like, and a cyclohexylmethoxy group is preferred.

Further, examples of the alkoxy group having a total carbon number of 7 or more and having a polycyclic cycloalkyl group may include a norbornylmethoxy group, a norbornylethoxy group, a tricyclodecanylmethoxy group, a tricyclodecanylethoxy group, a tetracyclodecanylmethoxy group, a tetracyclodecanylethoxy group, an adamantylmethoxy group, an adamantylethoxy group and the like, and a norbornylmethoxy group, a norbornylethoxy group and the like are preferred.

Specific examples of the alkyl group in the alkylcarbonyl group of $R_{14}$ are the same as those of the above-described alkyl group as $R_{13}$ to $R_{15}$.

The alkylsulfonyl group and cycloalkylsulfonyl group of $R_{14}$ are preferably a straight, branched or cyclic alkylsulfonyl group having 1 to 10 carbon atoms, and preferred examples thereof include a methanesulfonyl group, an ethanesulfonyl group, an n-propanesulfonyl group, an n-butanesulfonyl group, a cyclopentanesulfonyl group, a cyclohexanesulfonyl group and the like.

Examples of the substituent which each of the groups may have include a halogen atom (for example, a fluorine atom), a hydroxyl group, a carboxyl group, a cyano group, a nitro group, an alkoxy group, an alkoxyalkyl group, an alkoxycarbonyl group, an alkoxycarbonyloxy group and the like.

Examples of the alkoxy group may include a straight, branched or cyclic alkoxy group having 1 to 20 carbon atoms, and the like, such as a methoxy group, an ethoxy group, an n-propoxy group, an i-propoxy group, an n-butoxy group, a 2-methylpropoxy group, a 1-methylpropoxy group, a t-butoxy group, a cyclopentyloxy group and a cyclohexyloxy group.

Examples of the alkoxyalkyl group may include a straight, branched or cyclic alkoxyalkyl group having 2 to 21 carbon atoms, such as a methoxymethyl group, an ethoxymethyl group, a 1-methoxyethyl group, a 2-methoxyethyl group, a 1-ethoxyethyl group and a 2-ethoxyethyl group.

Examples of the alkoxycarbonyl group may include a straight, branched or cyclic alkoxycarbonyl group having 2 to 21 carbon atoms and the like, such as a methoxycarbonyl group, an ethoxycarbonyl group, an n-propoxycarbonyl group, an i-propoxycarbonyl group, an n-butoxycarbonyl group, a 2-methylpropoxycarbonyl group, a 1-methylpropoxycarbonyl group, a t-butoxycarbonyl group, a cyclopentyloxycarbonyl group and a cyclohexyloxycarbonyl group.

Examples of the alkoxycarbonyloxy group may include a straight, branched or cyclic alkoxycarbonyloxy group having 2 to 21 carbon atoms, and the like, such as a methoxycarbonyloxy group, an ethoxycarbonyloxy group, an n-propoxycarbonyloxy group, an i-propoxycarbonyloxy group, an n-butoxycarbonyloxy group, a t-butoxycarbonyloxy group, a cyclopentyloxycarbonyloxy group and a cyclohexyloxycarbonyloxy group.

Examples of the ring structure which may be formed by combining two $R_{15}$ with each other may include a 5- or 6-membered ring formed together with the sulfur atom in Formula (ZI-4) by two $R_{15}$, and particularly preferably a 5-membered ring (that is, a tetrahydrothiophene ring), and may be condensed with an aryl group or a cycloalkyl group. The divalent $R_{15}$ may have a substituent, and examples of the substituent include a hydroxyl group, a carboxyl group, a cyano group, a nitro group, an alkyl group, a cycloalkyl group, an alkoxy group, an alkoxyalkyl group, an alkoxycarbonyl group, an alkoxycarbonyloxy group and the like. As for the substituent on the ring structure, a plurality of substituents may be present, and the substituents may be bonded to each other to form a ring (an aromatic or non-aromatic hydrocarbon ring, an aromatic or non-aromatic heterocyclic ring, a polycyclic condensed ring formed by combining two or more of these rings or the like).

In Formula (ZI-4), $R_{15}$ is preferably a methyl group, an ethyl group, a naphthyl group, a divalent group capable of forming a tetrahydrothiophene ring structure together with the sulfur atom by combining two $R_{15}$ with each other, and the like.

The substituent that $R_{13}$ and $R_{14}$ may have is preferably a hydroxyl group, an alkoxy group, an alkoxycarbonyl group or a halogen atom (particularly a fluorine atom).

l is preferably 0 or 1, and more preferably 1.

r is preferably 0 to 2.

The cation in the compound represented by Formula (ZI-4) in the present invention may be exemplified by the following specific examples.

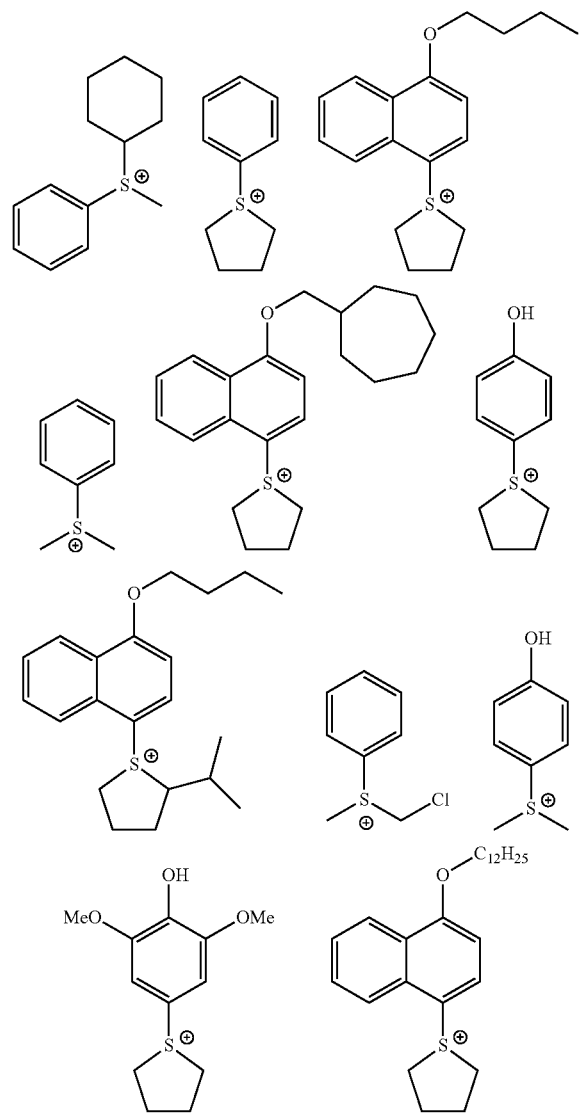

43
-continued
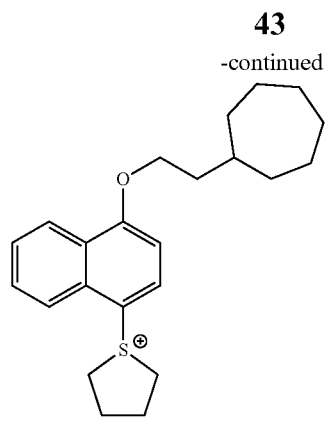
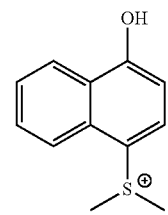
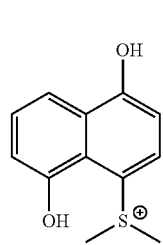
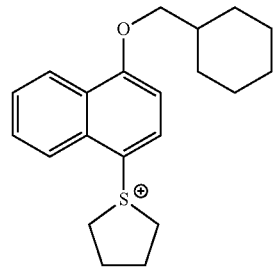
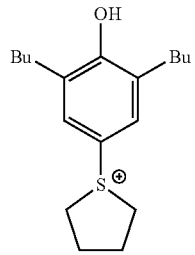
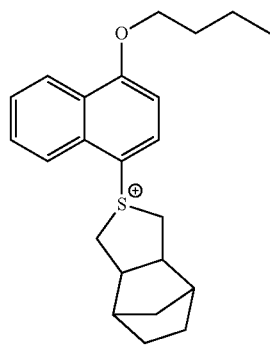
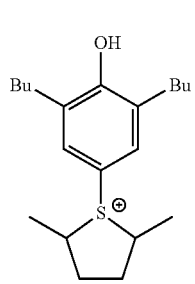
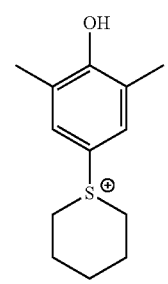
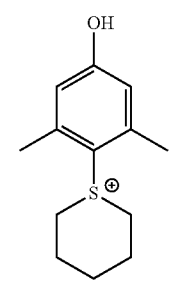
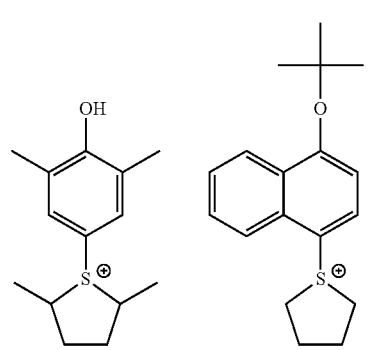
44
-continued
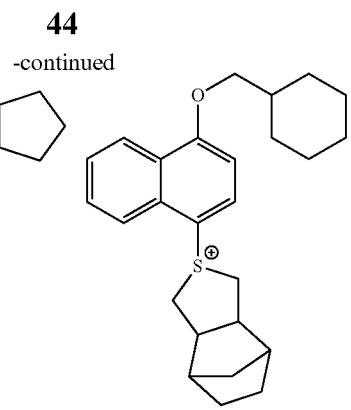
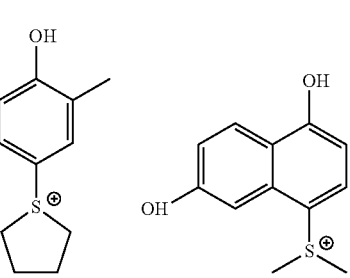
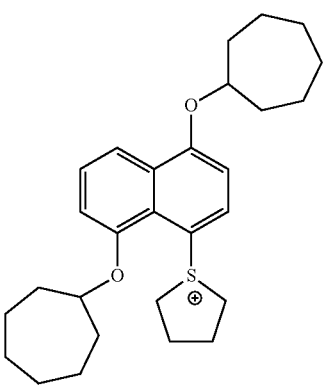
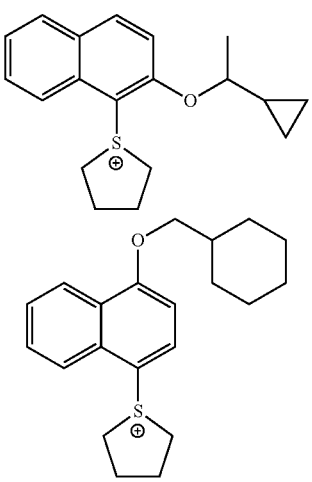

45
-continued
46
-continued
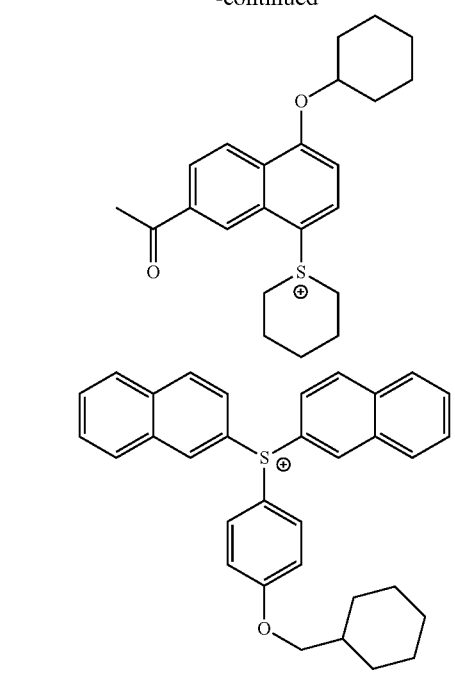
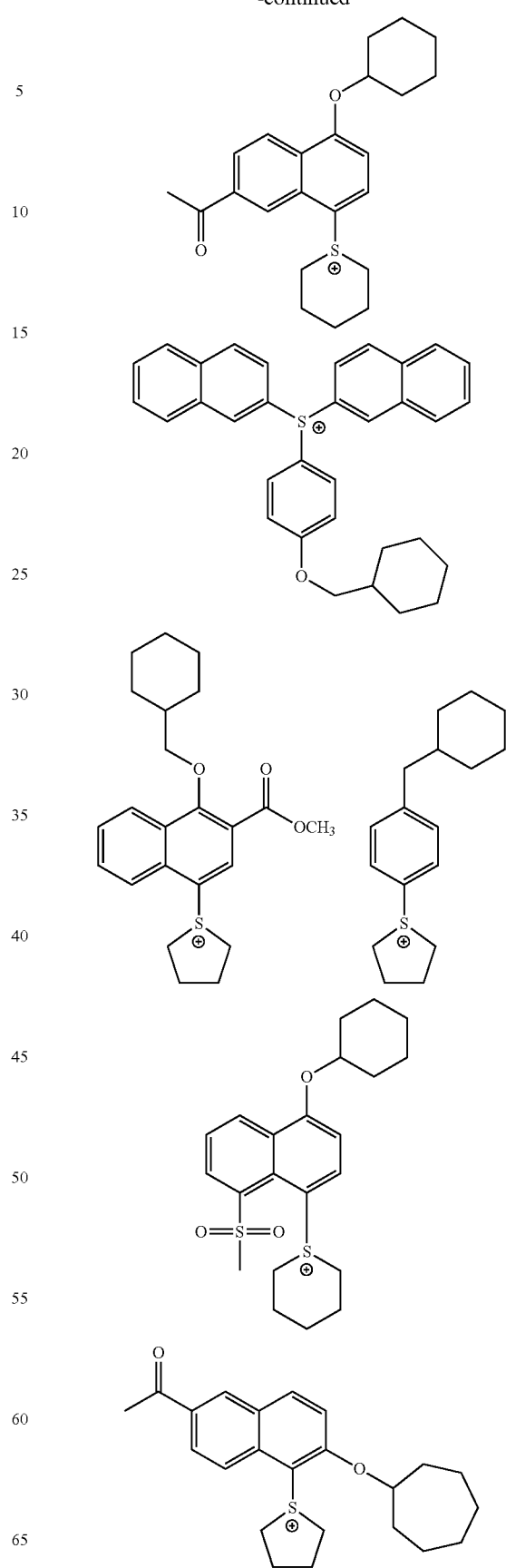

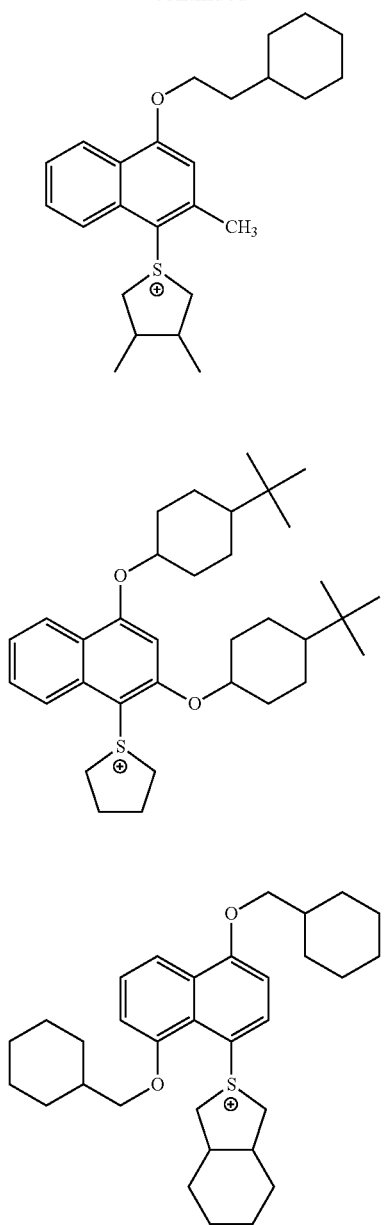
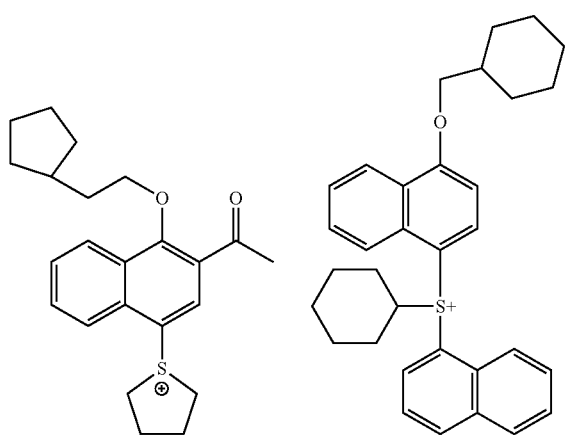
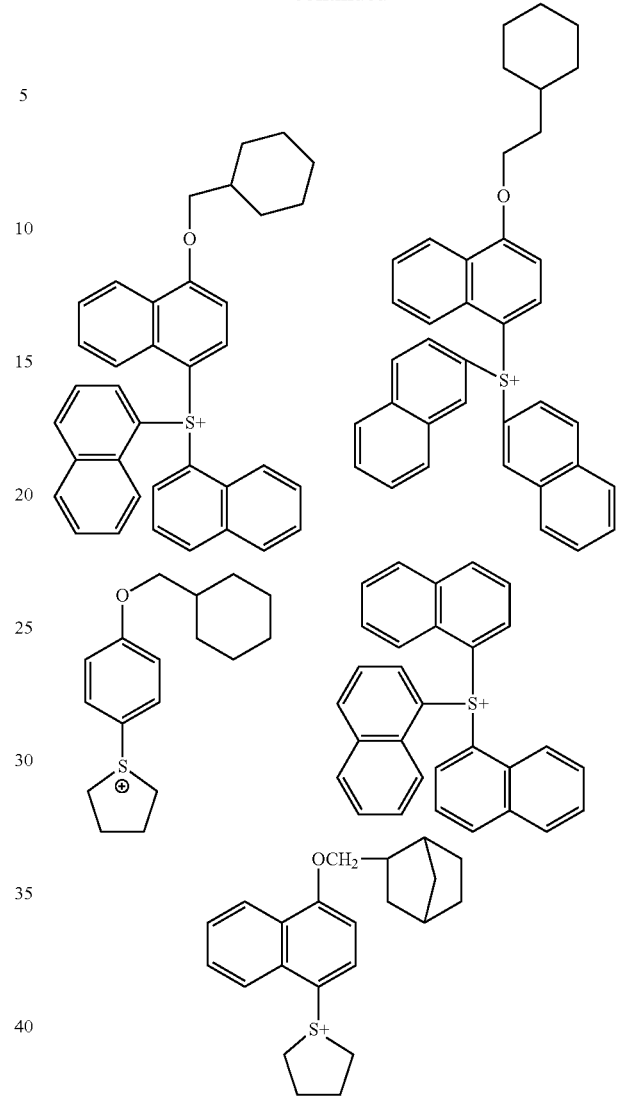

Next, Formulas (ZII) and (ZIII) will be described.

In Formulas (ZII) and (ZIII),

Each of $R_{204}$ to $R_{207}$ independently represents an aryl group, an alkyl group or a cycloalkyl group.

The aryl group of $R_{204}$ to $R_{207}$ is preferably a phenyl group or a naphthyl group, and more preferably a phenyl group. The aryl group of $R_{204}$ to $R_{207}$ may be an aryl group having a heterocyclic structure having an oxygen atom, a nitrogen atom, a sulfur atom or the like. Examples of the structure of the aryl group having a heterocyclic structure may include pyrrole, furan, thiophene, indole, benzofuran, benzothiophene and the like.

The alkyl group or the cycloalkyl group in $R_{204}$ to $R_{207}$ is preferably a straight or branched alkyl group having 1 to 10 carbon atoms (for example, a methyl group, an ethyl group, a propyl group, a butyl group and a pentyl group) and a cycloalkyl group having 3 to 10 carbon atoms (a cyclopentyl group, a cyclohexyl group and a norbornyl group).

The aryl group, the alkyl group and the cycloalkyl group of $R_{204}$ to $R_{207}$ may have a substituent. Examples of the substituent that the aryl group, the alkyl group and the cycloalkyl group of $R_{204}$ to $R_{207}$ may have include an alkyl group (for example, having 1 to 15 carbon atoms), a cycloalkyl group (for example, having 3 to 15 carbon atoms), an aryl group (for example, having 6 to 15 carbon atoms), an alkoxy group (for example, having 1 to 15 carbon atoms), a halogen atom, a hydroxyl group, a phenylthio group and the like.

$Z^-$ represents a non-nucleophilic anion, and examples thereof are the same as those of the non-nucleophilic anion of $Z^-$ in Formula (ZI).

Examples of the acid generator may further include compounds represented by the following Formulas (ZIV), (ZV) and (ZVI).

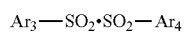
(ZIV)

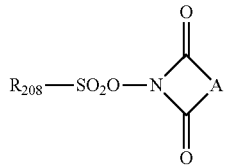
(ZV)

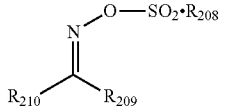
(ZVI)

In Formulas (ZIV) to (ZVI), each of $Ar_3$ and $Ar_4$ independently represents an aryl group.

Each of $R_{208}$, $R_{209}$ and $R_{210}$ independently represents an alkyl group, a cycloalkyl group or an aryl group.

A represents an alkylene group, an alkenylene group or an arylene group.

Specific examples of the aryl group of $Ar_3$, $Ar_4$, $R_{208}$, $R_{209}$ and $R_{210}$ are the same as specific examples of the aryl group as $R_{201}$, $R_{202}$ and $R_{203}$ in Formula (ZI-1).

Specific examples of the alkyl group and the cycloalkyl group of $R_{208}$, $R_{209}$ and $R_{210}$ are the same as specific examples of the alkyl group and the cycloalkyl group as $R_{201}$, $R_{202}$ and $R_{203}$ in Formula (ZI-2).

Examples of the alkylene group of A may include an alkylene group having 1 to 12 carbon atoms (for example, a methylene group, an ethylene group, a propylene group, an isopropylene group, a butylene group, an isobutylene group and the like), examples of the alkenylene group of A include an alkenylene group having 2 to 12 carbon atoms (for example, an ethenylene group, a propenylene group, a butenylene group and the like), and examples of the arylene group of A includes an arylene group having 6 to 10 carbon atoms (for example, a phenylene group, a tolylene group, a naphthylene group and the like).

Among the acid generators, the compounds represented by Formulas (ZI) to (ZIII) are more preferred.

In addition, the acid generator is preferably a compound capable of generating an acid having either a sulfonic acid group or an imide group, more preferably a compound capable of generating a monovalent perfluoroalkanesulfonic acid, a compound capable of generating an aromatic sulfonic acid substituted with a monovalent fluorine atom or a fluorine atom-containing group, or a compound capable of generating an imide acid substituted with a monovalent fluorine atom or a fluorine atom-containing group, and still more preferably a sulfonium salt of fluoro-substituted alkanesulfonic acid, fluorine-substituted benzenesulfonic acid, fluorine-substituted imide acid or fluorine-substituted methide acid. The acid generator which may be used is particularly preferably a fluoro-substituted alkanesulfonic acid, a fluoro-substituted benzenesulfonic acid or a fluoro-substituted imide acid, in which pKa of the acid generated is −1 or less, and the sensitivity is enhanced.

Among the acid generators, particularly preferred examples will be described below.

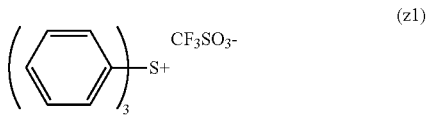
(z1)

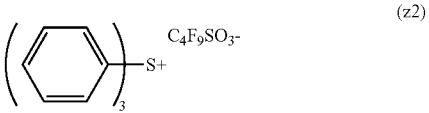
(z2)

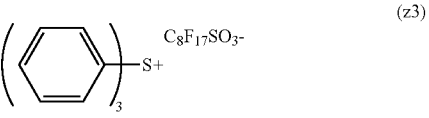
(z3)

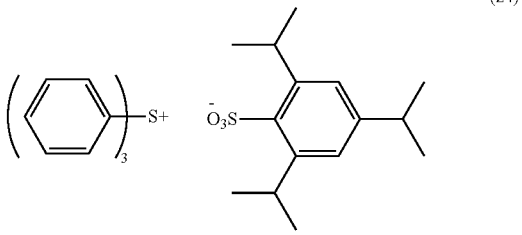
(z4)

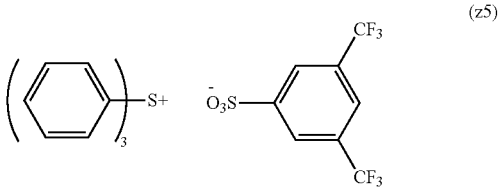
(z5)

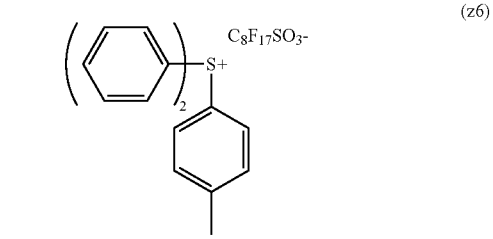
(z6)

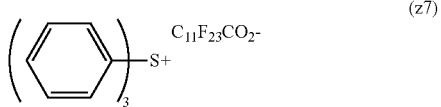
(z7)

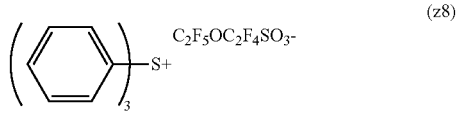
(z8)

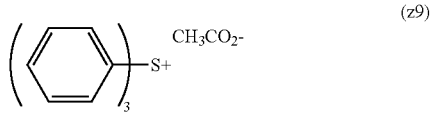
(z9)

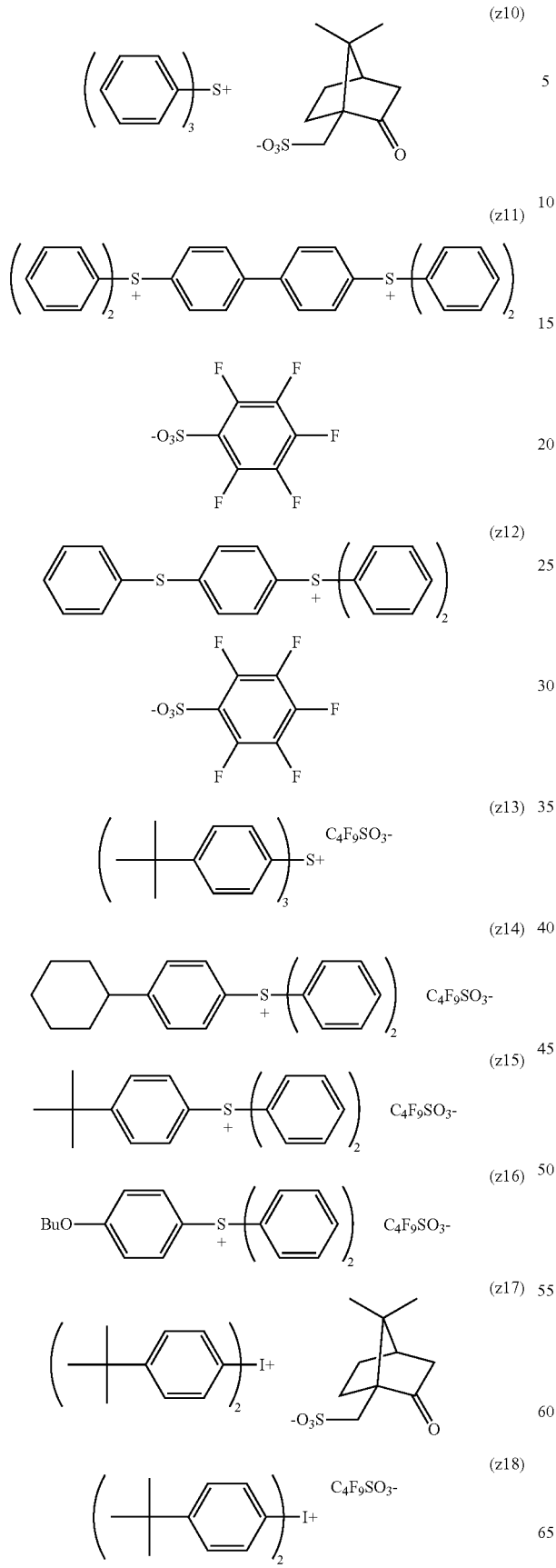
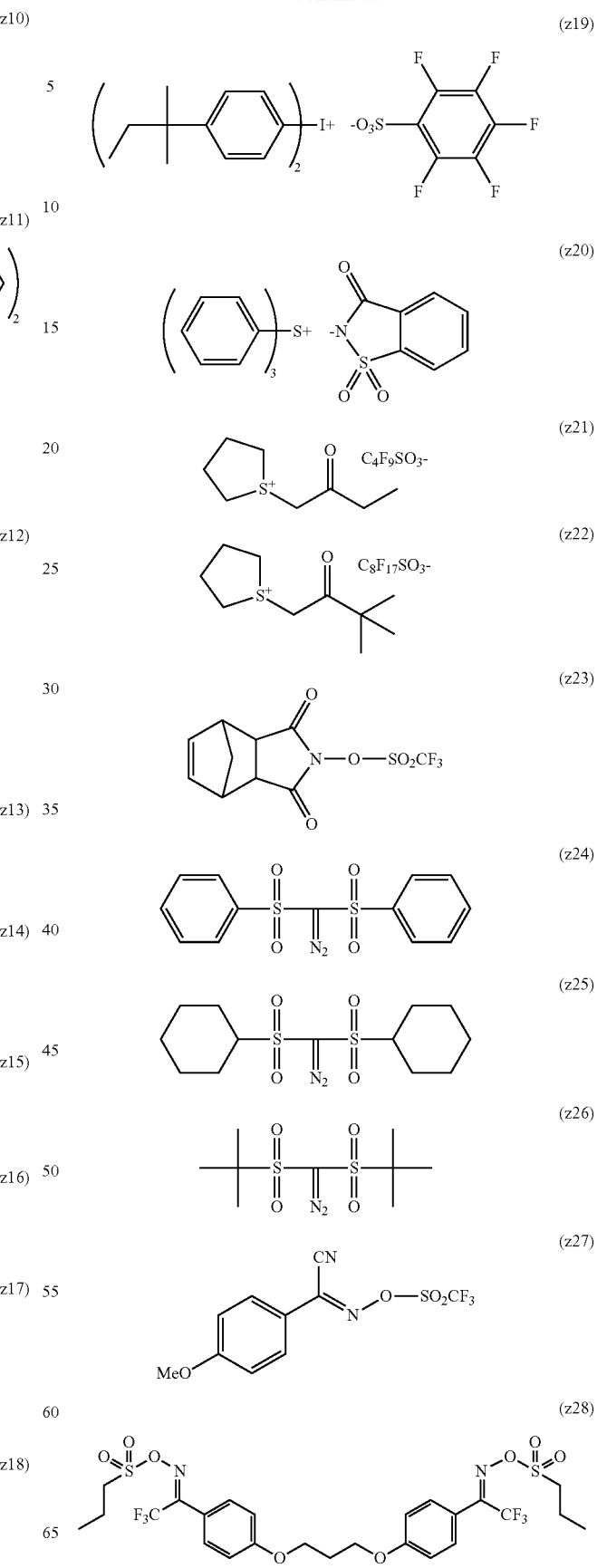

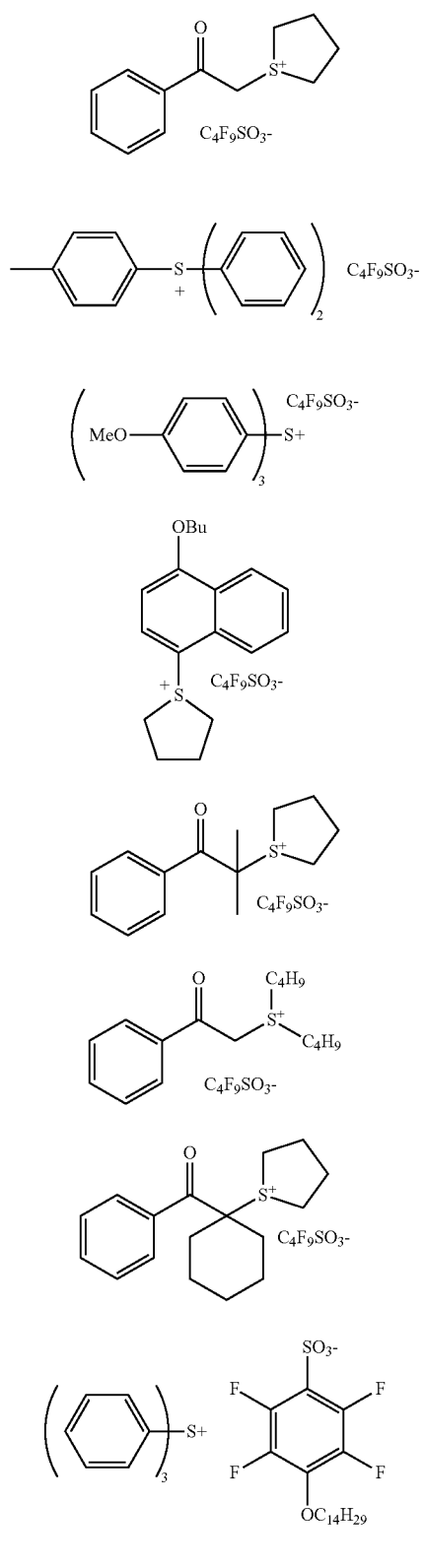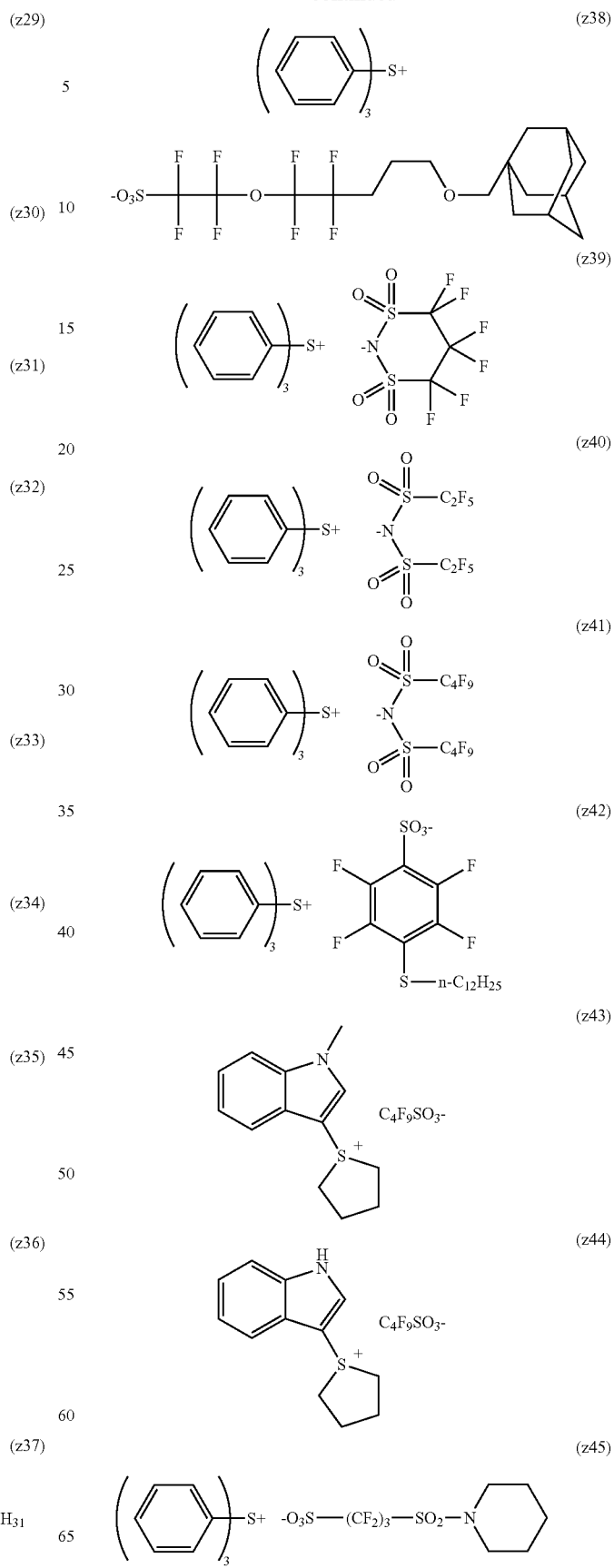

(z46) 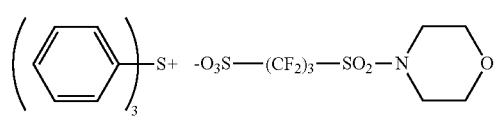
(z47) 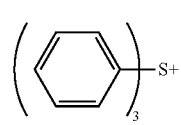
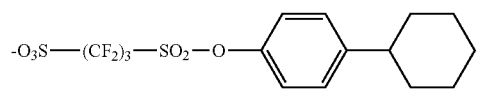
(z48) 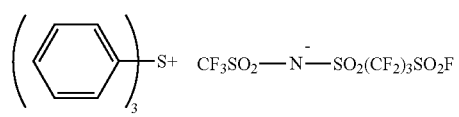
(z49) 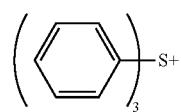
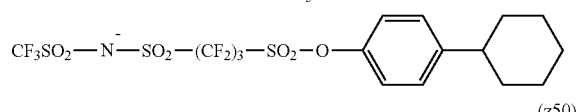
(z50) 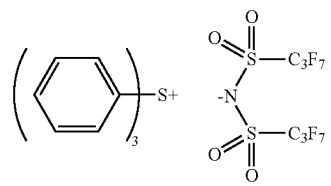
(z51) 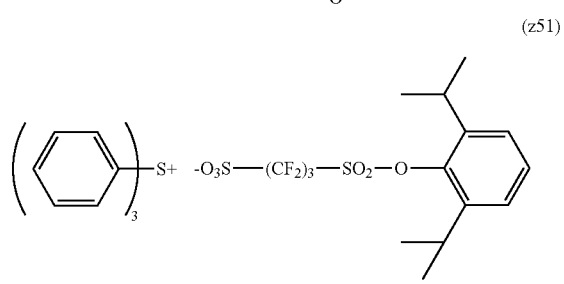
(z52) 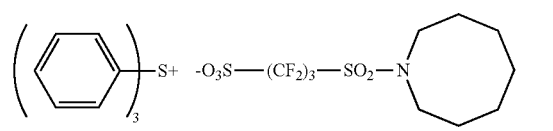
(z53) 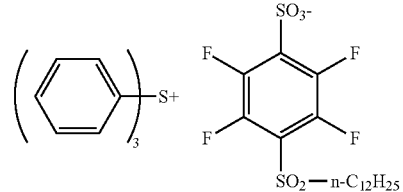
(z54) 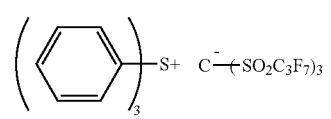
(z55) 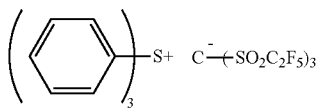
(z56) 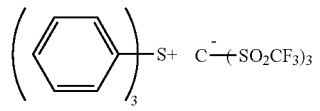
(z57) 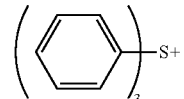
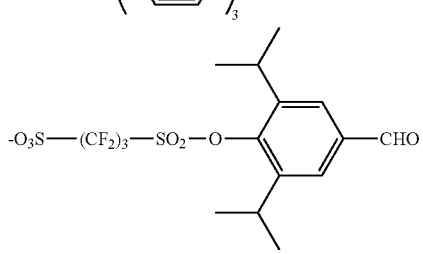
(z58) 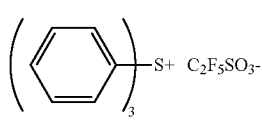
(z59) 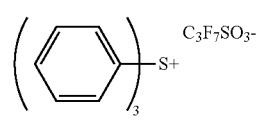
(z60) 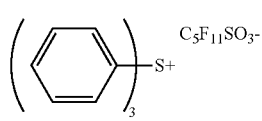
(z61) 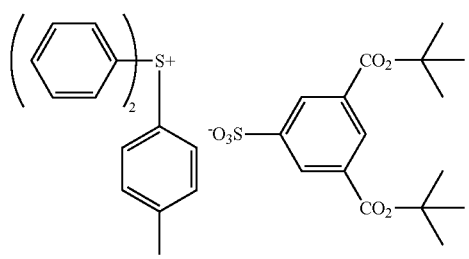
(z62) 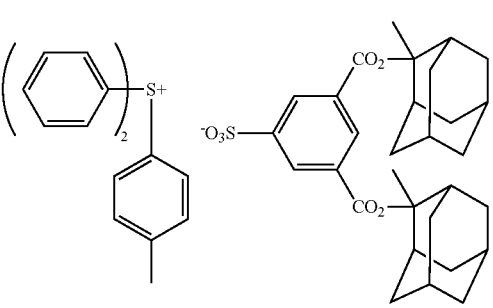
(z63) 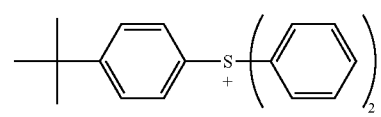

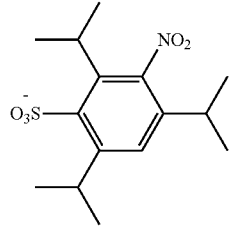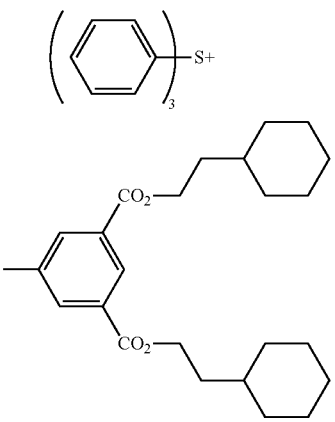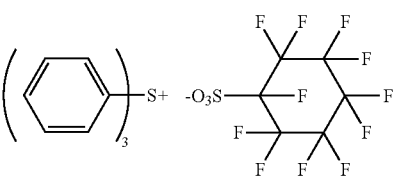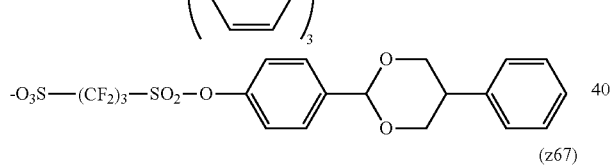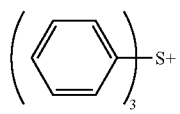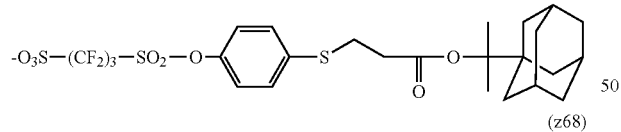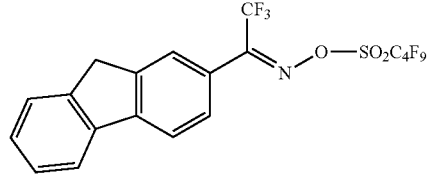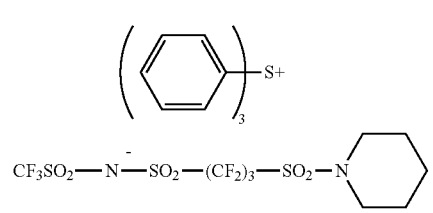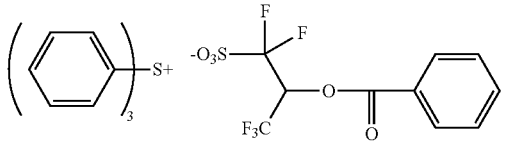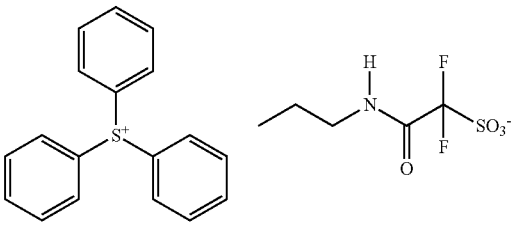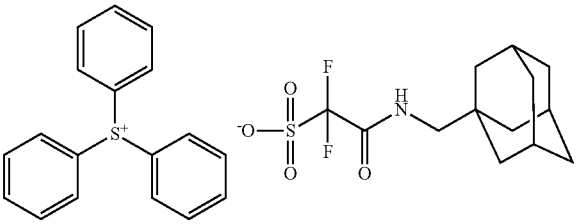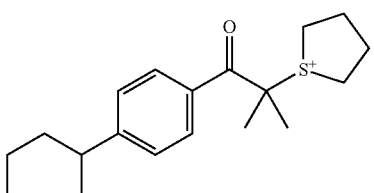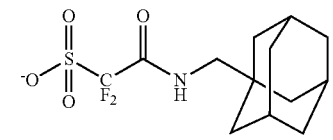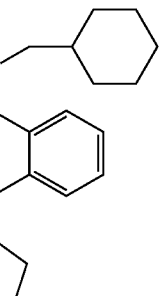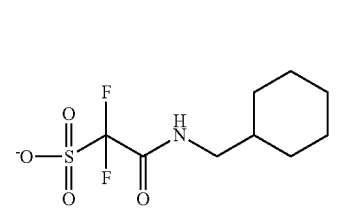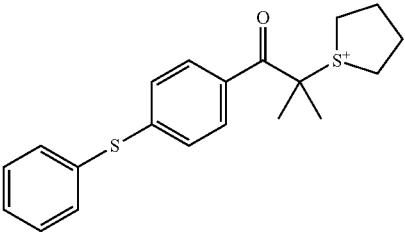

-continued
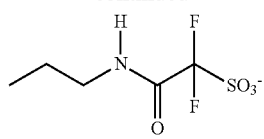
(z76)
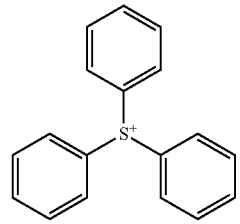
(z77)
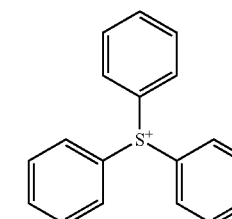
(z78)
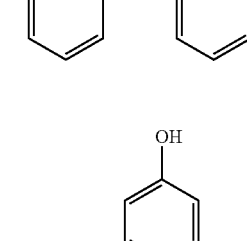
(z79)
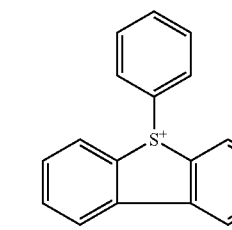
(z80)
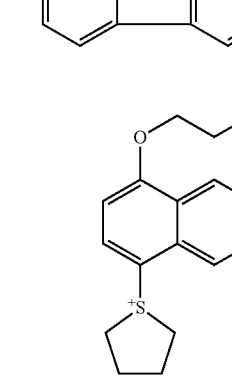
-continued
(z81)
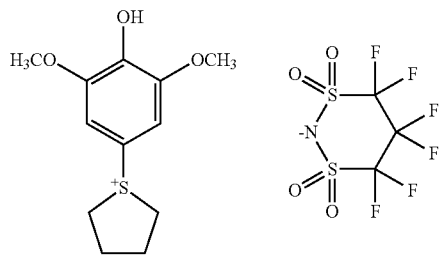
(z82)
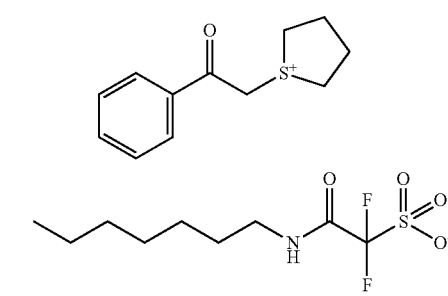
(z83)
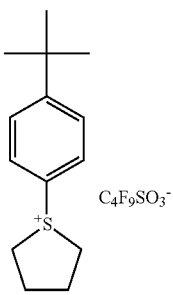
$C_4F_9SO_3^-$
(z84)
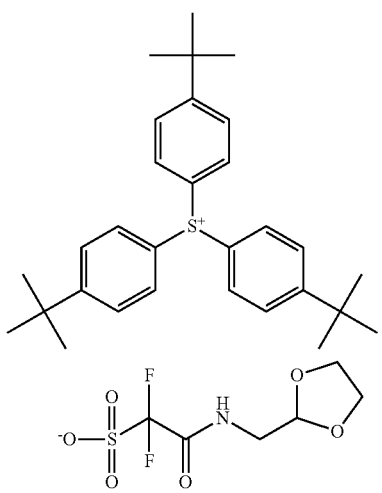
(z85)
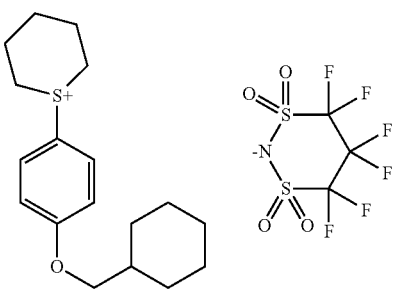

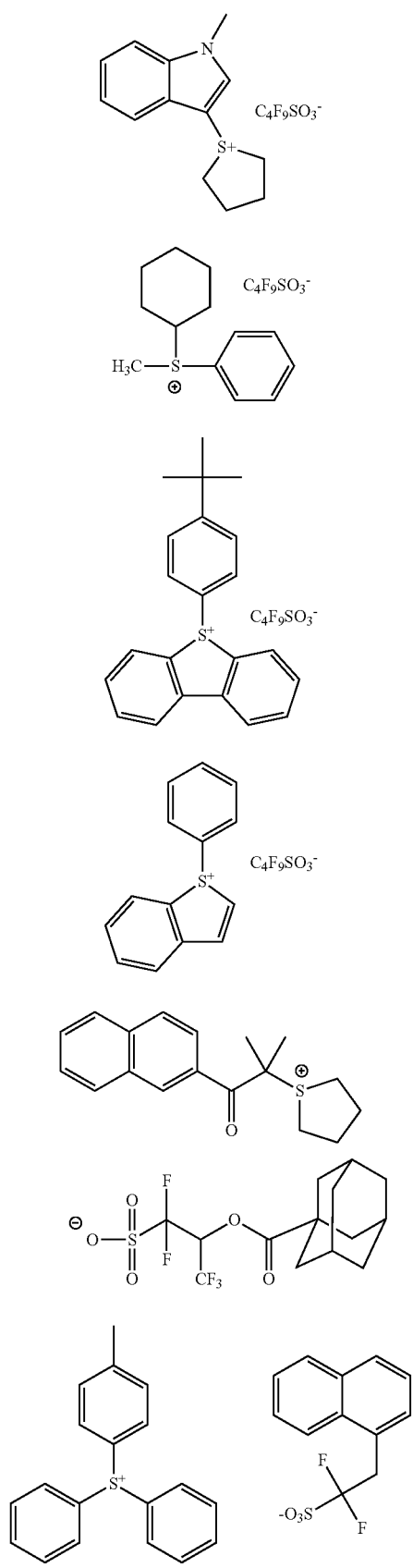
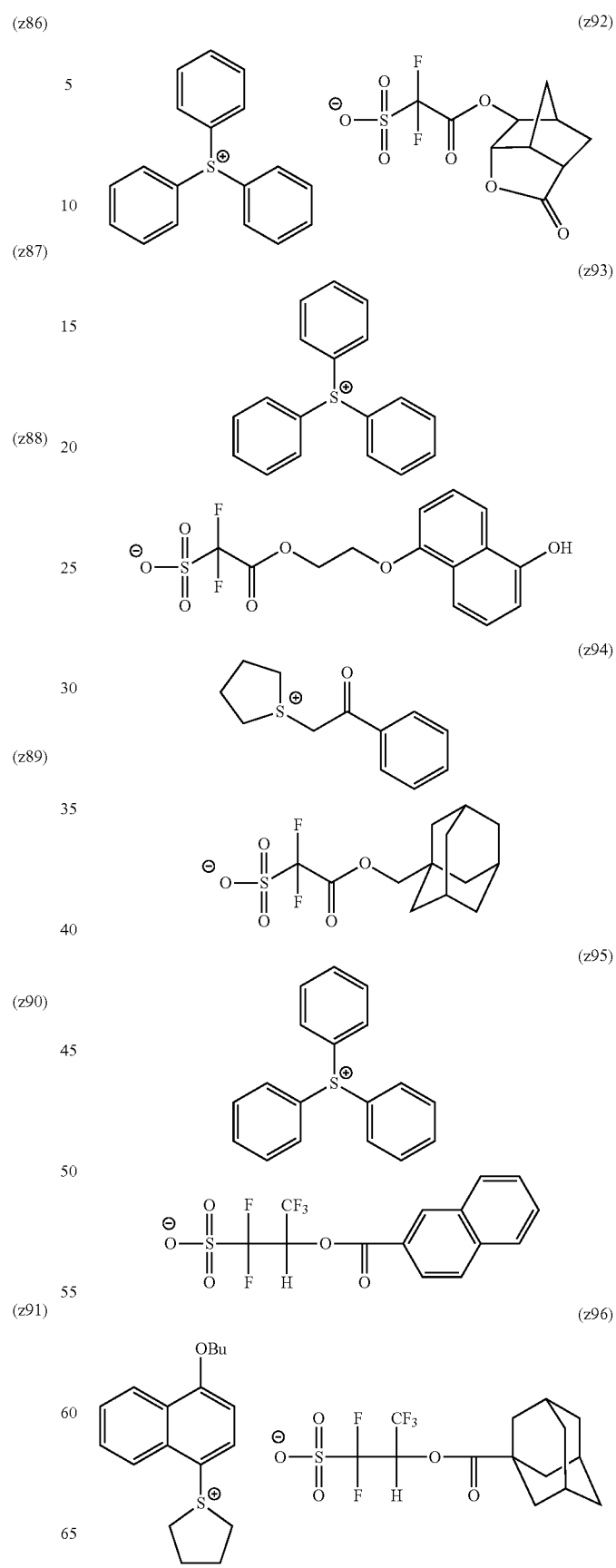

(z97)
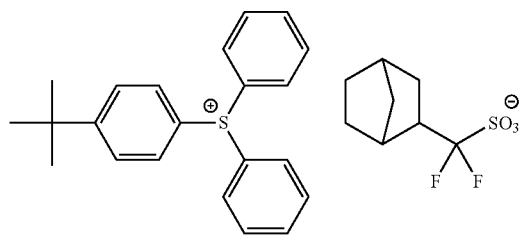
(z100)
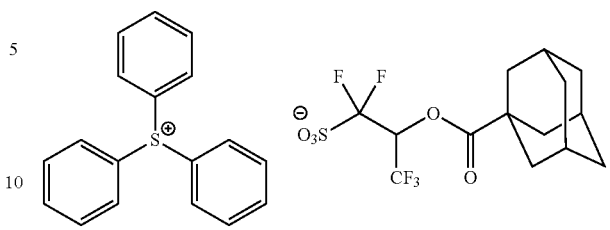
(z98)
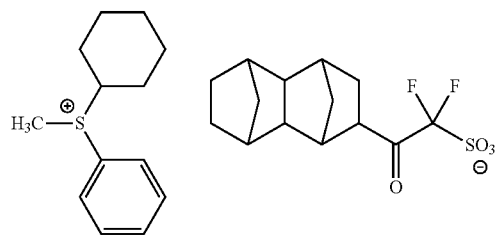
(z101)
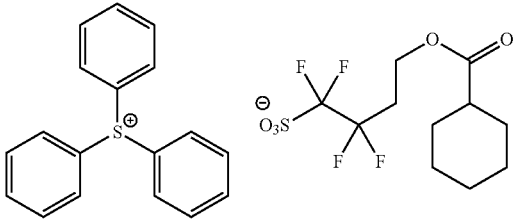
(z99)
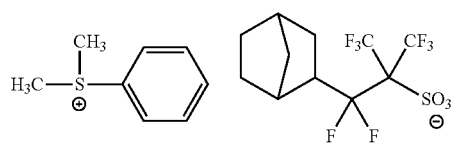
(z102)
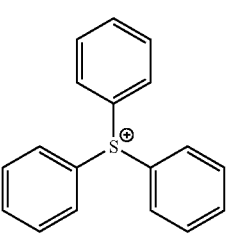
(z98)
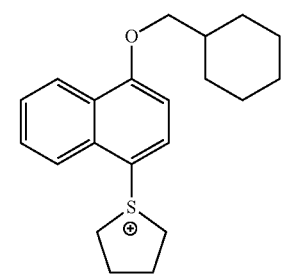
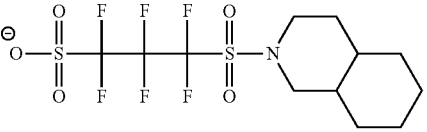
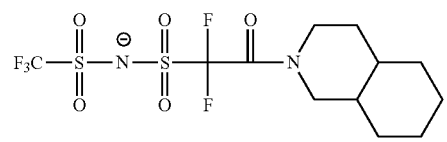
(z103)
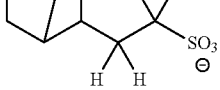
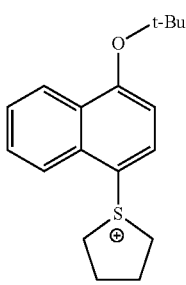
(z99)
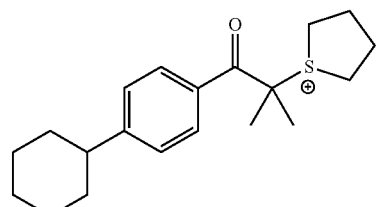
(z104)
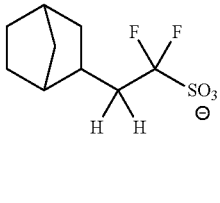
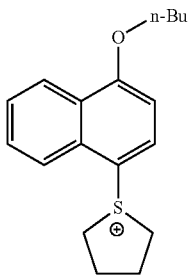
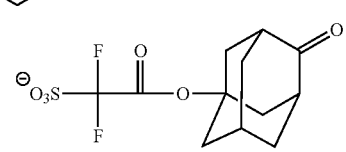

(z105) 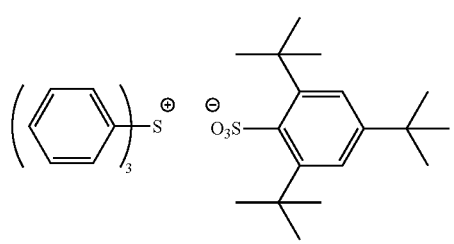
(z106) 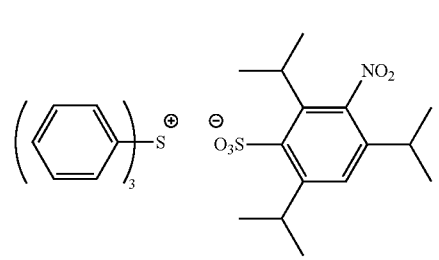
(z107) 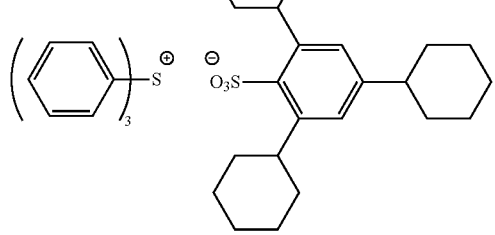
(z108) 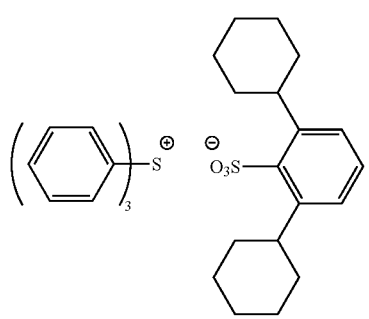
(z109) 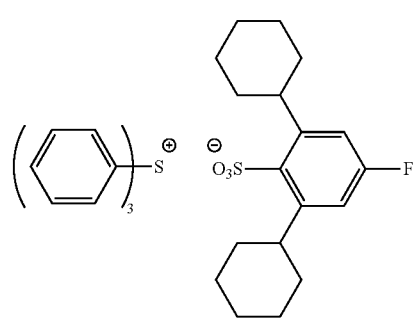
(z110) 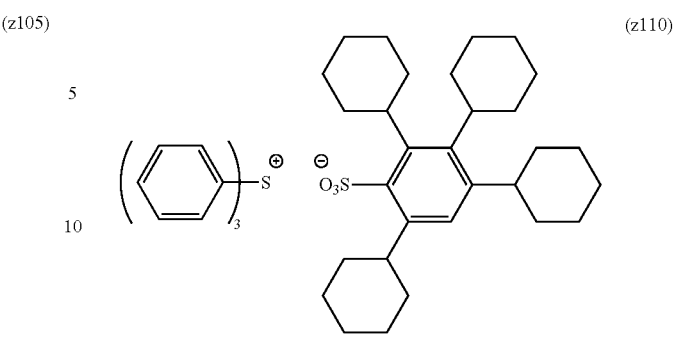
(z111) 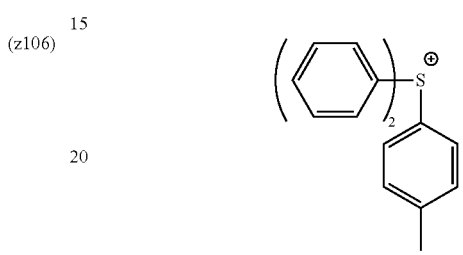
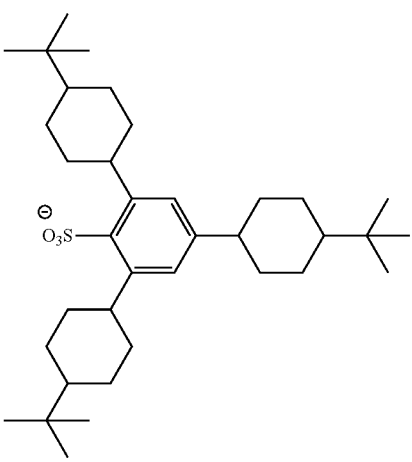
(z112) 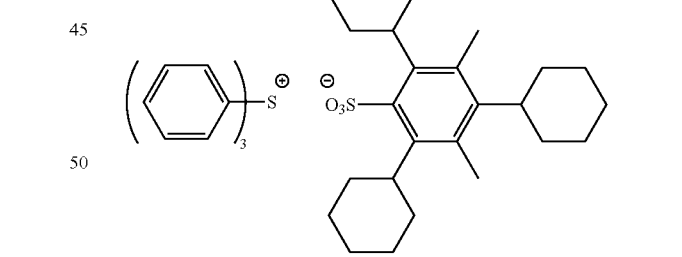
(z113) 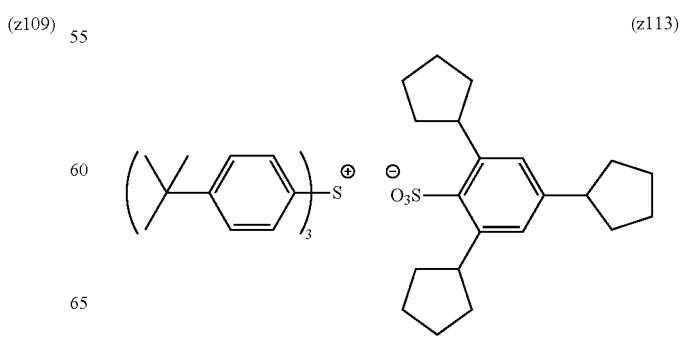

(z114)
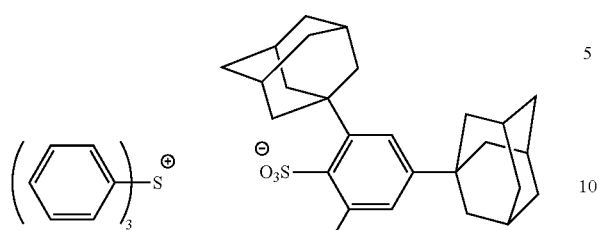
(z115)
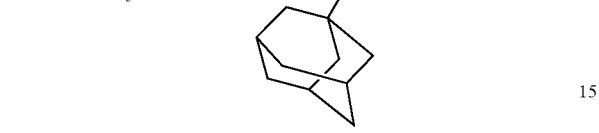
(z116)
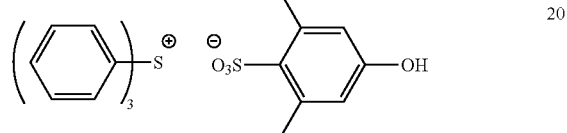
(z117)
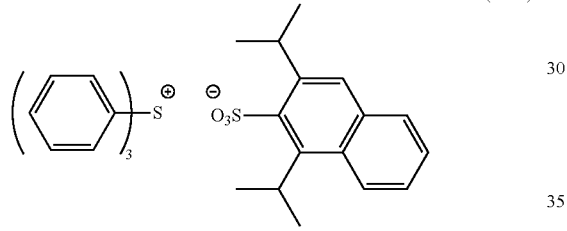
(z118)
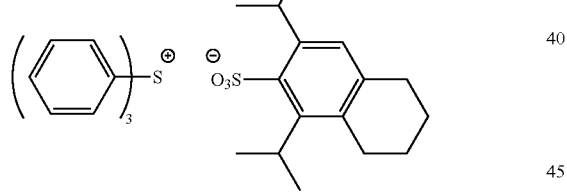
(z119)
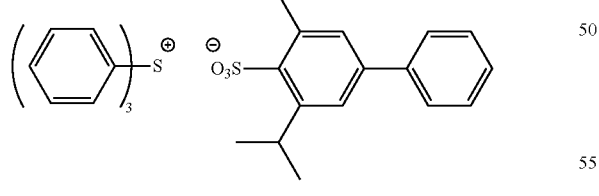
(z120)
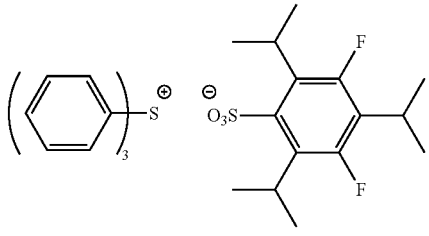
(z121)
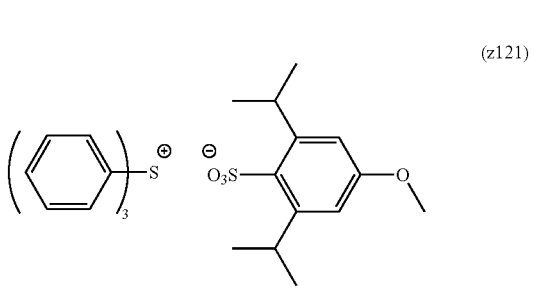
(z122)
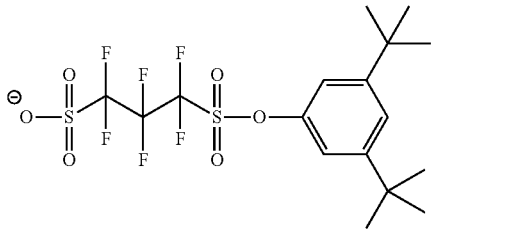
(z123)
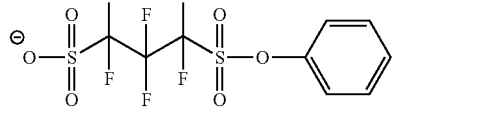
(z124)
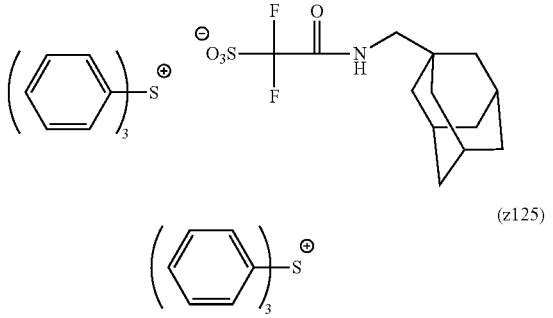
(z125)

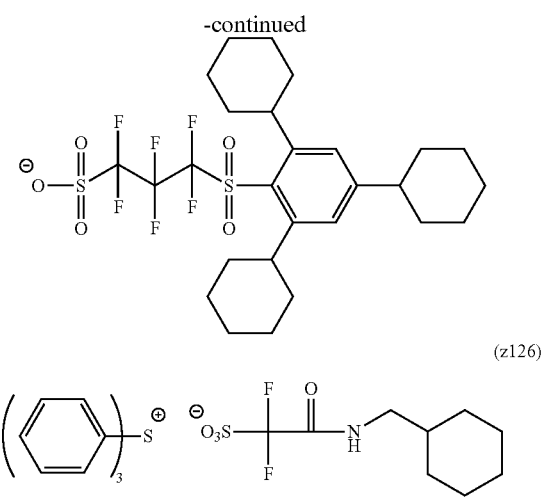

(z126)

The acid generator may be synthesized by a known method, and may be synthesized in accordance with the method described in, for example, Japanese Patent Application Laid-Open No. 2007-161707.

The acid generator may be used either alone or in combination of two or more thereof.

The content of the compound capable of generating an acid upon irradiation with an actinic ray or radiation in the composition is preferably 0.1% by mass to 40% by mass, more preferably 1% by mass to 30% by mass, still more preferably 5% by mass to 25% by mass, based on the total solid of the actinic ray-sensitive or radiation-sensitive resin composition.

[3] (C) Solvent

Examples of the solvent which may be used at the time of preparing the resist composition in the present invention may include an organic solvent such as alkylene glycol monoalkyl ether carboxylate, alkylene glycol monoalkyl ether, alkyl ester lactate, alkyl alkoxypropionate, cyclic lactone (preferably having 4 to 10 carbon atoms), a monoketone compound (preferably having 4 to 10 carbon atoms) which may have a ring, alkylene carbonate, alkyl alkoxyacetate and alkyl pyruvate.

Specific examples of these solvents may include those described in [0441] to [0455] of U.S. Patent Application Publication No. 2008/0187860.

The present invention may use a mixed solvent of a solvent containing a hydroxyl group and a solvent containing no hydroxyl group in the structure as an organic solvent.

As a solvent containing a hydroxyl group and a solvent containing no hydroxyl group, the above-mentioned compound may be appropriately selected, and the solvent containing a hydroxyl group is preferably alkylene glycol monoalkyl ether, alkyl lactate and the like, and more preferably propylene glycol monomethyl ether (PGME, another name 1-methoxy-2-propanol) or ethyl lactate. Further, the solvent containing no hydroxyl group is preferably alkylene glycol monoalkyl ether acetate, alkyl alkoxypropionate, a monoketone compound which may contain a ring, cyclic lactone, alkyl acetate and the like, and among them, particularly preferably propylene glycol monomethyl ether acetate (PGMEA, another name 1-methoxy-2-acetoxypropane), ethyl ethoxypropionate, 2-heptanone, γ-butyrolactone, cyclohexanone or butyl acetate, and most preferably propylene glycol monomethyl ether acetate, ethylethoxy propionate or 2-heptanone.

The mixing ratio (by mass) of the solvent containing a hydroxyl group to the solvent containing no hydroxyl group is 1/99 to 99/1, preferably 10/90 to 90/10, and more preferably 20/80 to 60/40. A mixed solvent in which the solvent containing no hydroxyl group is contained in an amount of 50% by mass or more is particularly preferred in view of coating uniformity.

The solvent preferably contains propylene glycol monomethyl ether acetate, and is preferably a propylene glycol monomethyl ether acetate sole solvent, or a mixed solvent of two kinds or more containing propylene glycol monomethyl ether acetate.

[4] (D) Basic Compound

The resist composition in the present invention may contain (D) a basic compound in order to reduce the change in performance over time from exposure to heating.

Preferred examples of the basic compounds include compounds having a structure represented by the following Formulas (A) to (E).

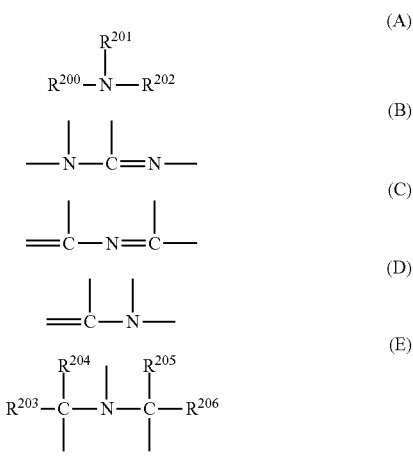

In Formulas (A) to (E),

Each of $R^{200}$, $R^{201}$ and $R^{202}$ may be the same as or different from each other of $R^{200}$, $R^{201}$ and $R^{202}$ and represents a hydrogen atom, an alkyl group (preferably having 1 to 20 carbon atoms), a cycloalkyl group (preferably having 3 to 20 carbon atoms) or an aryl group (having 6 to 20 carbon), and $R^{201}$ and $R^{202}$ may be bonded to each other to form a ring. Each of $R^{203}$, $R^{204}$, $R^{205}$ and $R^{206}$ may be the same as or different from each other of $R^{203}$, $R^{204}$, $R^{205}$ and $R^{206}$ and represents an alkyl group having 1 to 20 carbon atoms.

As for the alkyl group, the alkyl group having a substituent is preferably an aminoalkyl group having 1 to 20 carbon atoms, a hydroxyalkyl group having 1 to 20 carbon atoms or a cyanoalkyl group having 1 to 20 carbon atoms.

The alkyl group in Formulas (A) to (E) is more preferably unsubstituted.

Preferred examples of the compound may include guanidine, aminopyrrolidine, pyrazole, pyrazoline, piperazine, aminomorpholine, aminoalkylmorpholine, piperidine and the like, and more preferred examples of the compound include a compound having an imidazole structure, a diazabicyclo structure, an onium hydroxide structure, an onium carboxylate structure, a trialkylamine structure, an aniline structure or a pyridine structure, an alkylamine derivative having a hydroxyl group and/or an ether bond, an aniline derivative having a hydroxyl group and/or an ether bond and the like.

Examples of the compound having an imidazole structure may include imidazole, 2,4,5-triphenylimidazole, benzimidazole and the like. Examples of the compound having a diazabicyclo structure may include 1,4-diazabicyclo[2,2,2]octane, 1,5-diazabicyclo[4,3,0]non-5-ene and 1,8-diazabicyclo[5,4,0]undec-7-ene. Examples of the compound having an onium hydroxide structure may include triarylsulfonium hydroxide, phenacylsulfonium hydroxide, a sulfonium hydroxide having a 2-oxoalkyl group, specifically, triphenylsulfonium hydroxide, tris(t-butylphenyl)sulfonium hydroxide, bis(t-butylphenyl)iodonium hydroxide, phenacylthiophenium hydroxide, 2-oxopropylthiophenium hydroxide and the like. Examples of the compound having an onium carboxylate structure may include a compound, in which the anion moiety of a compound having an onium hydroxide structure has been converted into carboxylate, such as acetate, adamantane-1-carboxylate and perfluoroalkylcarboxylate. Examples of the compound having a trialkylamine structure may include tri(n-butyl)amine, tri(n-octyl)amine and the like. Examples of the compound having an aniline structure may include 2,6-diisopropylaniline, N,N-dimethylaniline, N,N-dibutylaniline, N,N-dihexylaniline and the like. Examples of the alkylamine derivative having a hydroxyl group and/or an ether bond may include ethanolamine, diethanolamine, triethanolamine, tris(methoxyethoxyethyl)amine and the like. Examples of the aniline derivative having a hydroxyl group and/or an ether bond may include N,N-bis(hydroxyethyl)aniline and the like.

Examples of the preferred basic compound may further include an amine compound having a phenoxy group, an ammonium salt compound having a phenoxy group, an amine compound having a sulfonic acid ester group, and an ammonium salt compound having a sulfonic acid ester group.

It is preferred that the amine compound having a phenoxy group, the ammonium salt compound having a phenoxy group, the amine compound having a sulfonic acid ester group, and the ammonium salt compound having a sulfonic acid ester group have at least one alkyl group bonded to a nitrogen atom. Further, it is preferred that the alkyl chain has an oxygen atom therein to form an oxyalkylene group. The number of the oxyalkylene groups is one or more, preferably 3 to 9, and more preferably 4 to 6, in the molecule. Among the oxyalkylene groups, the structures of —CH$_2$CH$_2$O—, CH(CH$_3$)CH$_2$O— or —CH$_2$CH$_2$CH$_2$O— are preferred.

Specific examples of the amine compound having a phenoxy group, the ammonium salt compound having a phenoxy group, the amine compound having a sulfonic acid ester group, and the ammonium salt compound having a sulfonic acid ester group may include compounds (C1-1) to (C3-3) as exemplified in [0066] of US Patent Application Publication No. 2007/0224539, but are not limited thereto.

Further, a nitrogen-containing organic compound having a group capable of leaving by the action of an acid may also be used as a kind of basic compound. Examples of the compound may include a compound represented by the following Formula (F). In addition, the compound represented by the following Formula (F) exhibits an effective basicity in the system as a result of elimination of the group capable of leaving by the action of an acid.

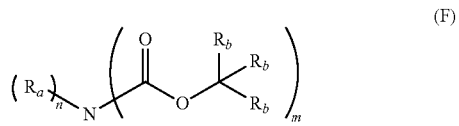

(F)

In Formula (F), each Ra independently represents a hydrogen atom, an alkyl group, a cycloalkyl group, an aryl group or an aralkyl group. Further, when n=2, each of two Ra's may be the same as or different from each other of Ra's, and two Ra's may be bonded to each other to form a divalent heterocyclic hydrocarbon group (preferably having 20 or less carbon atoms) or a derivative thereof.

Each Rb independently represents a hydrogen atom, an alkyl group, a cycloalkyl group, an aryl group or an aralkyl group. However, in —C(R$_b$)(R$_b$)(R$_b$), when one or more R$_b$ are a hydrogen atom, at least one of the remaining R$_b$ is a cyclopropyl group or a 1-alkoxy alkyl group.

At least two R$_b$ may be bonded to each other to form an alicyclic hydrocarbon group, an aromatic hydrocarbon group, a heterocyclic hydrocarbon group or a derivative thereof.

n represents an integer of 0 to 2, m represents an integer of 1 to 3, and n+m=3.

In Formula (F), each of the alkyl group, the cycloallyl group, the aryl group and the aralkyl group represented by R$_a$ and R$_b$ may be substituted with a functional group such as a hydroxyl group, a cyano group, an amino group, a pyrrolidino group, a piperidino group, a morpholino group and an oxo group, an alkoxy group or a halogen atom.

Examples of the alkyl group, the cycloalkyl group, the aryl group or the aralkyl group (each of the alkyl group, the cycloalkyl group, the aryl group and the aralkyl group may be substituted with the functional group, an alkoxy group or a halogen atom) of R may include a group derived from a straight or branched alkane such as methane, ethane, propane, butane, pentane, hexane, heptane, octane, nonane, decane, undecane and dodecane, a group in which the group derived from the alkane is substituted with one or more kinds of or one or more groups of cycloalkyl groups such as, for example, a cyclobutyl group, a cyclopentyl group and a cyclohexyl group, a group derived from a cycloalkane such as cyclobutane, cyclopentane, cyclohexane, cycloheptane, cyclooctane, norbornane, adamantane and noradamantane, a group where the group derived from the cycloalkane is substituted with one or more kinds of or one or more groups of straight or branched alkyl groups such as, for example, a methyl group, an ethyl group, an n-propyl group, an i-propyl group, an n-butyl group, a 2-methylpropyl group, a 1-methylpropyl group and a t-butyl group, a group derived from an aromatic compound such as benzene, naphthalene and anthracene, a group in which the group derived from the aromatic compound is substituted with one or more kinds of or one or more groups of straight or branched alkyl groups such as, for example, a methyl group, an ethyl group, an n-propyl group, an i-propyl group, an n-butyl group, a 2-methylpropyl group, a 1-methylpropyl group and a t-butyl group, and a group derived from a heterocyclic compound such as pyrrolidine, piperidine, morpholine, tetrahydrofuran, tetrahydropyran, indole, indoline, quinoline, perhydroquinoline, indazole and benzimidazole, a group in which the group derived from the heterocyclic compound is substituted with one or more kinds of or one or more groups of straight or branched alkyl groups or groups derived from aromatic compounds, a group in which the group derived from a straight or branched alkane or the group derived from a cycloalkane is substituted with one or more kinds of or one or more groups of groups derived from aromatic compounds, such as a phenyl group, a naphthyl group and an anthracenyl group, a group in which the above-described substituent is substituted with a functional group such as a hydroxyl group, a cyano group, an amino group, a pyrrolidino group, a piperidino group, a morpholino group and an oxo group, and the like.

Further, examples of the divalent heterocyclic hydrocarbon group (preferably having 1 to 20 carbon atoms) formed by combining $R_a$ with each other or a derivative thereof may include a group derived from a heterocyclic compound such as pyrrolidine, piperidine, morpholine, 1,4,5,6-tetrahydropyrimidine, 1,2,3,4-tetrahydroquinoline, 1,2,3,6-tetrahydropyridine, homopiperazine, 4-azabenzimidazole, benzotriazole, 5-azabenzotriazole, 1H-1,2,3-triazole, 1,4,7-triazacyclononane, tetrazole, 7-azaindole, indazole, benzimidazole, imidazo[1,2-a]pyridine, (1S,4S)-(+)-2,5-diazabicyclo[2.2.1]heptane, 1,5,7-triazabicyclo[4.4.0]dec-5-ene, indole, indoline, 1,2,3,4-tetrahydroquinoxaline, perhydroquinoline and 1,5,9-triazacyclododecane, a group in which the group derived from the heterocyclic compound is substituted with one or more kinds of or one or more groups of straight chained or branched groups derived from alkane, groups derived from cycloalkane, groups derived from aromatic compounds, groups derived from heterocyclic compounds and functional groups such as a hydroxyl group, a cyano group, an amino group, a pyrrolidino group, a piperidino group, a morpholino group and an oxo group.

Specifically, particularly preferred examples thereof in the present invention may include N-t-butoxycarbonyldi-n-octylamine, N-t-butoxycarbonyldi-n-nonylamine, N-t-butoxycarbonyldi-n-decylamine, N-t-butoxycarbonyldicyclohexylamine, N-t-butoxycarbonyl-1-adamantylamine, N-t-butoxycarbonyl-2-adamantylamine, N-t-butoxycarbonyl-N-methyl-1-adamantylamine, (S)-(−)-1-(t-butoxycarbonyl)-2-pyrrolidinemethanol, (R)-(+)-1-(t-butoxycarbonyl)-2-pyrrolidinemethanol, N-t-butoxycarbonyl-4-hydroxypiperidine, N-t-butoxycarbonylpyrrolidine, N-t-butoxycarbonylmorpholine, N-t-butoxycarbonylpiperazine, N,N-di-t-butoxycarbonyl-1-adamantylamine, N,N-di-t-butoxycarbonyl-N-methyl-1-adamantylamine, N-t-butoxycarbonyl-4,4'-diaminodiphenylmethane, N,N'-di-t-butoxycarbonylhexamethylenediamine, N,N,N'N'-tetra-t-butoxycarbonylhexamethylenediamine, N,N'-di-t-butoxycarbonyl-1,7-diaminoheptane, N,N'-di-t-butoxycarbonyl-1,8-diaminooctane, N,N'-di-t-butoxycarbonyl-1,9-diaminononane, N,N'-di-t-butoxycarbonyl-1,10-diaminodecane, N,N'-di-t-butoxycarbonyl-1,12-diaminododecane, N,N'-di-t-butoxycarbonyl-4,4'-diaminodiphenylmethane, N-t-butoxycarbonylbenzimidazole, N-t-butoxycarbonyl-2-methylbenzimidazole, N-t-butoxycarbonyl-2-phenylbenzimidazole and the like.

The compound represented by Formula (F) may be synthesized in accordance with the methods as described in Japanese Patent Application Laid-Open No. 2009-199021 and Japanese Patent Application Laid-Open No. 2007-298569.

The molecular weight of the basic compound is preferably 250 to 2,000, and more preferably 400 to 1,000. From the viewpoint of more reduction in LWR and uniformity of local pattern dimension, the molecular weight of the basic compound is preferably 400 or more, more preferably 500 or more, and still more preferably 600 or more.

These basic compounds may be used either alone or in combination of two or more thereof.

The amount of the basic compound used is usually 0.001% by mass to 10% by mass, and preferably 0.01% by mass to 5% by mass, based on the solid of the resist composition.

The ratio of the acid generator and the basic compound used in the composition is preferably acid generator/basic compound (molar ratio)=2.5 to 300. That is, the molar ratio is preferably 2.5 or more in view of sensitivity, resolution and the like, and is preferably 300 or less from the viewpoint of suppressing the reduction in resolution caused by thickening of the resist pattern over time after exposure until heat treatment. The acid generator/basic compound (molar ratio) is more preferably 5.0 to 200, and still more preferably 7.0 to 150.

[5] (E) Surfactant

The resist composition in the present invention may or may not further contain a surfactant, but in the case of containing a surfactant, it is more preferred that the composition contains any one of fluorine and/or silicon-based surfactants (a fluorine-based surfactant, a silicon-based surfactant and a surfactant having both a fluorine atom and a silicon atom), or two or more thereof.

The resist composition in the present invention contains a surfactant, thereby imparting a resist pattern with adhesion and reduced development defect due to improved sensitivity and resolution when using an exposure light source with a wavelength of 250 nm or less, particularly 220 nm or less.

Examples of the fluorine-based and/or silicon-based surfactants include surfactants described in [0276] of U.S. Patent Application Publication No. 2008/0248425, such as EFtop EF301 and EF303 (manufactured by Shin-Akita Kasei Co., Ltd.), Florad FC430, 431 and 4430 (manufactured by Sumitomo 3M Inc.), Megaface F171, F173, F176, F189, F113, F110, F177, F120 and R08 (manufactured by DIC Corporation), Surflon S-382, SC101, 102, 103, 104, 105 and 106 and KH-20 (manufactured by Asahi Glass Co., Ltd.), Troysol S-366 (manufactured by Troy Chemical Corp.), GF-300 and GF-150 (manufactured by Toagosei Chemical Industry Co., Ltd.), Surflon S-393 (manufactured by Seimi Chemical Co., Ltd.), EFtop EF121, EF122A, EF122B, RF122C, EF125M, EF135M, EF351, EF352, EF801, EF802 and EF601 (manufactured by JEMCO Co., Ltd.), PF636, PF656, PF6320 and PF6520 (manufactured by OMNOVA Solutions, Inc.), and FTX-204G, 208G, 218G, 230G, 204D, 208D, 212D, 218D and 222D (manufactured by NEOS Co., Ltd.). Further, polysiloxane polymer KP-341 (manufactured by Shin-Etsu Chemical Co., Ltd.) may also be used as the silicon-based surfactant.

Further, other than those known surfactants described above, it is possible to use a surfactant using a polymer having a fluoro-aliphatic group derived from a fluoro-aliphatic compound which is prepared by a telomerization method (also referred to as a telomer method) or an oligomerization method (also referred to as an oligomer method) as the surfactant. The fluoro-aliphatic compound may be synthesized by the method described in Japanese Patent Application Laid-Open No. 2002-90991.

Examples of a surfactant corresponding to the above-described surfactant may include Megaface F178, F-470, F-473, F-475, F-476 and F-472 (manufactured by DIC Corporation), a copolymer of an acrylate having a $C_6F_{13}$ group (or methacrylate) with a (poly(oxyalkylene))acrylate (or methacrylate), a copolymer of an acrylate having a $C_3F_7$ group (or methacrylate) with a (poly(oxyethylene))acrylate (or methacrylate) and a (poly(oxypropylene))acrylate (or methacrylate), and the like.

Further, in the present invention, it is also possible to use a surfactant other than the fluorine-based and/or silicon-based surfactant, described in [0280] of U.S. Patent Application Publication No. 2008/0248425.

These surfactants may be used either alone or in combination of several thereof.

When the resist composition contains a surfactant, the amount of the surfactant used is preferably 0.0001% by mass to 2% by mass, and more preferably 0.0005 mol % to 1 mol %, based on the total amount of the resit composition (excluding the solvent).

On one hand, by adjusting the amount of the surfactant added to 10 ppm or less based on the total amount of the resist composition (excluding the solvent), the surface uneven distribution of the resin D relating to the present invention is increased, and accordingly, the surface of the resist film may be made to be more hydrophobic, thereby improving the water follow-up property at the of immersion exposure.

[6] (F) Onium Carboxylate Salt

The resist composition in the present invention may or may not contain a carboxylic acid onium salt. Examples of the onium carboxylate salt may include those described in to [0606] of U.S. Patent Application Publication No. 2008/0187860.

The onium carboxylate salt may be synthesized by reacting sulfonium hydroxide, iodonium hydroxide, ammonium hydroxide and carboxylic acid with silver oxide in an appropriate solvent.

When the resist composition contains a onium carboxylate salt, the content thereof is generally 0.1% by mass to 20% by mass, preferably 0.5% by mass to 10% by mass, and more preferably 1% by mass to 7% by mass, based on the total solid content of the composition.

[7] (G) Resin Having a Reduced Solubility in a Developer Containing an Organic Solvent Due to the Increased Polarity by the Action of an Acid The resist composition may contain a resin having a reduced solubility in a developer containing an organic solvent due to the increased polarity by the action of an acid.

Examples of the resin (G) may include the resins described in paragraph [0106] to paragraph [0203] of Japanese Patent Application Laid-Open No. 2008-292975.

When the resist composition contains the resin (G), the content is generally 0.1% by mass to 40% by mass, preferably 0.5% by mass to 30% by mass, and more preferably 1% by mass to 20% by mass based on the total solid of the composition.

[8] (H) Other Additives

The resist composition of the present invention may further contain a dye, a plasticizer, a photosensitizer, a light absorber, an alkali-soluble resin, a dissolution inhibitor, a compound for accelerating solubility in a developer (for example, a phenol compound having a molecular weight of 1,000 or less, or an alicyclic or aliphatic compound having a carboxyl group) and the like, if necessary.

The phenol compound having a molecular weight of 1,000 or less may be easily synthesized by a person skilled in the art in reference with the methods described in, for example, Japanese Patent Application Laid-Open No. H4-122938, Japanese Patent Application Laid-Open No. H2-28531, U.S. Pat. No. 4,916,210, European Patent No. 219294 and the like.

Specific examples of the alicyclic or aliphatic compound having a carboxylic acid include a carboxylic acid derivative having a steroid structure, such as cholic acid, deoxycholic acid and lithocholic acid, an adamantanecarboxylic acid derivative, adamantanedicarboxylic acid, cyclohexanecarboxylic acid, cyclohexanedicarboxylic acid and the like, but are not limited thereto.

The solid concentration of the resist composition in the present invention is usually 1.0% by mass to 10% by mass, preferably 2.0% by mass to 5.7% by mass, and more preferably 2.0% by mass to 5.3% by mass. By setting the solid concentration to the above-described range, the resist solution may be uniformly applied on a substrate and a resist pattern which is excellent in line edge roughness may be formed. The reason is not clear, but it is thought that by setting the solid concentration to 10% by mass or less, preferably 5.7% by mass or less, aggregation of materials, particularly, a photo-acid generator, in the resist solution is suppressed, and as a result, a uniform resist film may be formed.

The solid concentration is a weight percentage of the weight of other resist components excluding the solvent, based on the total weight of the resist composition.

[9] Pattern Forming Method

The negative type pattern forming method of the present invention at least includes (a) forming a film (resist film) by the chemical amplification composition of the present invention, (b) exposing the film, and (c) performing development using a developer containing an organic solvent.

The exposure in the step (b) may be immersion exposure.

The resist film is formed from the chemical amplification resist composition of the present invention, and more specifically, is preferably a film formed on a substrate. In the pattern forming method of the present invention, the step of forming a film by a resist composition on a substrate, the step of exposing the film, and the step of performing development may be performed by a generally known method.

Further, the present invention relates to a chemical amplification resist composition used in the above-mentioned negative type pattern forming method.

It is also preferred that the method includes, after film formation, a pre-baking step (PB) before the exposure step.

Further, it is also preferred that the method includes a post-exposure baking step (PEB) after the exposure step but before the development step.

As for the heating temperature, both PB and PEB are performed preferably at from 70° C. to 120° C., and more preferably at from 80° C. to 110° C.

The heating time is preferably 30 to 300 seconds, more preferably 30 to 180 seconds, and still more preferably 30 to 90 seconds.

The heating may be performed using a means equipped with a typical exposure/developing machine or may be performed using a hot plate or the like.

By means of baking, the reaction in the exposed portion is accelerated, and thus the sensitivity or pattern profile is improved.

The light source wavelength used in the exposure apparatus in the present invention is not limited, but examples thereof include an infrared light, visible light, ultraviolet light, far ultraviolet light, an extreme-ultraviolet light, X-ray, an electron beam and the like, but are preferably far ultraviolet light at a wavelength of preferably 250 nm or less, more preferably 220 nm or less, and particularly preferably 1 nm to 200 nm. Specific examples thereof include a KrF excimer laser (248 nm), an ArF excimer laser (193 nm), a $F_2$ excimer laser (157 nm), an X-ray, an EUV (13 nm), an electron beam and the like, and a KrF excimer laser, an ArF excimer laser, an EUV or an electron beam is preferred, and an ArF excimer laser is more preferred.

In the present invention, the substrate on which the film is formed is not particularly limited, and it is possible to use an inorganic substrate such as silicon, SiN, $SiO_2$ or SiN, a coating-type inorganic substrate such as SOG, or a substrate generally used in the process of manufacturing a semiconductor such as IC or manufacturing a liquid crystal device or a circuit board such as a thermal head or in the lithography process of other photo-fabrication processes. Further, if necessary, an organic antireflection film may be formed between the film and the substrate.

As the developer (hereinafter, also referred to as an "organic-based developer") in the step of performing developing using a developer containing an organic solvent, a polar solvent such as a ketone-based solvent, an ester-based solvent, an alcohol-based solvent, an amide-based solvent and an ether-based solvent, and a hydrocarbon-based solvent may be used.

Examples of the ketone-based solvent may include 1-octanone, 2-octanone, 1-nonanone, 2-nonanone, acetone, 2-heptanone (methyl amyl ketone), 4-heptanone, 1-hexanone, 2-hexanone, diisobutyl ketone, cyclohexanone, methylcyclohexanone, phenylacetone, methyl ethyl ketone, methyl isobutyl ketone, acetyl acetone, acetonyl acetone, ionone, diacetonyl alcohol, acetyl carbinol, acetophenone, methyl naphthyl ketone, isophorone, propylene carbonate and the like.

Examples of the ester-based solvent may include methyl acetate, butyl acetate, ethyl acetate, isopropyl acetate, pentyl acetate, isopentyl acetate, amyl acetate, propylene glycol monomethyl ether acetate, ethylene glycol monoethyl ether acetate, diethylene glycol monobutyl ether acetate, diethylene glycol monoethyl ether acetate, ethyl-3-ethoxypropionate, 3-methoxybutyl acetate, 3-methyl-3-methoxybutyl acetate, methyl formate, ethyl formate, butyl formate, propyl formate, ethyl lactate, butyl lactate, propyl lactate and the like.

Examples of the alcohol-based solvent may include an alcohol such as methyl alcohol, ethyl alcohol, n-propyl alcohol, isopropyl alcohol, n-butyl alcohol, sec-butyl alcohol, t-butyl alcohol, isobutyl alcohol, n-hexyl alcohol, n-heptyl alcohol, n-octyl alcohol and n-decanol, a glycol-based solvent such as ethylene glycol, diethylene glycol and triethylene glycol, a glycol ether-based solvent such as ethylene glycol monomethyl ether, propylene glycol monomethyl ether, ethylene glycol monoethyl ether, propylene glycol monoethyl ether, diethylene glycol monomethyl ether, triethylene glycol monoethyl ether and methoxymethyl butanol, and the like.

Examples of the ether-based solvent may include, in addition to the glycol ether-based solvents, dioxane, tetrahydrofuran and the like.

As the amide-based solvent, it is possible to use, for example, N-methyl-2-pyrrolidone, N,N-dimethylacetamide, N,N-dimethylformamide, hexamethylphosphoric triamide, 1,3-dimethyl-2-imidazolidinone and the like.

Examples of the hydrocarbon-based solvent may include an aromatic hydrocarbon-based solvent such as toluene and xylene, and an aliphatic hydrocarbon-based solvent such as pentane, hexane, octane and decane.

A plurality of the above-described solvents may be mixed, or the solvents may be used by being mixing with a solvent other than those described above or with water. However, in order to sufficiently exhibit the effects of the present invention, the water content of the entire developer is preferably less than 10% by mass, and it is more preferred that the developer contains substantially no moisture.

That is, the amount of the organic solvent used in the organic-based developer is preferably 90% by mass to 100% by mass, and more preferably 95% by mass to 100% by mass, based on the total amount of the developer.

In particular, the organic-based developer is preferably a developer containing at least one of organic solvents selected from the group consisting of a ketone-based solvent, an ester-based solvent, an alcohol-based solvent, an amide-based solvent and an ether-based solvent.

The vapor pressure of the organic-based developer is preferably 5 kPa or less, more preferably 3 kPa or less, and particularly preferably 2 kPa or less, at 20° C. By adjusting the vapor pressure of the organic-based developer to 5 kPa or less, evaporation of the developer on a substrate or in a development cup is suppressed so that the temperature uniformity in the wafer plane is improved, and as a result, the dimensional uniformity in the wafer plane is improved.

Specific examples of the solvent having a vapor pressure of 5 kPa or less may include a ketone-based solvent such as 1-octanone, 2-octanone, 1-nonanone, 2-nonanone, 2-heptanone (methyl amyl ketone), 4-heptanone, 2-hexanone, diisobutyl ketone, cyclohexanone, methylcyclohexanone, phenylacetone and methyl isobutyl ketone, an ester-based solvent such as butyl acetate, pentyl acetate, isopentyl acetate, amyl acetate, propylene glycol monomethyl ether acetate, ethylene glycol monoethyl ether acetate, diethylene glycol monobutyl ether acetate, diethylene glycol monoethyl ether acetate, ethyl-3-ethoxypropionate, 3-methoxybutyl acetate, 3-methyl-3-methoxybutyl acetate, butyl formate, propyl formate, ethyl lactate, butyl lactate and propyl lactate, an alcohol-based solvent such as n-propyl alcohol, isopropyl alcohol, n-butyl alcohol, sec-butyl alcohol, t-butyl alcohol, isobutyl alcohol, n-hexyl alcohol, n-heptyl alcohol, n-octyl alcohol and n-decanol, a glycol-based solvent such as ethylene glycol, diethylene glycol and triethylene glycol, a glycol ether-based solvent such as ethylene glycol monomethyl ether, propylene glycol monomethyl ether, ethylene glycol monoethyl ether, propylene glycol monoethyl ether, diethylene glycol monoethyl ether, triethylene glycol monoethyl ether and methoxymethylbutanol, an ether-based solvent such as tetrahydrofuran, an amide-based solvent such as N-methyl-2-pyrrolidone, N,N-dimethylacetamide and N,N-dimethylformamide, an aromatic hydrocarbon-based solvent such as toluene and xylene, and an aliphatic hydrocarbon-based solvent such as octane and decane.

Specific examples of the solvent having a vapor pressure of 2 kPa or less that is in a particularly preferred range may include a ketone-based solvent such as 1-octanone, 2-octanone, 1-nonanone, 2-nonanone, 4-heptanone, 2-hexanone, diisobutyl ketone, cyclohexanone, methylcyclohexanone and phenylacetone, an ester-based solvent such as butyl acetate, amyl acetate, propylene glycol monomethyl ether acetate, ethylene glycol monoethyl ether acetate, diethylene glycol monobutyl ether acetate, diethylene glycol monoethyl ether acetate, ethyl-3-ethoxypropionate, 3-methoxybutyl acetate, 3-methyl-3-methoxybutyl acetate, ethyl lactate, butyl lactate and propyl lactate, an alcohol-based solvent such as n-butyl alcohol, sec-butyl alcohol, t-butyl alcohol, isobutyl alcohol, n-hexyl alcohol, n-heptyl alcohol, n-octyl alcohol and n-decanol, a glycol-based solvent such as ethylene glycol, diethylene glycol and triethylene glycol, a glycol ether-based solvent such as ethylene glycol monomethyl ether, propylene glycol monomethyl ether, ethylene glycol monoethyl ether, propylene glycol monoethyl ether, diethylene glycol monomethyl ether, triethylene glycol monoethyl ether and methoxymethylbutanol, an amide-based solvent such as N-methyl-2-pyrrolidone, N,N-dimethylacetamide and N,N-dimethylformamide, an aromatic hydrocarbon-based solvent such as xylene, and an aliphatic hydrocarbon-based solvent such as octane and decane, and the like.

In the organic developer, a surfactant may be added in an appropriate amount, if necessary.

The surfactant is not particularly limited but, for example, ionic or nonionic fluorine-based and/or silicon-based surfactant and the like may be used. Examples of the fluorine and/or silicon-based surfactants include surfactants described in Japanese Patent Application Laid-Open Nos. S62-36663, S61-226746, S61-226745, S62-170950, S63-34540, H7-230165, H8-62834, H9-54432 and H9-5988, and U.S. Pat. Nos. 5,405,720, 5,360,692, 5,529,881, 5,296,330, 5,436,098, 5,576,143, 5,294,511 and 5,824,451, and a nonionic surfactant is preferred. The nonionic surfactant is not particularly limited, but a fluorine-based surfactant or a silicon-based surfactant is more preferably used.

The amount of the surfactant used is usually 0.001% by mass to 5% by mass, preferably 0.005% by mass to 2% by mass, and more preferably 0.01% by mass to 0.5% by mass, based on the total amount of the developer.

As for the developing method, it is possible to apply, for example, a method of dipping a substrate in a bath filled with a developer for a fixed time (dipping method), a method of raising a developer on a substrate surface sufficiently by the effect of a surface tension and keeping the substrate still for a fixed time, thereby performing development (puddle method), a method of spraying a developer on a substrate surface (spraying method), a method of continuously ejecting a developer on a substrate spinning at a constant speed while scanning a developer ejecting nozzle at a constant rate (dynamic dispense method) and the like.

When the above-described various developing methods include ejecting a developer toward a resist film from a development nozzle of a developing apparatus, the ejection pressure of the developer ejected (the flow velocity per unit area of the developer ejected) is preferably 2 mL/sec/mm$^2$ or less, more preferably 1.5 mL/sec/mm$^2$ or less, and still more preferably 1 mL/sec/mm$^2$ or less. The flow velocity has no particular lower limit, but is preferably 0.2 mL/sec/mm$^2$ or more in consideration of throughput.

By setting the ejection pressure of the ejected developer to the above-described range, pattern defects resulting from the resist scum after development may be significantly reduced. Details on the mechanism are not clear, but it is thought that by setting the ejection pressure in the above-described range, the pressure imposed on the resist film by the developer is decreased and the resist film or resist pattern is suppressed from being inadvertently cut or collapsing.

Further, the ejection pressure (mL/sec/mm$^2$) of the developer is the value at the outlet of the development nozzle in the developing apparatus.

Examples of the method for adjusting the ejection pressure of the developer include a method of adjusting the ejection pressure by a pump or the like, a method of supplying a developer from a pressurized tank and adjusting the pressure to change the ejection pressure and the like.

Further, after the step of performing development using a developer including an organic solvent, a step of stopping the development while replacing the solvent with another solvent may be performed.

A step of rinsing a film using a rinse liquid is preferably included after the step of performing development using a developer including an organic solvent.

The rinse liquid used in the rinsing step after the step of performing development using an developer including an organic solvent is not particularly limited as long as the rinse liquid does not dissolve the resist pattern, and a solution including a general organic solvent may be used. As for the rinse liquid, a rinse liquid containing at least one of organic solvents selected from the group consisting of a hydrocarbon-based solvent, a ketone-based solvent, an ester-based solvent, an alcohol-based solvent, an amide-based solvent and an ether-based solvent is preferably used.

Specific examples of the hydrocarbon-based solvent, the ketone-based solvent, the ester-based solvent, the alcohol-based solvent, the amide-based solvent and the ether-based solvent are the same as those described above for the developer including an organic solvent.

After the step of performing development using a developer including an organic solvent, more preferably, a step of performing washing using a rinse liquid containing at least one of organic solvent selected from the group consisting of a ketone-based solvent, an ester-based solvent, an alcohol-based solvent and an amide-based solvent is preformed, a step of performing washing using a rinse liquid containing an alcohol-based solvent or an ester-based solvent is still more preferably performed, a step of performing washing using a rinse liquid containing a monohydric alcohol is particularly preferably performed, and a step of performing washing using a rinse liquid containing a monohydric alcohol having 5 or more carbon atoms is most preferably performed.

Here, examples of the monohydric alcohol used in the rinsing step includes a straight chained, branched or cyclic monohydric alcohol, and specifically, it is possible to use 1-butanol, 2-butanol, 3-methyl-1-butanol, t-butyl alcohol, 1-pentanol, 2-pentanol, 1-hexanol, 4-methyl-2-pentanol, 1-heptanol, 1-octanol, 2-hexanol, cyclopentanol, 2-heptanol, 2-octanol, 3-hexanol, 3-heptanol, 3-octanol, 4-octanol and the like, and as the particularly preferred monohydric alcohol having 5 or more carbon atoms, it is possible to use 1-hexanol, 2-hexanol, 4-methyl-2-pentanol, 1-pentanol, 3-methyl-1-butanol and the like.

A plurality of the components may be mixed, or the solvent may be used by being mixed with an organic solvent other than those described above.

The water content in the rinse liquid is preferably 10% by mass or less, more preferably 5% by mass or less, and particularly preferably 3% by mass or less. By setting the water content to 10% by mass or less, good development characteristics may be obtained.

The vapor pressure of the rinse liquid used after the step of performing development using a developer including an organic solvent is preferably 0.05 kPa to 5 kPa, still more preferably 0.1 kPa to 5 kPa, and most preferably 0.12 kPa to 3 kPa, at 20° C. By setting the vapor pressure of the rinse liquid to 0.05 kPa to 5 kPa, the temperature uniformity in the wafer plane is improved, and furthermore, swelling caused by permeation of the rinse liquid is suppressed, and as a result, the dimensional uniformity in the wafer plane is improved.

The rinse liquid may also be used by adding an appropriate amount of a surfactant thereto.

In the rinsing step, the wafer subjected to development using a developer including an organic solvent is rinsed by using the above-described rinse liquid including an organic solvent. The method of rinsing treatment is not particularly limited, but it is possible to apply, for example, a method of continuously ejecting a rinse liquid on a substrate spinning at a constant speed (spin coating method), a method of dipping a substrate in a bath filled with a rinse liquid for a fixed time (dipping method), a method of spraying a rinse liquid on a substrate surface (spraying method), and the like, and among them, it is preferred that the rinsing treatment is performed by the spin coating method and after the rinsing, the substrate is spun at a rotational speed from 2,000 rpm to 4,000 rpm to remove the rinse liquid from the substrate. It is also preferred that a heating step (post baking) is included after the rinsing step. The developer and rinse liquid remaining between patterns and in the inside of the pattern are removed by the baking. The heating step after the rinsing step is performed at usually 40° C. to 160° C., and preferably 70° C. to 95° C., for usually 10 seconds to 3 minutes, and preferably 30 to 90 seconds.

EXAMPLE

Hereinafter, the present invention will be described with reference to Examples, but the present invention is not limited thereto.

Synthesis Example 1

Synthesis of Fullerene Derivative (1)

$C_{60}(OH)_{5.2}(O-CH_2C(=O)O^tBu)_{4.8}$ was prepared in the same manner as in Example 1 of Japanese Patent Application Laid-Open No. 2010-116380.

That is, 8 g of potassium carbonate and 10 mL (68.2 mmol) of tert-butyl bromoacetate were added to a suspension of 1.0 g (1.12 mmol) of fullerene hydroxide (average hydroxyl value: 10) $C_{60}(OH)_{10}$ manufactured in Frontier Carbon Corporation in tetrahydrofuran (THF) (20 mL) and acetone (40 mL), followed by stirring at 25° C. for 1 hour. After that, the reaction solution was heated to 55° C. and further stirred for 12 hours. Then, the reaction solution was filtered through Celite (eluent: ethyl acetate) to remove the solvent, and then, ethyl acetate and water were added to perform a liquid separation. The organic phase was dried over sodium sulfate and filtered to concentrate the solution, and then, crystallization was performed with 300 mL of hexane, followed by drying under vacuum at 50° C. to obtain the fullerene derivative (1) of $C_{60}(OH)_{5.2}(O-CH_2C(=O)O^tBu)_{4.8}$ as a brown solid (0.74 g; 46% yield).

Synthesis Example 2

Synthesis of Fullerene Derivative (2)

2.1 g (13.5 mmol) of octyl vinyl ether and 2.3 mg (0.01 mmol) of camphorsulfonic acid were added to a suspension of 1.0 g (1.12 mmol) of fullerene hydroxide (average hydroxyl value: 10) $C_{60}(OH)_{10}$ manufactured in Frontier Carbon Corporation in tetrahydrofuran (THF) (20 mL) and acetone (40 mL), followed by stirring for 24 hours. Then, the reaction solution was filtered through Celite (eluent: ethyl acetate) to remove the solvent, and then, ethyl acetate and water were added to perform a liquid separation. The organic phase was dried over sodium sulfate and filtered to concentrate the solution, and then, crystallization was performed with 300 mL of a mixed solvent of methanol-water (95:5), followed by drying under vacuum at 50° C. to obtain the fullerene derivative (2) of $C_{60}(OH)_6(O-CH(CH_3)OC_8H_{17})_4$ as a brown solid (0.44 g; 26% yield).

<Preparation of Resist Composition>

The resist compositions of Examples 1 to 11 and Comparative Example 1 were prepared by dissolving the components as shown in Table below in the solvents as shown in Table 1, and filtering each of them by a polytetrafluoroethylene filter having a pore size of 0.1 μm.

TABLE 1

| | Fullerene derivative | | Polymer | | | | | Acid generator 1 | | Acid generator 2 | | Basic compound 1 | |
|---|---|---|---|---|---|---|---|---|---|---|---|---|---|---|
| | Comp. No. | Part by weight | Comp. No. | Mw | Mw/Mn | Composition ratio (Molar ratio) | Part by weight | Comp. No. | Part by weight | Comp. No. | Part by weight | Comp. No. | Part by weight |
| Ex. 1 | 1 | 89.7 | | | | | | PAG-1 | 5.0 | PAG-9 | 4.0 | N-1 | 0.80 |
| Ex. 2 | 1 | 88.9 | | | | | | PAG-3 | 7.0 | PAG-11 | 2.0 | N-2 | 0.50 |
| Ex. 3 | 1 | 77.3 | CA-1 | 10100 | 1.85 | 40 10 50 | 15.0 | PAG-2 | 4.0 | PAG-4 | 2.0 | N-1 | 0.70 |
| Ex. 4 | 1 | 89.5 | | | | | | PAG-8 | 5.0 | PAG-12 | 3.0 | N-4 | 0.50 |
| Ex. 5 | 1 | 82.5 | CA-1 | 10100 | 1.85 | 40 10 50 | 10.0 | PAG-6 | 7.0 | | | N-3 | 0.30 |
| Ex. 6 | 1 | 91.6 | | | | | | PAG-7 | 3.0 | PAG-10 | 4.0 | N-1 | 0.40 |
| Ex. 7 | 1 | 90.8 | | | | | | PAG-13 | 7.0 | PAG-5 | 1.0 | N-1 | 0.70 |
| Ex. 8 | 2 | 91.5 | | | | | | PAG-1 | 5.0 | PAG-12 | 2.0 | N-2 | 0.70 |
| Ex. 9 | 2 | 90.7 | | | | | | PAG-6 | 6.0 | PAG-10 | 1.5 | N-2 | 0.70 |
| Ex. 10 | 2 | 68.0 | CA-1 | 10100 | 1.85 | 40 10 50 | 20.0 | PAG-2 | 7.0 | PAG-7 | 4.0 | N-3 | 0.90 |
| Ex. 11 | 2 | 80.1 | CA-1 | 10100 | 1.85 | 40 10 50 | 10.0 | PAG-4 | 7.5 | PAG-11 | 1.0 | N-1 | 0.70 |
| C.Ex. 1 | None | | CA-1 | 10100 | 1.85 | 40 10 50 | 91.8 | PAG-1 | 7.0 | | | N-1 | 0.70 |

| | Basic compound 2 | | Additive | | Surfactant | | Solvent | | | | | |
|---|---|---|---|---|---|---|---|---|---|---|---|---|
| | Comp. No. | Part by weight | Comp. No. | Part by weight | Comp. No. | Part by weight | Solvent 1 | Part by weight | Solvent 2 | Part by weight | Solvent 3 | Part by weight |
| Ex. 1 | | | | | W-2 | 0.50 | SL-1 | 1292 | SL-6 | 800 | SL-7 | 30 |
| Ex. 2 | N-3 | 0.10 | AD-1 | 1.0 | W-3 | 0.50 | SL-1 | 1952 | SL-5 | 100 | SL-7 | 70 |
| Ex. 3 | | | | | W-6 | 1.00 | SL-1 | 622 | SL-6 | 1500 | | |
| Ex. 4 | | | AD-2 | 1.5 | W-4 | 0.50 | SL-1 | 1822 | SL-4 | 200 | SL-7 | 100 |
| Ex. 5 | N-5 | 0.20 | | | | | SL-1 | 1802 | SL-3 | 300 | SL-8 | 20 |
| Ex. 6 | | | | | W-5 | 1.00 | SL-6 | 1472 | SL-1 | 650 | | |
| Ex. 7 | | | | | W-1 | 0.50 | SL-1 | 1422 | SL-6 | 600 | SL-2 | 100 |
| Ex. 8 | N-3 | 0.30 | | | W-1 | 0.50 | SL-1 | 1422 | SL-6 | 600 | SL-2 | 100 |
| Ex. 9 | N-1 | 0.10 | | | W-6 | 1.00 | SL-1 | 1322 | SL-6 | 800 | | |
| Ex. 10 | N-5 | 0.10 | | | | | SL-1 | 1472 | SL-3 | 600 | SL-7 | 50 |
| Ex. 11 | N-2 | 0.20 | | | W-5 | 0.50 | SL-1 | 1422 | SL-4 | 600 | SL-2 | 100 |
| C.Ex. 1 | | | | | W-2 | 0.50 | SL-1 | 1722 | SL-6 | 400 | | |

The abbreviatons in Table 1 are as follows.
PAG-1 to PAG-13: represent the following compounds, respectively.
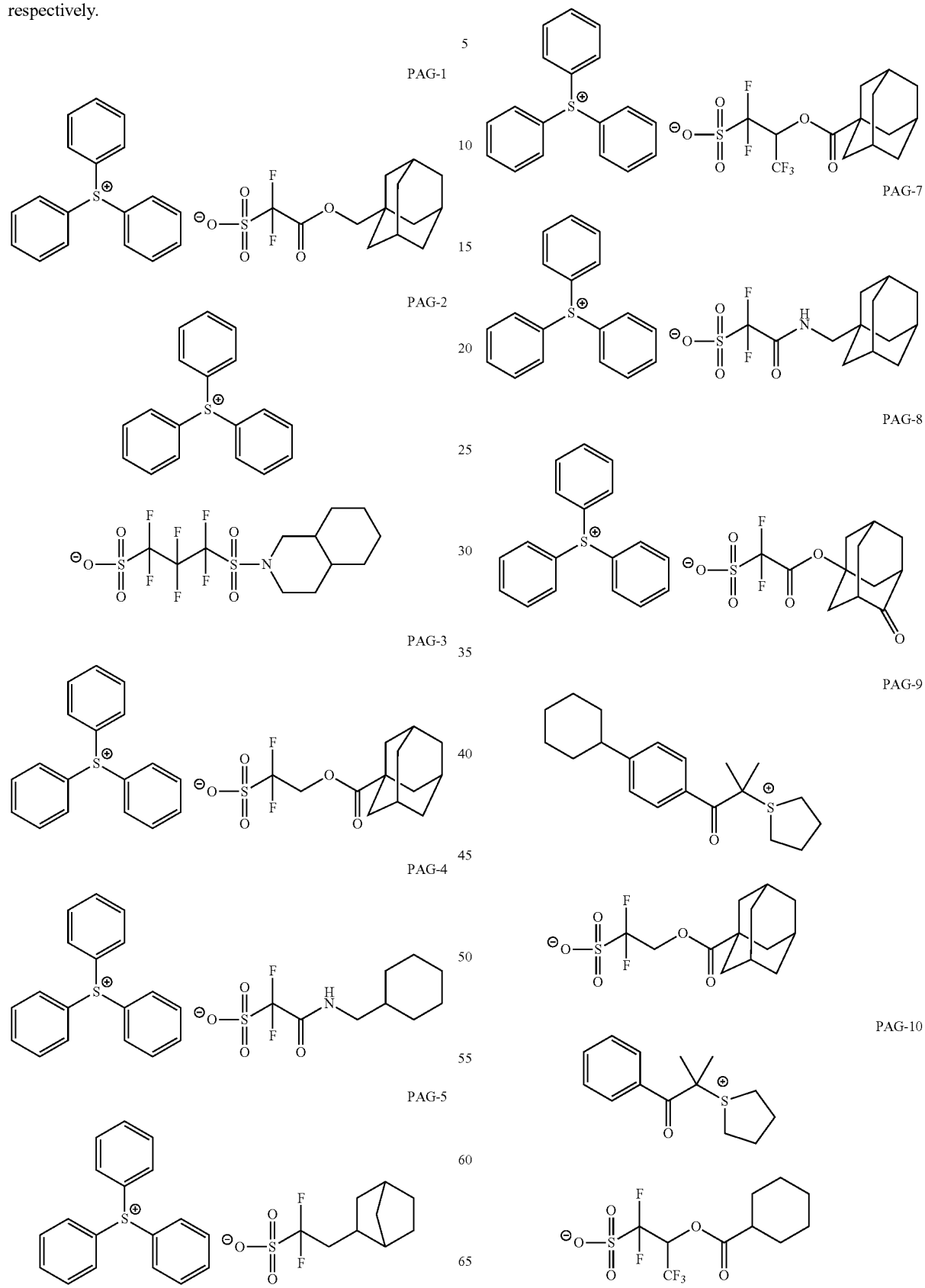

PAG-11

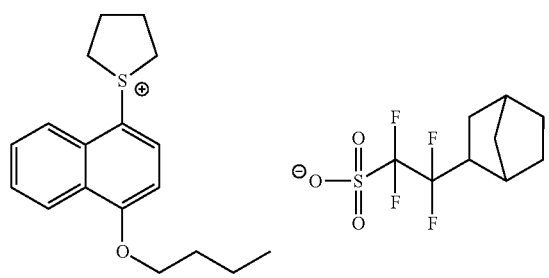

PAG-12

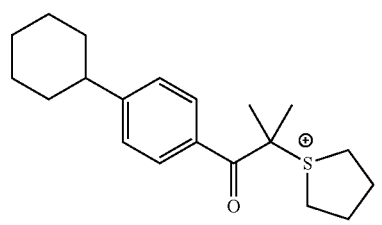

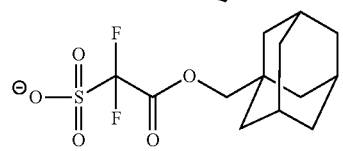

PAG-13

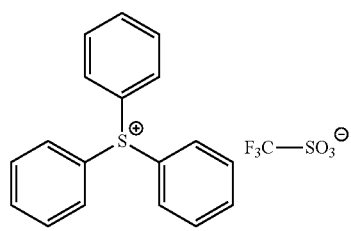

CA-1: represents the following resins. The ratio of repeating units, the mass average molecular weight (Mw) and the degree of dispersion (Mw/Mn) are as shown in Table 1.

CA-1

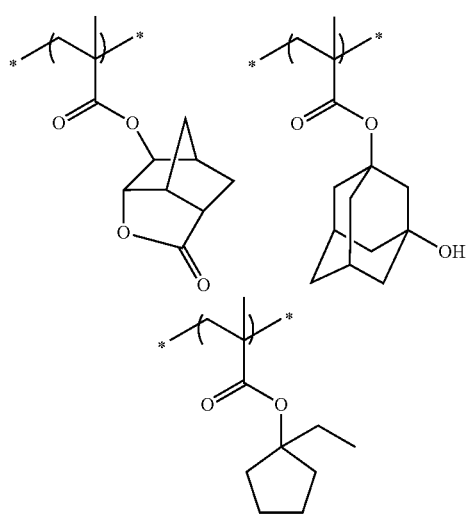

N-1 to N-5: represent the following compounds, respectively.

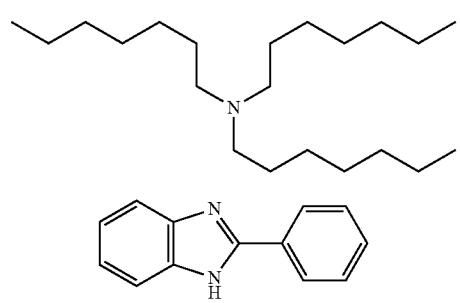

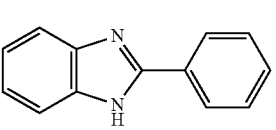

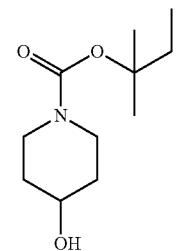

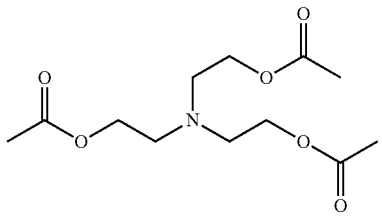

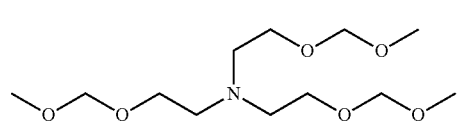

AD-1 to AD-2: represent the following compounds, respectively.

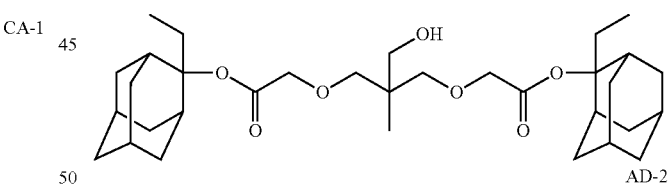

W-1: Megaface F176 (manufactured by DIC Corporation; fluorine-based)
W-2: Megaface R08 (manufactured by DIC Corporation; fluorine and silicon-based)
W-3: Polysiloxane Polymer KP-341 (manufactured by Shin-Etsu Chemical Co., Ltd.; silicon-based)

W-4: Troysol S-366 (manufactured by Troy Chemical Corp.)

W-5: KH-20 (manufactured by Asahi Glass Co., Ltd.)

W-6: PolyFox PF-6320 (manufactured by OMNOVA Solutions Inc.; fluorine-based)

Group a

SL-1: Propylene glycol monomethyl ether acetate (PGMEA)

SL-2: Propylene glycol monomethyl ether propionate

SL-3: 2-Heptanone

Group b

SL-4: Ethyl lactate

SL-5: Propylene glycol monomethyl ether (PGME)

SL-6: Cyclohexanone

Group c

SL-7: γ-Butyrolactone

SL-8: Propylene carbonate

Resist patterns were formed using the prepared resist composition by the following method.

Example 1

The prepared resist composition was uniformly applied onto a hexamethyldisilazane-treated silicon substrate by using a spin coater, and heat-dried on a hot plate at 110° C. for 90 seconds to form a resist film having a film thickness of 10 nm.

The resist film was subjected to irradiation with an electon beam using an electron irradiation apparatus (HL750 manufactured by Hitachi, Ltd., acceleration voltage: 50 keV). Immediately after the irradiation, the resist film was heated on a hot plate at 120° C. for 90 seconds. Further, the resist film was developed using buty acetate at 23° C. for 60 seconds, rinsed with 4-methyl-2-pentanol for 30 seconds, and dried to obtain a resist pattern having 1:1 line and space pattern having a line width of 100 nm.

Examples 2 to 11 and Comparative Example 1

Resist patterns having 1:1 line and space pattern having a line width of 100 nm were obtained in the same manner as in Example 1, except that the resist compositions as shown in Table 1 were used.

<Evaluation Method>

[Sensitivity]

The cross-sectional shape of the obtained patterns was observed with a scanning electron microscope (S-9220 manufactured by Hitachi, Ltd.). The irradiation energy (Eopt) when resolving 1:1 line and space pattern having a line width of 100 nm was designated as sensitivity.

[Resolution]

A limiting resolution (the minimum line width at which the line and the space are separately resolved) in the irradiation quantity indicating the sensitivity described above was designated as a resolution. The smaller the value, the better capability is indicated.

[Line Edge Roughness (LER)]

Concerning arbitrary 30 points in 50 μm in the longitudinal direction of line pattern having a line width of 100 nm in the irradiation quantity indicating the sensitivity described above, a distance from a base line at which edges should be located was measured with a scanning electron microscope (S-9220 manufactured by Hitachi, Ltd.), and standard deviation was obtained to calculate a standard deviation of 3σ (nm).

[Development Time Dependency]

By performing the same evaluation was performed, except that the development time is set to 120 seconds, a difference between the Eopt at the development time of 60 seconds and the Eopt at the development time of 120 seconds, that is, a degree of variation (ΔEopt/Eopt) of the sensitivity was calculated from a variation of the sensitivity (ΔEopt), and was evaluated using a relative value when Comparative Example 1 is set to 100. The smaller value means that the variation of sensitivity is small, the development time dependency is good, and the development process latitude is large.

[Dry Etching Resistance]

The prepared resist composition was uniformly applied onto a hexamethyldisilazane-treated silicon substrate by using a spin coater, and heat-dried on a hot plate at 110° C. for 90 seconds to form a resist film having a film thickness of 10 nm.

The resist film was subjected to irradiation with a electon beam using an electron irradiation apparatus (HL750 manufactured by Hitachi, Ltd., acceleration voltage: 50 keV). Immediately after the irradiation, the resist film was heated on a hot plate at 120° C. for 90 seconds. Further, the resist film was developed using buty acetate at 23° C. for 60 seconds, rinsed with 4-methyl-2-pentanol for 30 seconds, and dried to optain a resist pattern having 1:1 line and space pattern having a line width of 100 nm.

The resist compositions of Examples and Comparative Example were uniformly applied onto a hexamethyldisilazane-treated silicon substrate using a spin coater, heat-dried on a hot plate by heating at 110° C. for 90 seconds to form a resist film having a film thickness of 100 nm. The entire surface of the obtained resist film is subjected to irradiation at an exposure quantity of 20 μC/cm$^2$ using an electron beam irradiation apparatus (HL750 manufactured by Hitachi, Ltd., acceleration voltage: 50 keV), and baked at 110° C. for 60 seconds, and then the thickness of the resist film was measured.

Thereafter, a plasma etching was performed at a temperature of 23° C. for 30 seconds using a mixed gas of $CF_4$ (10 mL/min), $O_2$ (20 mL/min) and Ar (1000 mL/min). Thereafter, a remaining film quantity of the resist film was measured and an etching rate was designated as a value obtained by dividing a difference between the measured remaining film quantity and the thickness of the resist film subjected to exposure and bake by 30 seconds, which is an etching time.

The smaller the etching rate is, a plasma etching resistance is better. A relative value when Comparative Example 1 is set to 100 is indicated in Table 2.

TABLE 2

| | Performance evaluation results | | | | |
|---|---|---|---|---|---|
| | Sensitivity (μC/cm$^2$) | Resolution (nm) | LER (nm) | Etching rate | Development time dependency |
| Example 1 | 23.0 | 55 | 5.5 | 76 | 50 |
| Example 2 | 22.0 | 60 | 5.6 | 72 | 40 |
| Example 3 | 20.0 | 55 | 5.6 | 85 | 60 |
| Example 4 | 21.0 | 60 | 5.4 | 70 | 45 |
| Example 5 | 22.0 | 60 | 4.9 | 87 | 60 |
| Example 6 | 22.0 | 55 | 4.8 | 72 | 40 |
| Example 7 | 23.0 | 68 | 5.8 | 75 | 75 |
| Example 8 | 19.0 | 55 | 5.4 | 79 | 35 |
| Example 9 | 19.0 | 60 | 5.5 | 79 | 35 |
| Example 10 | 20.0 | 60 | 5.4 | 88 | 45 |
| Example 11 | 19.0 | 60 | 5.5 | 85 | 40 |
| Comparative Example 1 | 36.0 | 70 | 6.5 | 100 | 100 |

From Table 2, It has been found out that a film obtained from the resist composition of the present invention using the fullerene derivative having acid-decomposable group, which has been exposed with an electron beam, and then, developed with the developer containing an organic solvent, satisfies high sensitivity, high resolution, good roughness capability, high dry etching resistance and good development time dependency at the same time, as compared to the comparative example where an acid-decomposable resin is used instead of the fullerene derivative.

Further, also even in the case where exposure by an electron beam is replaced with exposure by EUV, a good effect can also be exhibited according to the resist composition.

Industrial Applicability

According to the present invention, it is possible to provide a pattern forming method, a chemical amplification resist composition and a resist film that satisfies high sensitivity, high resolution, good roughness and good dry etching resistance at the same time, and further, has a good development time dependency.

Although the present invention has been described with reference to detailed and specific embodiments thereof, it is obvious to those skilled in the art that various changes or modifications may be made without departing from the spirit and scope of the present invention.

The present application is based on Japanese Patent Application (Patent Application No. 2010-208625) filed on Sep. 16, 2010, the contents of which are herein incorporated by reference.

The invention claimed is:

1. A negative type pattern forming method comprising the steps of:
(i) forming a film by a chemical amplification resist composition essentially consisting of (A) a fullerene derivative having an acid-decomposable group, (B) a compound generating an acid upon irradiation with an actinic ray or radiation, (C) a solvent, and (D) a basic compound,
(ii) exposing the film, and
(iii) developing the exposed film by using an organic solvent-containing developer.

2. The negative type pattern forming method of claim 1, wherein the content of an organic solvent in the organic solvent-containing developer is 90% by mass to 100% by mass based on the total amount of the developer.

3. The negative type pattern forming method of claim 1, wherein the content of the fullerene derivative (A) is 30% by mass to 99% by mass based on the total solids of the resist composition.

4. The negative type pattern forming method of claim 1, wherein the compound (B) is a compound generating a sulfonic acid represented by the following Formula (BI) or Formula (I) upon irradiation with an actinic ray or radiation:

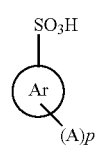

(BI)

wherein, in Formula (BI),
Ar represents an aromatic ring,
p represents an integer of 0 or more, and
A represents a group having a hydrocarbon group, and when p is 2 or more, each A may be the same as or different from every other A:

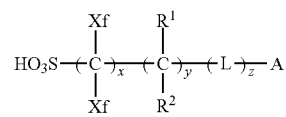

(I)

wherein in formula, each Xf independently represents a fluorine atom or an alkyl group substituted with at least one fluorine atom,
each of $R^1$ and $R^2$ independently represents a group selected from the group consisting of a hydrogen atom, a fluorine atom and an alkyl group, and when a plurality of $R^1$ and $R^2$ are present, each of $R^1$ and $R^2$ may be the same as or different from every other $R^1$ and $R^2$,
L represents a divalent linking group, and when a plurality of L are present, each L may be the same as or different from every other L,
A represents a cyclic organic group, and
x represents an integer of 1 to 20, y represents an integer of 0 to 10, and z represents an integer of 0 to 10.

5. The negative type pattern forming method of claim 1, wherein the fullerene derivative (A) has a partial structure represented by the following Formula (a1) or Formula (a2):

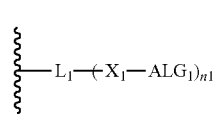

(a1)

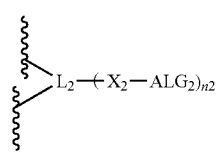

(a2)

wherein in the formula, each of $ALG_1$ and $ALG_2$ independently represents a group capable of leaving by the action of an acid, when n1 is an integer of 2 or more, each $ALG_1$ may be bound with each other, and when n2 is an integer of 2 or more, each $ALG_2$ may be bound with each other,
$L_1$ represents a single bond or an (n1+1)-valent linking group, bound to one of carbon atoms forming a fullerene structure,
$L_2$ represents an (n2+2)-valent linking group bound to two of carbon atoms forming a fullerene structure,
each of $X_1$ and $X_2$ independently represents —O— or —COO—, and
each of n1 and n2 independently represents an integer of 1 to 6.

6. The negative type pattern forming method of claim 1, wherein the acid-decomposable group is a structure protected by a leaving group in which an alcoholic hydroxyl group is capable of decomposing and leaving by the action of an acid.

7. The negative type pattern forming method of claim 1, wherein the developer is a developer containing at least one organic solvent selected from the group consisting of a ketone-based solvent, an ester-based solvent, an alcohol-based solvent, an amide-based solvent and an ether-based solvent.

8. The negative type pattern forming method of claim 1 further comprising (iv) washing with a rinse liquid containing an organic solvent.

9. A chemical amplification resist composition, essentially consisting of:
(A) a fullerene derivative having an acid-decomposable group,
(B) a compound generating an acid upon irradiation with an actinic ray or radiation,
(C) a solvent, and
(D) a basic compound,
wherein the compound (B) is a compound generating a sulfonic acid represented by the following Formula (BI) or Formula (I) upon irradiation with an actinic ray or radiation:

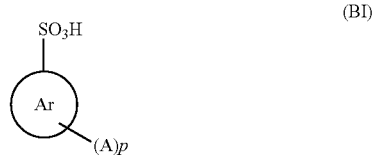

(BI)

wherein, in Formula (BI),
Ar represents an aromatic ring,
p represents an integer of 0 or more, and
A represents a group having a hydrocarbon group, and when p is 2 or more, each A may be the same as or different from every other A:

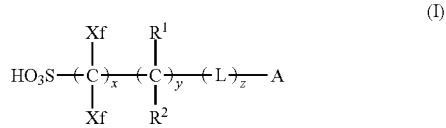

(I)

wherein in the formula, each Xf independently represents a fluorine atom or an alkyl group substituted with at least one fluorine atom,
each of $R^1$ and $R^2$ independently represents a group selected from a hydrogen atom, a fluorine atom and an alkyl group, and when a plurality of $R^1$ and $R^2$ are present, each of $R^1$ and $R^2$ may be the same as or different from every other $R^1$ and $R^2$,
L represents a divalent linking group, and when a plurality of L are present, each L may be the same as or different from every other L,
A represents a cyclic organic group, and
x represents an integer of 1 to 20, y represents an integer of 0 to 10, and z represents an integer of 0 to 10.

10. The chemical amplification resist composition of claim 9,
wherein the fullerene derivative (A) has a partial structure represented by the following Formula (a1) or Formula (a2):

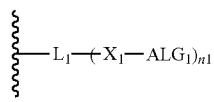

(a1)

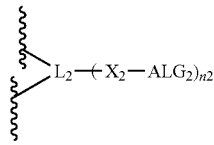

(a2)

wherein in the formula,
each of $ALG_1$ and $ALG_2$ independently represents a group capable of leaving by the action of an acid, when n1 is an integer of 2 or more, each $ALG_1$ may be bound with each other, and when n2 is an integer of 2 or more, each $ALG_2$ may be bound with each other,
$L_1$ represents a single bond or an (n1+1)-valent linking group bound to one of carbon atoms forming a fullerene structure,
$L_2$ represents an (n2+2)-valent linking group bound to two of carbon atoms forming a fullerene structure,
each of $X_1$ and $X_2$ independently represents —O— or —COO—, and
each of n1 and n2 independently represents an integer of 1 to 6.

11. The chemical amplification resist composition of claim 9,
wherein the acid-decomposable group has a structure protected by a leaving group in which an alcoholic hydroxyl group is capable of decomposing and leaving by the action of an acid.

12. A resist film formed by the chemical amplification resist composition of claim 9.

13. The negative type pattern forming method of claim 1,
wherein the acid-decomposable group in the fullerene derivative has a partial structure represented by formula (a1):

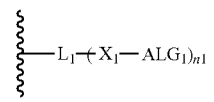

(a1)

wherein:
$ALG_1$ represents a group capable of leaving by the action of an acid;
$L_1$ is a single bond;
$X_1$ represents —O— or —COO—; and
n1 is 1.

14. The negative type pattern forming method of claim 13, wherein $X_1$ is —O—.

15. The negative type pattern forming method of claim 1, wherein the content of the fullerene derivative (A) is 55% by mass to 95% by mass, based on the total solids content of the resist composition.

16. The negative type pattern forming method of claim 7, wherein the developer contains an ester-based solvent.

17. The negative type pattern forming method of claim 16, wherein the developer further contains butyl acetate.

* * * * *